(12) United States Patent
Chu

(10) Patent No.: US 11,446,179 B2
(45) Date of Patent: Sep. 20, 2022

(54) OCULAR DEVICE AND METHOD FOR GLAUCOMA TREATMENT

(71) Applicant: Jack Chu, Santa Rosa, CA (US)

(72) Inventor: Jack Chu, Santa Rosa, CA (US)

(*) Notice: Subject to any disclaimer, the term of this patent is extended or adjusted under 35 U.S.C. 154(b) by 794 days.

(21) Appl. No.: 16/374,096

(22) Filed: Apr. 3, 2019

(65) Prior Publication Data

US 2019/0298572 A1   Oct. 3, 2019

Related U.S. Application Data

(60) Provisional application No. 62/743,785, filed on Oct. 10, 2018, provisional application No. 62/673,409, filed on May 18, 2018, provisional application No. 62/659,137, filed on Apr. 18, 2018, provisional application No. 62/652,052, filed on Apr. 3, 2018.

(51) Int. Cl.
| | |
|---|---|
| *A61F 9/007* | (2006.01) |
| *A61F 9/00* | (2006.01) |
| *A61F 9/008* | (2006.01) |
| *A61K 9/00* | (2006.01) |

(Continued)

(52) U.S. Cl.
CPC .......... *A61F 9/00781* (2013.01); *A61F 9/008* (2013.01); *A61F 9/0017* (2013.01); *A61K 9/0051* (2013.01); *A61B 3/165* (2013.01); *A61F 2009/00891* (2013.01); *A61M 27/002* (2013.01); *A61M 2210/0612* (2013.01)

(58) Field of Classification Search
CPC .... A61F 9/00781; A61F 9/0017; A61F 9/008; A61F 2009/00891; A61K 9/0051; A61B 3/165; A61M 27/002; A61M 2210/0612
See application file for complete search history.

(56) References Cited

U.S. PATENT DOCUMENTS

| | | |
|---|---|---|
| 3,788,327 A | 1/1974 | Donowitz et al. |
| 4,402,681 A | 9/1983 | Haas et al. |

(Continued)

FOREIGN PATENT DOCUMENTS

| | | |
|---|---|---|
| WO | WO 2004/060219 A1 | 7/2004 |
| WO | 2017059272 A1 | 4/2017 |
| WO | 2018009556 A1 | 1/2018 |

OTHER PUBLICATIONS

International Preliminary Report on Patentability and Written Opinion issued in PCT/US2019/025579, dated Oct. 15, 2020.

(Continued)

*Primary Examiner* — Philip R Wiest
(74) *Attorney, Agent, or Firm* — IceMiller LLP

(57) ABSTRACT

An ocular device for treating glaucoma in an eye are described herein. The ocular device includes a first end, a second end, and a body. The first end is configured to seat in an anterior chamber of an eye. The first end includes an inlet configured to facilitate an ingress of aqueous humor into the ocular device. The second end is configured to seat in a tear film of the eye. The second end includes an outlet configured to facilitate release a flow of the aqueous humor into the tear film. The body is defined by a fluid conduit. The body includes a lumen having a lumen length and a lumen cross sectional area. The lumen length and the lumen cross sectional area are configured to control an intraocular pressure (IOP) of the eye by controlling the flow of the aqueous humor through the lumen.

34 Claims, 38 Drawing Sheets

(51) Int. Cl.
*A61M 27/00* (2006.01)
*A61B 3/16* (2006.01)

(56) References Cited

U.S. PATENT DOCUMENTS

| | | | |
|---|---|---|---|
| 4,554,918 A | 11/1985 | White | |
| 4,634,418 A | 1/1987 | Binder | |
| 5,300,020 A | 4/1994 | LEsperance, Jr. | |
| 5,326,345 A | 7/1994 | Price, Jr. | |
| 5,346,464 A | 9/1994 | Camras | |
| 5,626,559 A | 5/1997 | Solomon | |
| 5,702,414 A | 12/1997 | Richter et al. | |
| 5,743,868 A | 4/1998 | Brown et al. | |
| 5,807,302 A | 9/1998 | Wandel | |
| 6,077,299 A | 6/2000 | Adelberg et al. | |
| 6,186,974 B1 | 2/2001 | Allan et al. | |
| 6,595,945 B2 | 7/2003 | Brown | |
| 6,699,210 B2 | 3/2004 | Williams et al. | |
| 6,881,198 B2 | 4/2005 | Brown | |
| 7,431,709 B2* | 10/2008 | Pinchuk | A61F 9/00781 604/9 |
| 7,641,627 B2 | 1/2010 | Camras et al. | |
| 7,780,623 B2 | 8/2010 | Soltanpour | |
| 8,617,139 B2 | 12/2013 | Silvestrini et al. | |
| 8,888,734 B2 | 11/2014 | Nissan et al. | |
| 8,915,877 B2* | 12/2014 | Cunningham, Jr. | A61F 9/00781 604/9 |
| 9,125,723 B2 | 9/2015 | Horvath et al. | |
| 9,186,274 B2 | 11/2015 | Camras et al. | |
| 9,283,115 B2 | 3/2016 | Lind et al. | |
| 9,375,347 B2 | 6/2016 | Stergiopulos | |
| 9,681,983 B2 | 6/2017 | Lind | |
| 2003/0079329 A1* | 5/2003 | Yaron | A61M 27/002 29/428 |
| 2003/0212007 A1 | 11/2003 | Prasad | |
| 2004/0260227 A1 | 12/2004 | Lisk, Jr. et al. | |
| 2005/0277864 A1 | 12/2005 | Haffner et al. | |
| 2006/0212007 A1 | 9/2006 | Peters et al. | |
| 2006/0235367 A1* | 10/2006 | Takashima | A61F 9/00781 604/541 |
| 2006/0276739 A1* | 12/2006 | Brown | A61F 9/00781 604/8 |
| 2007/0156079 A1 | 7/2007 | Brown | |
| 2010/0056977 A1 | 3/2010 | Wandel | |
| 2010/0249691 A1* | 9/2010 | Van Der Mooren | A61F 9/00781 604/9 |
| 2014/0081194 A1* | 3/2014 | Burns | A61P 27/06 604/8 |
| 2015/0335487 A1* | 11/2015 | de Juan, Jr. | A61F 9/007 604/8 |
| 2016/0058615 A1* | 3/2016 | Camras | A61F 9/00781 604/9 |
| 2016/0058616 A1 | 3/2016 | Camras et al. | |
| 2016/0287439 A1 | 10/2016 | Stergiopulos | |
| 2017/0087016 A1 | 3/2017 | Camras | |

OTHER PUBLICATIONS

European Patent Application No. 19780586.4; Extended Search Report; dated Nov. 4, 2021; 11 pages.

* cited by examiner

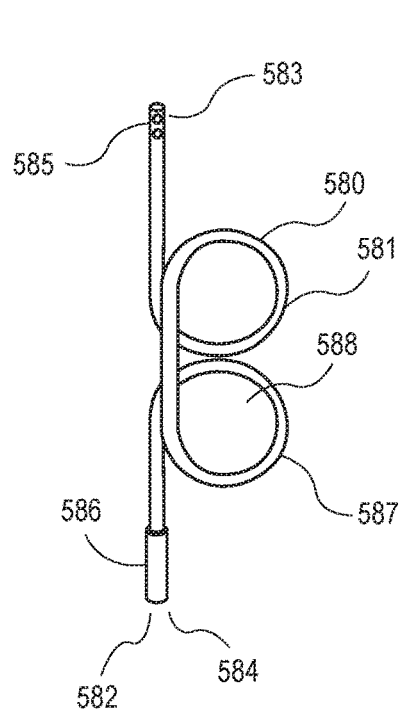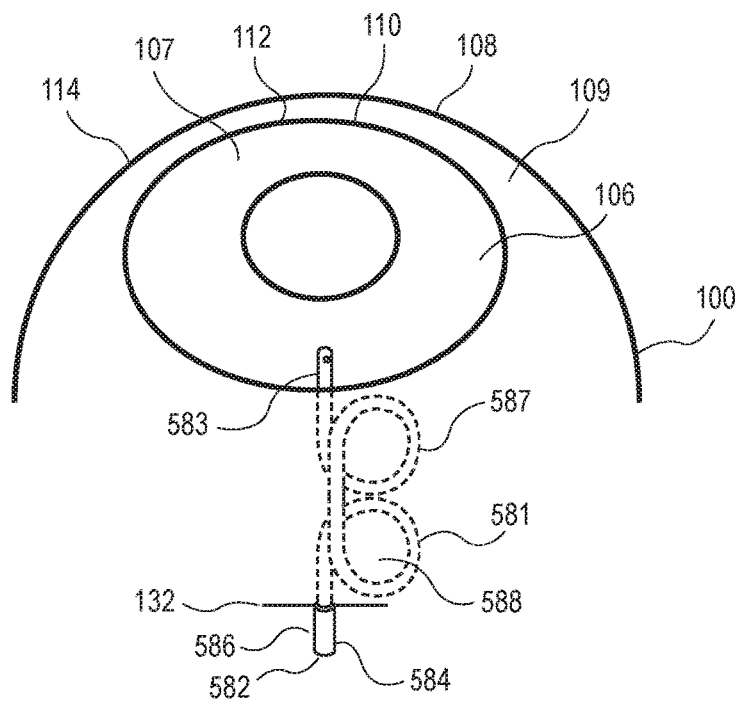
FIG. 36  FIG. 37
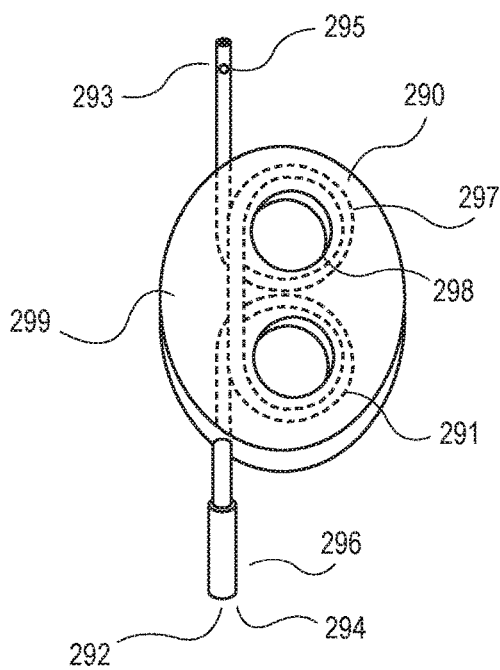
FIG. 38

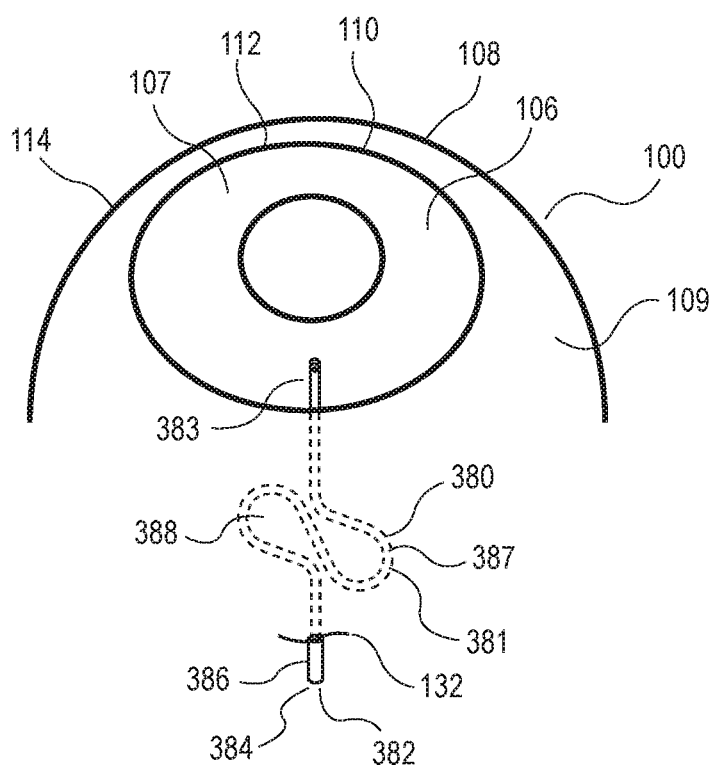
FIG. 41
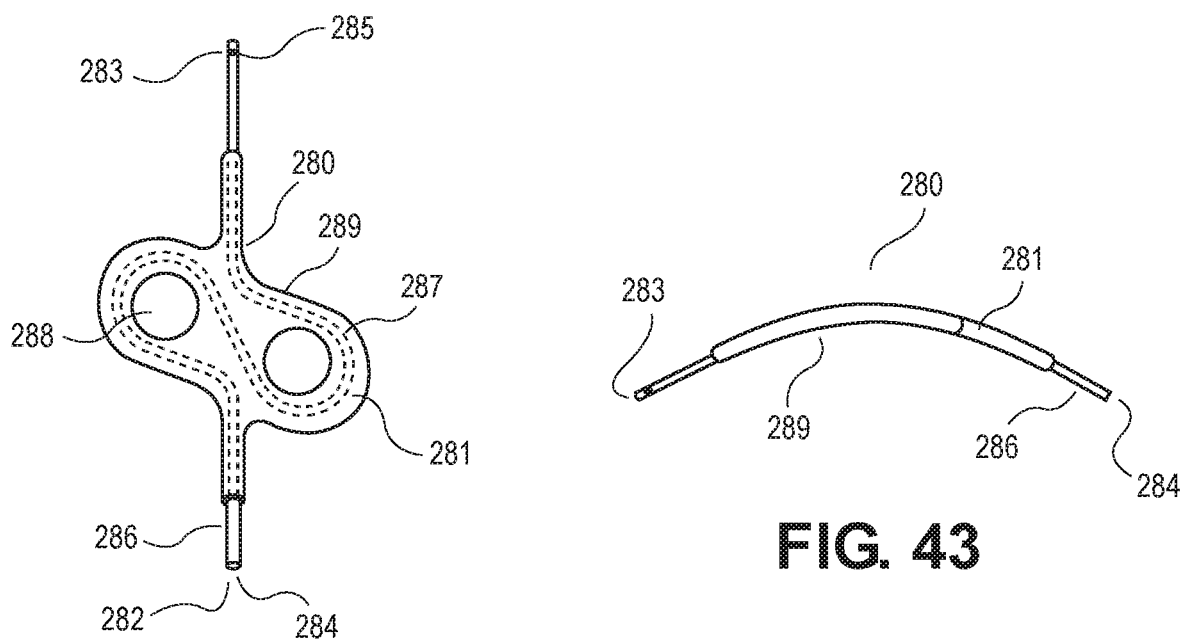
FIG. 42
FIG. 43

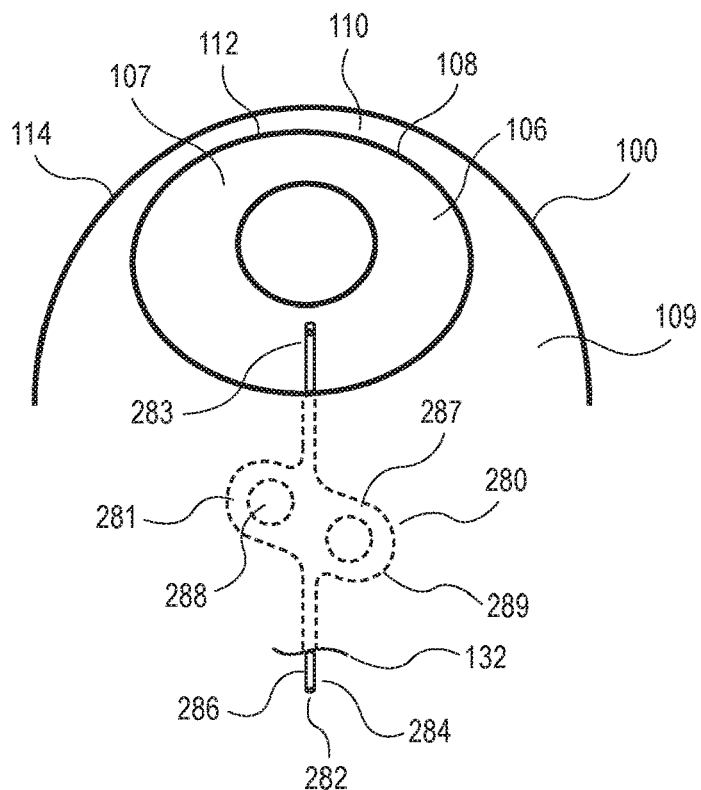
FIG. 44
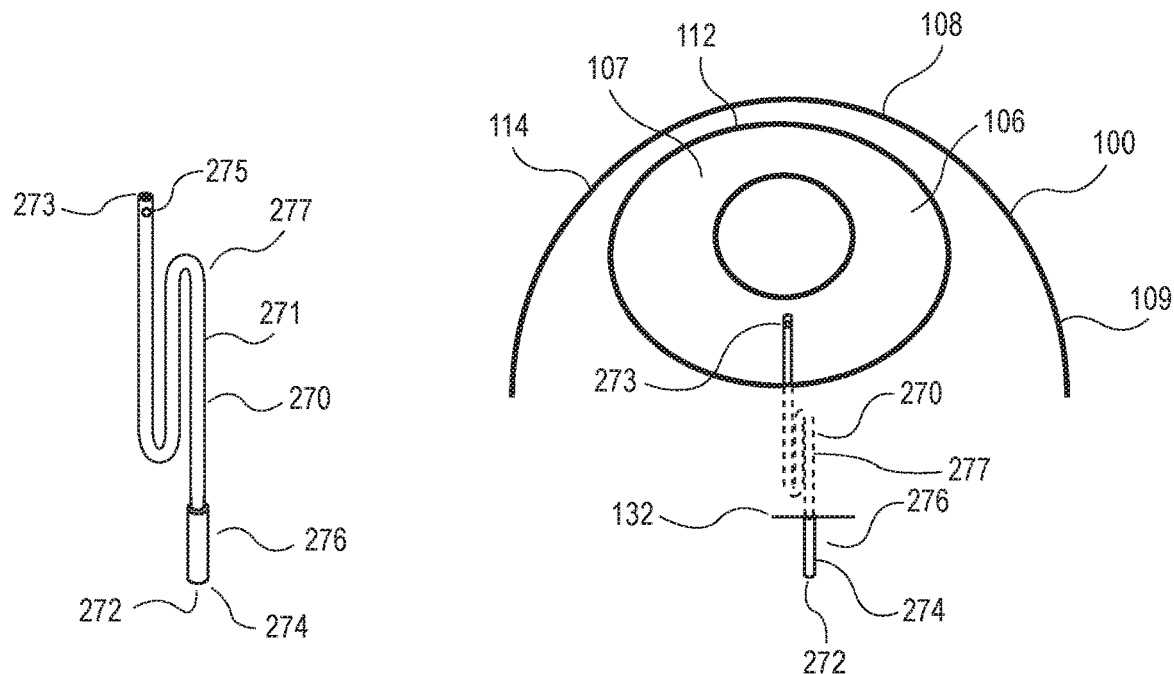
FIG. 45
FIG. 46

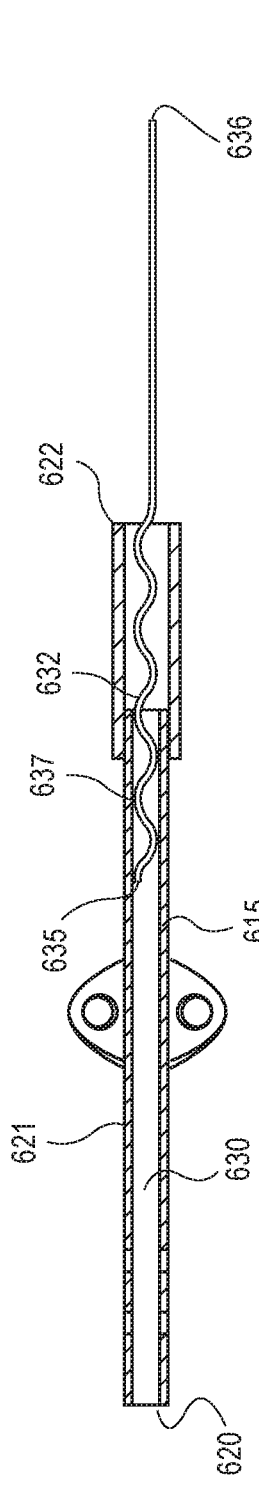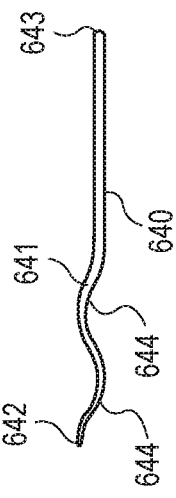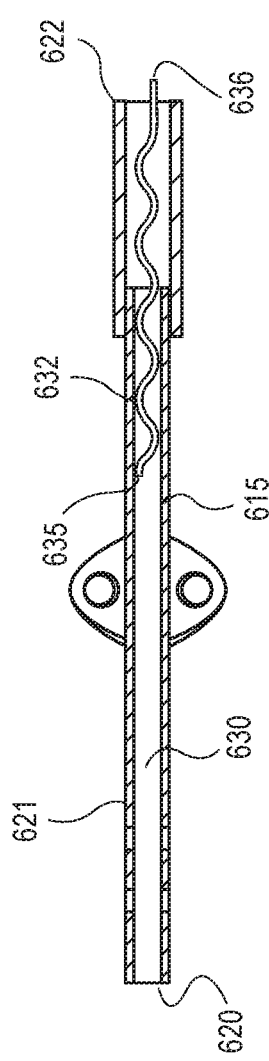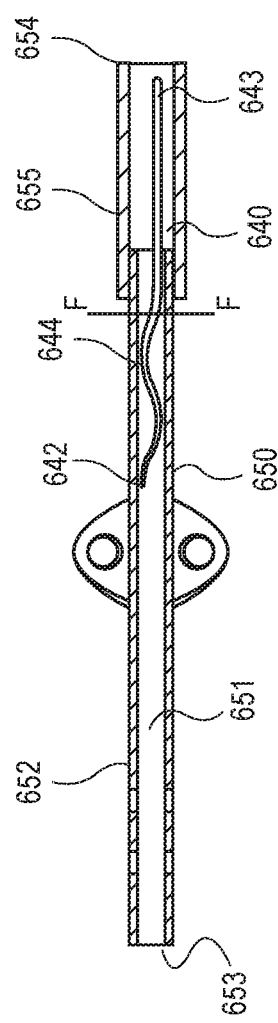

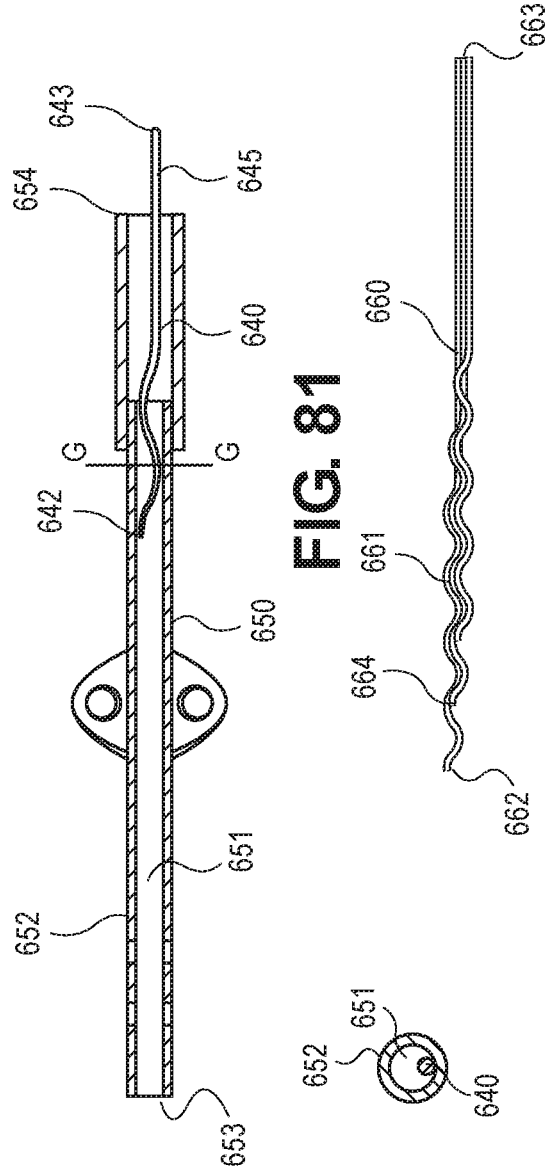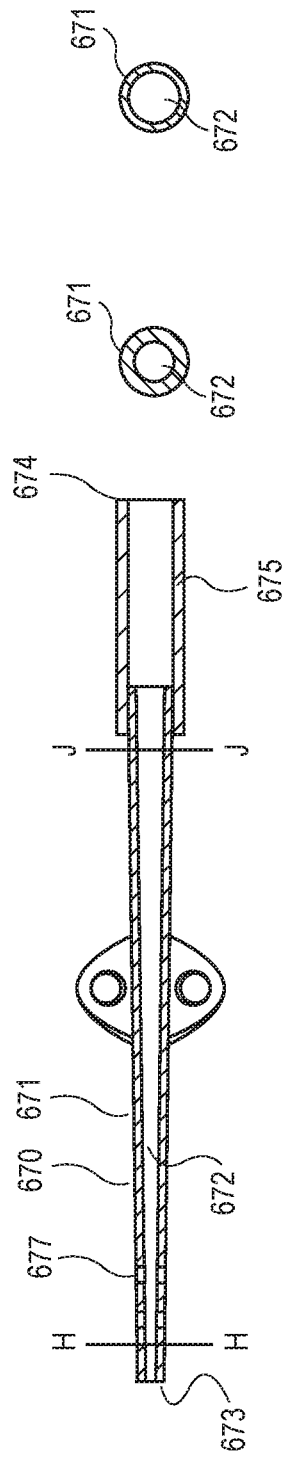

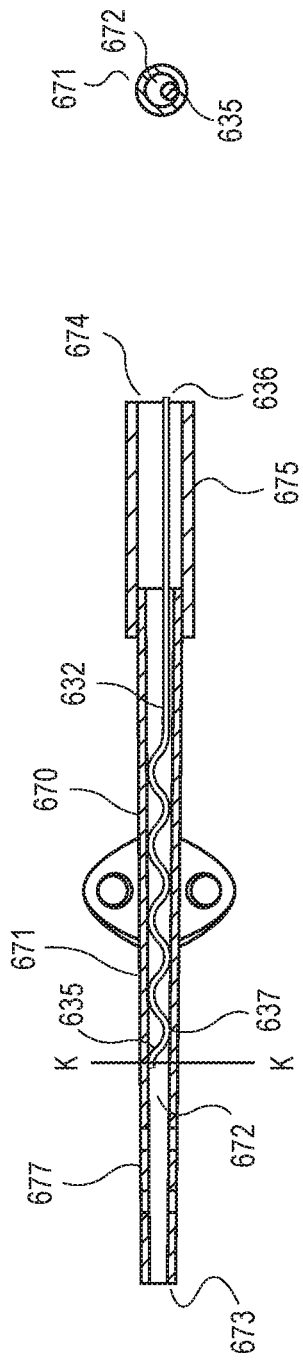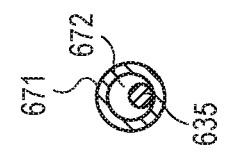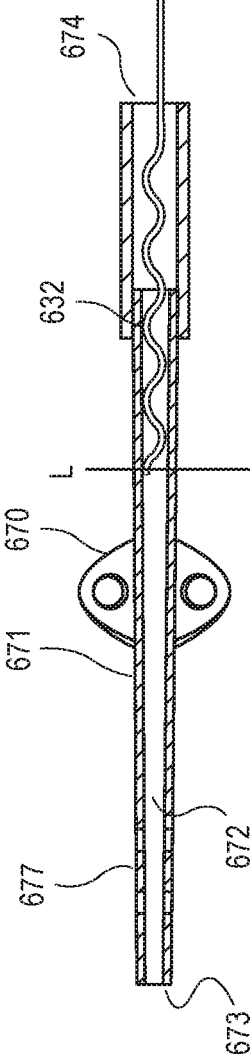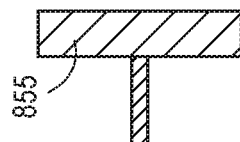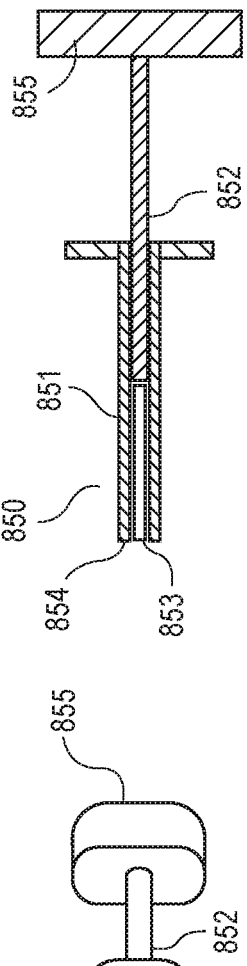

OCULAR DEVICE AND METHOD FOR GLAUCOMA TREATMENT

FIELD OF THE INVENTION

The present invention relates to an ocular drain to relieve intraocular pressure of the eye. More specifically, the present invention relates to an implantable ocular device and related method, which regulates drainage of aqueous humor from the eye. In addition, this invention also provides tools and methods to clean the device non-invasively after implantation if the cleaning becomes necessary.

BACKGROUND OF THE INVENTION

Glaucoma, a condition caused by optic nerve cell degeneration, is the leading cause of irreversible blindness in the world. It is estimated that 67 million people worldwide have glaucoma. About 6 million people are blind from this disease. In the United States, 2.3-3.0 million patients suffer from glaucoma. Elevated intraocular pressure (IOP) is the major risk factor for the progression of glaucoma disease. It is caused by the high resistance to the drainage of the aqueous humor relative to its production. If it is left untreated, an elevated IOP causes irreversible damage to the optic nerve and retinal fibers resulting in a progressive, permanent loss of vision.

Accordingly, treatment of glaucoma has been focused on lowering the intraocular pressure in the affected eye to protect the optic nerve and preserve visual function. Various methods, such as medicines or surgery, have been used for glaucoma treatment. As the first-line treatment, medicines, such as beta-adrenergic antagonists and alpha-adrenergic agonists are usually tried. However, these medicines have proven only moderately effective, and can lead to many side effects, such as red eyes, dry eyes, respiratory and cardiac side-effects. As a consequence, the compliance rate for patients who take medicines is low.

If medicine treatment is either not effective or not tolerated, argon laser trabeculoplasty (ALT) or selective laser trabeculoplasty is usually the next treatment method. For laser trabeculoplasty, an ophthalmologist uses a laser that creates tiny holes in the filtration site of the eye to increase outflow of aqueous humor. However, the success of laser trabeculoplasty is often limited, and is usually temporary. Patients may need to be re-treated multiple times The last therapeutic method involves surgery. Trabeculectomy is a very invasive surgical procedure and is one of the most common types of surgery done for treatment of glaucoma. In a trabeculectomy, a channel is opened in the eye near the limbus or trabecular meshwork, into the anterior chamber, and extended under an overlying scleral flap. The aqueous humor therefore is allowed to drain into the subconjunctival space. Subsequent wound healing circumscribes this subconjunctival drainage area into a bleb. Sometimes, the healing progresses to completely close the bleb, and thereby stopping the flow of aqueous humor and causing the surgery to fail. Anti-mitolic drugs such as Mitomycin C, 5-Fluorouracil, anti-VEGF, have been used to limit scarring to trabeculectomy. While increasing surgical success, however, the use of these drugs has significantly added to the risks and complications of this surgery. Mitomycin C causes thinning of the conjunctiva and may lead to leaking through the weakened conjunctiva, and such leaking often leads to hypotony (low intraocular pressure) and intraocular infection.

Accordingly, a need exists for an ophthalmic implant that can provide controlled anterior chamber drainage without hypotony or clogging while limiting ingress of microorganisms into the anterior chamber. The device and methods disclosed herein overcome one or more of the deficiencies of the prior art. In another embodiment of this invention, the aqueous humor flow resistance of the device is adjustable non-invasively after implantation to achieve the desired IOP. This invention also provides tools and methods to clean the device non-invasively after implantation if the cleaning becomes necessary.

SUMMARY OF THE INVENTION

It is an object of the invention to provide a new ocular device which may be implanted into the eye to treat glaucoma and relieve excess intraocular pressure (IOP) that overcomes the disadvantages of conventional treatment at least to some extent.

An aspect of the invention pertains to an ocular device. The ocular device includes a first end, a second end, and a body. The first end is configured to seat in an anterior chamber of an eye. The first end includes an inlet configured to facilitate an ingress of aqueous humor into the ocular device. The second end is configured to seat in a tear film of the eye. The second end includes an outlet configured to facilitate release a flow of the aqueous humor into the tear film. The body is defined by a fluid conduit. The body includes a lumen having a lumen length and a lumen cross sectional area. The lumen length and the lumen cross sectional area are configured to control an intraocular pressure (IOP) of the eye by controlling the flow of the aqueous humor through the lumen.

Another aspect of the invention relates to a method for treating a patient having glaucoma. The method includes the steps of measuring a pre-operative intraocular pressure (IOP) in an eye of the patient, implanting an ocular device into the eye, and measuring a post-operative IOP to confirm treatment of the patient. The ocular device includes a first end, a second end, and a body. The first end is configured to seat in an anterior chamber of an eye. The first end includes an inlet configured to facilitate an ingress of aqueous humor into the ocular device. The second end is configured to seat in a tear film of the eye. The second end includes an outlet configured to facilitate release a flow of the aqueous humor into the tear film. The body is defined by a fluid conduit. The body includes a lumen having a lumen length and a lumen cross sectional area. The lumen length and the lumen cross sectional area are configured to control an intraocular pressure (IOP) of the eye by controlling the flow of the aqueous humor through the lumen. At least one of the lumen length and the lumen cross sectional area is selected in response to the measured pre-operative IOP.

In one or more embodiments of this invention, the ocular device comprises a body defining a fluid conduit with a distal end and a proximal end to allow the aqueous humor to flow from the distal end to the proximal end. The proximal end comprises a compliant tube that is configured to protrude out of the exterior surface of the eyeball through an incision on the eyeball. The compliant tube is flexible to comply with eyelid movement or collapsible under pressure from the eyelid without affecting aqueous humor draining efficiency. The compliant tube is also configured to minimize its profile on the surface of the eye, and thereby preventing irritation to the eyelids or eye. In addition, the protruding compliant tube can maintain the aqueous humor flow patency of the compliant tube by prevent tissue ingrowth in the tube. The distal end of the ocular device is configured to seat in the anterior chamber. The fluid conduit is sized to relieve IOP of the eye by draining aqueous humor from the anterior chamber to the tear film of the eye in a controlled manner.

In another embodiment of this invention, the fluid conduit comprises a length to provide fluid communication between the anterior chamber and the tear film to drain the aqueous humor, thereby achieving normal IOP when the ocular device is implanted in the cornea, limbus, sclera or conjunctiva. The fluid conduit also includes a length to provide sufficient flow resistance to avoid hypotony without using a filter, a valve or a narrow conduit. In addition, the fluid conduit also comprises a sufficient size (e.g. diameter or cross-sectional area) to prevent clogging from debris in the aqueous humor.

In another embodiment of this invention, the ocular device provides a method to impede the transmission of microorganisms into the anterior chamber without using a filter, a valve or a narrow conduit. The fluid conduit of the device comprises a sufficient length to prevent bacteria from migrating against the aqueous humor flow, and thereby gaining entry into the anterior chamber through the fluid conduit. In addition, the surface of the fluid conduit comprises an antimicrobial material to prevent bacteria from migrating into the anterior chamber through the fluid conduit. Because the antimicrobial effectiveness of this antimicrobial surface is proportional to its surface area, the increase in conduit length and surface roughness can increase the antimicrobial surface area and the conduit's efficiency for impeding the transmission of microorganisms into the anterior chamber. The antimicrobial material comprises material such as metals, metal ion, metal oxide, metal compound, silver, silver oxide, silver nitrate, silver compound, silver nanoparticles, copper, zinc, and platinum, etc. Alternatively, the ocular device is made by the antimicrobial material. In addition, the antimicrobial surface of the fluid conduit also prevents debris or deposits build-up in the fluid pathway.

In one embodiment of this invention, the surface of the fluid conduit comprises an antifouling material to prevent bacteria from migrating into the anterior chamber through the fluid conduit. The antifouling material comprises material such as: poly ethylene glycol, poly ethylene glycol copolymers, poly propylene glycol, hydrogel, poly (vinyl alcohol), poly (2-hydroxyethyl methacrylate) (PHEMA), crosslinked PEG diacrylate, Zwitterionic compound, poly carboxybetaine methacrylate, etc. Alternatively, the ocular device is made by the antifouling material. In addition, the antifouling surface of the fluid conduit can also prevent debris or deposits build-up in the fluid pathway.

In another aspect, this invention features design that allows the device to be cleaned non-invasively and methods to clean the ocular device that is already implanted in an eye. The IOP control system comprises an implanted ocular device and a cleaning tool. The entire fluid conduit of the implanted ocular device can be easily accessed by the cleaning tool because the proximal end of the device is in the tear film and there is no filter or valve in the conduit. A clinician can use the cleaning tool to clean the implanted ocular device non-invasively from the exterior of the eye. By being able to clean the debris and tissue build-up on the device non-invasively, and returning functionality to the ocular device, this invention may result in an ocular device with a longer useful life, reducing the likelihood that a replacement device may be needed for glaucoma patients.

In one embodiment of this invention, the ocular device further comprises a plurality of retainers or suture holes configured to increase the fixation of the device in the eye when the device is implanted in the eye.

In another embodiment of this invention, the distal end of the ocular device further comprises a plurality of openings and points away from the angle of the anterior chamber and the trabecular meshwork when the device is implanted in the anterior chamber. This can reduce the chance for tissue ingrowth into the fluid conduit and the clogging of the device.

In another embodiment of this invention, this ocular device is surgically implanted in the eye with the compliant tube seated on the tear film. Alternatively, the compliant tube is seated on the external surface of the sclera. Alternatively, the compliant tube is seated on the external surface of the cornea. In yet another embodiment of this invention, the compliant tube is seated on the external surface of the conjunctiva.

In yet another embodiment of this invention, the exterior surface of the ocular device is configured to promote tissue growth or tissue integration with the eye. The tissue growth or tissue integration can increase the fixation of the device at the implant site and eliminate potential dead space around the device.

In another embodiment of this invention, the geometry (i.e. length, size) of the fluid conduit provides outflow resistance to aqueous humor and determine the IOP of the eye without using a valve, a filter or a narrowing in the fluid conduit. After the ocular device is implanted in the eye, the IOP in the eye is relieved by draining aqueous humor from the anterior chamber to the tear film of the eye in a controlled manner determined by the geometry of the fluid conduit. A minimal IOP can be maintained by using appropriate fluid conduit geometry to avoid hypotony in the eye without the need to use a valve, a filter or a narrow section in the conduit. A longer fluid conduit is allowed to have a larger conduit size, while maintaining sufficient flow resistance to avoid hypotony. Larger conduit size is advantageous in avoiding clogging caused by the debris in the aqueous humor. In addition, longer fluid conduit also makes it more difficult for the bacteria to migrate against the aqueous humor outflow into the anterior chamber through the conduit. The increased antimicrobial surface included in the long fluid conduit can also impede bacteria from moving into the anterior chamber through the fluid conduit. In this invention, the geometry of the fluid conduit is configured to provide outflow resistance to avoid hypotony in the eye without using a filter, a valve or a narrow conduit, and at the same time preventing clogging and bacteria migrating into the anterior chamber.

In one embodiment of this invention, several methods are used to minimum the exposure of the ocular device in the visual field, and thereby preventing the ocular device from interfering the patients' field of vision after the device is implanted in the patients. The ocular device can be implanted circumferentially around the outer perimeter of the anterior chamber in the eye. Alternatively, the device can be implanted circumferentially around the inner perimeter of the anterior chamber (above or below the iris) without blocking the iris or the trabecular meshwork. In addition, increased surface roughness and tortuosity in the fluid conduit can increase the flow resistance of the device, and therefore a shorter fluid conduit (with less chance to interfere the patients' field of vision) is needed to prevent hypotony.

In further another embodiment of this invention, the flow resistance of the ocular device and the IOP of the eye is regulated by the surface roughness of the fluid conduit. A rough conduit surface can increase the friction between the aqueous humor and the conduit surface, thereby increasing the flow resistance of the device. The ocular device with a rougher conduit surface and a higher flow resistance can yield a higher IOP comparable to an ocular device with a smoother conduit surface. In addition, the rougher conduit surface comprises a larger antimicrobial surface area, thereby impeding bacteria from migrating into the anterior chamber through the fluid conduit. In this invention, the surface of the fluid conduit is configured to provide sufficient outflow resistance to avoid hypotony in the eye without using a filter, a valve or a narrow conduit, and simultaneously prevent clogging and bacteria from migrating into the anterior chamber. The surface roughness of the fluid conduit also maintains the flow resistance of the conduit to avoid the hypotony with a shorter conduit length, and thereby reducing the risk of interfering with patient's field of vision.

In yet another embodiment of this invention, the flow resistance of the ocular device and the IOP of the eye can be regulated by the tortuosity of the fluid conduit. The tortuous fluid conduit increases total conduit length and creates turbulent flow in the fluid conduit, thereby increasing the flow resistance of the device. The increase in flow resistance is proportional to the tortuosity of the fluid conduit. The more tortuous the fluid conduit, the higher the flow resistance. As a result, the ocular device with a tortuous conduit can yield a higher IOP in the eye compared to an ocular device with a straight conduit. In this invention, the device is provided with sufficient tortuosity with sufficient outflow resistance to avoid hypotony in the eye without using a filter, a valve or a narrow conduit, and simultaneously prevent clogging and bacteria migrating into the anterior chamber. The tortuosity of the device also increases the total length of the conduit without increasing the linear distance between the proximal end and distal end of the device, and thereby reducing the risk of interfering with patient's field of vision.

In yet another embodiment of this invention, the flow resistance of the ocular device and the IOP of the eye can be regulated by an adjustable flow restrictor in the fluid conduit. The adjustable flow restrictor is configured to seat in the fluid conduit and restrict the aqueous humor flow rate in the fluid conduit and cause turbulent flow, thereby increasing the flow resistance and pressure drop between the two ends of the fluid conduit. The increase in flow resistance and IOP is proportional to the length and size (cross-sectional area) of the adjustable flow restrictor in the fluid conduit. The longer and larger the flow restrictor in the fluid conduit, the higher the flow resistance and the IOP in the eye. In one embodiment of this invention, the adjustable flow restrictor further comprises an antimicrobial material, thereby impeding bacteria from migrating into the anterior chamber through the fluid conduit. In another embodiment of this invention, the proximal end of the adjustable flow restrictor is accessible from the exterior of the eye and the IOP can be adjusted without invasive surgery. In yet another embodiment of this invention, the adjustable flow restrictor is capable of increasing the flow resistance of the device and the IOP in the eye. Alternatively, the adjustable flow restrictor is capable of decreasing the flow resistance of the device and the IOP in the eye. Alternatively, the adjustable flow restrictor is tapered along the length of the restrictor.

In this invention, a normal IOP in the eye can be maintained by selecting the ocular device with appropriate fluid conduit geometry (e.g. diameter, length, tortuosity, etc.) for the treatment. However, if adjustment of IOP is desired after implantation, the ocular device of this invention is configured to allow easy and non-invasive adjustment of IOP to achieve the desired IOP. Furthermore, the adjustment mechanism of this invention is capable of changing the aqueous humor outflow from a lower flow rate to a higher flow rate, or vis versa.

In yet another embodiment of this invention, the ocular device comprises material selected from the group consisting of polymer, silicone, polydimethylsiloxane, silastic, poly 2-hydroxyethylmethacrylate (PHEMA), poly hydroxyethyl methacrylate-methacrylic acid copolymer (polyHEMA-MAA), polymethylmethacrylate (PMMA), silicone/hydrogel combinations, silicone acrylic combinations, fluorosilicone acrylates, acrylic, polyimide, polyethylene, polyethersulfone, polysulfone, hydrogel, polyolefin, polyvinylchloride, polypropylene, polyester, polytetrafluoroethylene (PTFE), expanded polytetrafluoroethylene (ePTFE), polyvinylidene fluoride, polyvinylidene difluoride, regenerated cellulose, cellulose ester, cellulose, polycarbonate, antimicrobial material, antimicrobial material/polymer composites, antimicrobial material/silicone composites, ceramic, glass, stainless steel, metal, metal ion, metal oxide, metal compound, silver, silver oxide, silver nitrate, silver compound, silver nanoparticles, gold, copper, zinc, platinum, titanium, shape memory material, Nitinol, etc.

In one embodiment of this invention, the method to deploy the ocular device in the eye to treat glaucoma is provided. The ocular device can be inserted through the cornea, limbus, conjunctiva or sclera of the eye into the anterior chamber to drain aqueous humor into the tear film of the eyeball. The implantation procedure requires the creation of an incision at the implantation site without affecting the patient's field of vision. Then the hypotube of the delivery system is inserted into the anterior chamber through the incision, and the ocular device in the hypotube is pushed out from the distal end of the hypotube. After the ocular device is deployed, the delivery system is pulled away from the anterior chamber. At the same time, the ocular device resiliently regains its original shape without blocking the iris or the trabecular meshwork.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DESCRIPTION OF DRAWINGS

FIG. 36 is a perspective view of a tortuous ocular device described in another embodiment of this disclosure.

FIG. 37 is a perspective view of an eye showing the cornea, sclera, and iris with the implanted ocular device according to FIG. 36.

FIG. 38 is a perspective view of the ocular device according to FIG. 36 with a coating or an encapsulation on the device.

FIG. 41 is a perspective view of an eye showing the cornea, sclera, and iris with the implanted ocular device according to FIG. 40.

FIG. 42 is a perspective view of the ocular device according to FIG. 40 with a coating or an encapsulation on the device.

FIG. 43 is a side view of the ocular device according to FIG. 42 with a coating or an encapsulation on the device.

FIG. 44 is a perspective view of an eye showing the cornea, sclera, and iris with the implanted ocular device according to FIG. 42.

FIG. 45 is a perspective view of a tortuous ocular device described in another embodiment of this disclosure.

FIG. 46 is a perspective view of an eye showing the cornea, sclera, and iris with the implanted ocular device according to FIG. 45.

FIG. 76 is a cross-sectional view of the ocular device according to FIG. 74 with portion of the adjustable flow restrictor pulled out from its fluid conduit.

FIG. 77 is a cross-sectional view of the ocular device according to FIG. 74 with portion of the adjustable flow restrictor trimmed.

FIG. 78 is a perspective view of an adjustable flow restrictor described in another embodiment of this disclosure.

FIG. 79 is a cross-sectional view of an ocular device with the adjustable flow restrictor according to FIG. 78 in its fluid conduit.

FIG. 80 is a cross-sectional view of the ocular device (along Line FF) according to FIG. 79 with the adjustable flow restrictor in its fluid conduit.

FIG. 81 is a cross-sectional view of the ocular device according to FIG. 54 with portion of the adjustable flow restrictor pulled out from its fluid conduit.

FIG. 82 is a cross-sectional view of the ocular device (along Line GG) according to FIG. 81 with the adjustable flow restrictor in its fluid conduit.

FIG. 83 is a perspective view of an adjustable flow restrictor with wire bundle described in another embodiment of this disclosure.

FIG. 84 is a cross-sectional view of the ocular device with a tapered conduit described in another embodiment of this disclosure.

FIG. 85 is a cross-sectional view (along Line HH) of the ocular device with a tapered conduit according to FIG. 83.

FIG. 86 is a cross-sectional view (along Line JJ) of the ocular device with a tapered conduit according to FIG. 83.

FIG. 87 is a cross-sectional view of the ocular device with an adjustable flow restrictor in the tapered conduit.

FIG. 88 is a cross-sectional view (along Line KK) of the ocular device with an adjustable flow restrictor in the tapered conduit.

FIG. 89 is a cross-sectional view of the ocular device with a partially pulled out adjustable flow restrictor in the tapered conduit.

FIG. 90 is a cross-sectional view (along Line LL) of the ocular device with a partially pulled out adjustable flow restrictor in the tapered conduit.

FIG. 91 is an external view of the ocular device delivery system with an elongated hypotube described in one embodiment of this disclosure.

FIG. 92 is a cross-sectional view of the ocular device delivery system according to FIG. 91 with the ocular device in its hypotube.

DETAILED DESCRIPTION

Figure 1:
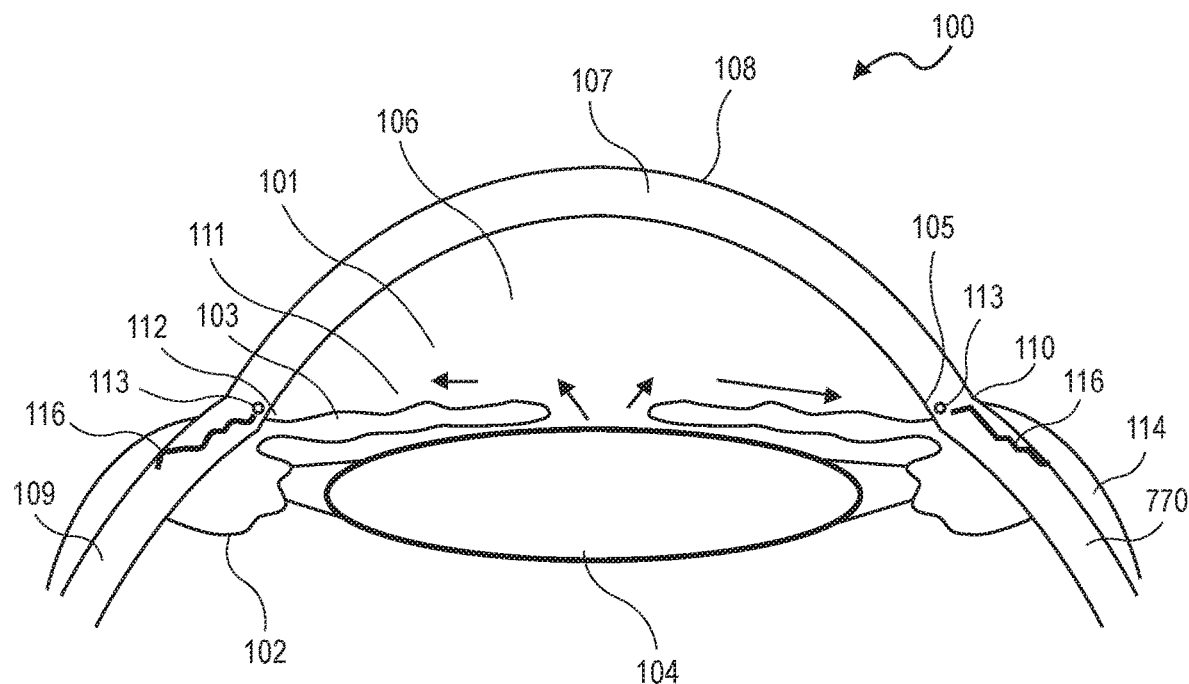
FIG. 1 is a cross-sectional view of the anterior segment of an eye showing the cornea, sclera, and conjunctiva.

FIG. 1 is a cross section view of the anterior segment 101 of an eye 100. The anterior segment 101 of the eye 100 comprises structure that can cause elevated IOP which may lead to glaucoma. Aqueous humor fluid is produced by the ciliary body 102 which lies beneath the iris 103 and adjacent to the lens 104 in the anterior segment 101 of the eye 100. This aqueous humor flows on top of the lens 104, iris 103 and then flows to the drainage system located in the angle 105 of the anterior chamber 106. The angle 105 of the anterior chamber 106, which extends circumferentially around the anterior chamber 106, comprises trabecular meshwork 112 that allows the aqueous humor to drain. The trabecular meshwork also extends circumferentially around the anterior chamber 106. The trabecular meshwork acts as a filter, limiting the outflow of aqueous humor and providing a back pressure that directly relates to IOP of the eye 100. Schlemm's canal 113 is located beyond the trabecular meshwork 112. Schlemm's canal is connected to collector channels 116 allowing aqueous humor to flow out of the anterior chamber 106 into the collector channels 116 and then the venous circulation system. As is shown in FIG. 1, the dome-shaped cornea 107 covers the front of the eye 100. Every time eye blinks, tears film 108 is distributed across the eye 100 to keep the eye 100 moist and protect against infection. The sclera 109 surrounds the cornea 107. The junction between the sclera 109 and the cornea 107 is called the limbus 110. The conjunctiva 114 is a thin layer of tissue covering the sclera 109.

Some ophthalmic implants are surgically implanted in the eye 100 and used to drain aqueous humor into a conjunctive 114 bleb over the sclera 109, into a suprachoroidal space 770, or into a space in the eye 100. The ophthalmic implants are surgically inserted into the eye 100 during a trabeculectomy to provide a conduit for the outflow of aqueous humor and reduce eye pressure. Because both ends of the ophthalmic implants are in the eye, there is less concern for bacteria ingress from the draining site into the eye through the conduit. The bleb or eye tissue at the draining site also provide back pressure to prevent hypotony (low intraocular pressure). However, the surgical procedures for such ophthalmic implants are invasive with numerous issues. One of the issues associated with such implants is the regulation of aqueous humor outflow. For those implants, the back pressure and the drainage rate of the aqueous humor depends substantially on both the characteristics of the implants and the wound healing at the draining sites, such as the conjunctive 114 or suprachoroidal space 770. However, wound healing is difficult to control and the resulting draining space and device draining efficiency is hard to predict. Some implants use larger fluid conduits to mitigate the potential flow rate reduction due to the wound healing. However, this approach increases the risk for hypotony before the wound healing is completed and the draining space is stable. As a consequence, a variety of mechanical mechanisms, such as valve, filter, temporary ligature and plug, have been used in the implants to control the initial aqueous outflow after implantation to avoid hypotony. However, effective control of aqueous humor outflow remains a problem for these types of drainage implant. As a consequence, a high failure rate was observed after the surgery. Several of these drainage implants are described in Patent Application No. US2004/0260227A1, US2005/0277864A1, US2007/0156079A1, US2010/0249691A1, US2016/0287439A1; and U.S. Pat. Nos. 3,788,327A, 4,402,681A, 4,554,918A, 4,634,418A, 5,626,559A, 5,702,414A, 5,743,868A, 5,807,302A, 6,077,299A, 6,186,974B1, 6,699,210B2, 7,431,709B2, 7,780,623B2, 8,617,139B2, 8,888,734B2, 9,283,115B2, 9,375,347B2, 9,681,983B2. The entire content of which is incorporated herein by reference.

Various attempts have been made to overcome the issues and reduce the complications of ophthalmic implants surgery discussed in the previous sections. One of the solutions is the use of an implant to reduce the intraocular pressure in the eye by draining aqueous humor from the anterior chamber 106 directly to the tear film 108 of the eye. Because there is no conjunctival 114 bleb or suprachoroidal 770 drainage space created in the eye 100, the issues associated with the conjunctival 114 bleb and wound healing at the aqueous humor draining sites are thus avoided. In addition, this type of implant typically involves less invasive surgical procedures during the implantation of the device and is faster than other surgical options because its approximation to the exterior of the eye 100. Several of these implants are described in Patent Application No. US2007/0156079A1, US2010/0056977A1, US2016/0058615A1, US2016/0058616A1, US2017/0087016A1, WO2018009556A1, WO2017059272A1; and U.S. Pat. Nos. 4,402,681A, 5,300,020A, 5,326,345A, 5,346,464A, 5,743,868A, 5,807,302A, 6,595,945B2, 6,881,198, 7,641,627B2, 9,125,723B2, 9,186,274B2. The entire content of which is incorporated herein by reference.

However, these proposed implants are also subject to some difficulties. Draining aqueous humor from the anterior chamber 106 directly into the tear film 108 means the aqueous humor outflow has to be controlled to avoid hypotony because there is no conjunctival 114 bleb or suprachoroidal space 770 to provide sufficient back pressure. The pressure regulation mechanisms such as filter, valve, narrowing (which function similarly to the filter) in the flow conduits are usually used in those types of implants. Additionally, the presence of an implant provides a conduit through which bacteria from the tear film 118 may gain entry to the anterior chamber 106, thereby resulting in intraocular infections. The filter, valve or narrowing in the fluid conduit may also serve to impede the transmission of microorganisms into the anterior chamber 106. However, these pressure regulation mechanisms have their limitations. Even though they may be effective in impeding the transmission of microorganisms and regulating aqueous humor flow, they also tend to clog over time. The clogging is caused by either the debris or tissue inside the eye. They may accumulate or build-up in the pressure regulation mechanisms or in the fluid conduit. Over time, these debris and tissue deposits may eventually decrease the flow capacity and effectiveness of the implant as a treatment for elevated IOP.

It is an object of the invention to provide a new ocular device which may be implanted into the eye to treat glaucoma and relieve intraocular pressure (IOP) by draining the aqueous humor from the anterior chamber 106 of the eye 100 to the tear film 108 in a controlled manner to avoid hypotony, clogging and microorganisms transmission into the anterior chamber 106 without using a filter, a valve or a narrowing in the fluid conduit. In one embodiment of this invention, the ocular device bypasses the flow-resistive conventional pathway through the trabecular meshwork 112 and permits drainage of aqueous humor from the anterior chamber 106 directly into the tear film 108 of the eye 100 to alleviate elevated intraocular pressure without blocking the trabecular meshwork 112 or interfering the patients' field of vision when the ocular device is implanted in the cornea 107, limbus 110, conjunctiva 114 or sclera 109.

In another aspect, this invention features method for cleaning and removing clogging in the ocular device when the device is still implanted in the eye 100. In this invention, the proximal end of the device is seated on the exterior of the eyeball 100. The entire fluid conduit of the ocular device disclosed herein is configured to allow easy access by the cleaning tool without invasive surgery because there is no filter, valve or narrow section in the fluid conduit. The cleaning tool removes any tissue build up that may impede aqueous flow or proper operation of the ocular device. By being able to clean the debris and tissue build-up on the implanted ocular device, and returning functionality to the ocular device, this invention may result in an ocular device with a longer useful life, reducing the likelihood that a replacement device may be needed.

The ocular device provided herein has numerous advantages. First, the ocular device can reduce the intraocular pressure (IOP) in the eye 100 by draining aqueous humor from the anterior chamber 106 directly into the tear film 108 of the eye 100 with known back pressure (i.e. one atmosphere pressure). As a consequence, the fluid conduit geometry (i.e. length, lumen size, tortuosity) and surface roughness may be configured to provide aqueous humor outflow resistance that yields desirable intraocular pressure to avoid hypotony without the need for clog prone pressure regulation mechanism such as valve, narrowing or filter. In particular, the fluid conduit comprises a geometry (i.e. length, lumen size, tortuosity) and surface roughness to provide sufficient aqueous humor flow resistance to avoid hypotony without blocking the trabecular meshwork or interfering the patients' field of vision after the ocular device is implanted in the eye 100, and simultaneously impeding the bacteria from migrating into the eye 100 through the fluid conduit. Because the ocular device comprises a fluid conduit with a fixed or enlarged lumen size with no flow obstructive pressure regulation mechanism such as valve, narrowing or filter in the fluid conduit, there is little chance for the ocular device to clog. However, even if there is a clog in the fluid conduit, the proximal end of the ocular device is positioned on the tear film 108 with easy access, and there is no flow obstructive pressure regulation mechanism in the fluid conduit. Those configurations allow the ocular device to be cleaned non-invasively by a cleaning tool when the ocular device is still implanted in the eye 100. In addition, the ocular device comprises a compliant tube positioned on the tear film 108 to enable the draining of aqueous humor into the tear film 108 without irritating the eye 100 or eyelid. This compliant tube is configured to be flexible to comply with eyelid movement or collapsible under pressure from either the eyelid or the hand. The compliant tube also comprises a surface or coating that prevents tissue or cell attachment. Second, the ocular device can drain aqueous humor from the anterior chamber 106 directly to the tear film 108, rather than into the subconjunctival 114, suprachoroidal space 770 or any other place in the eye 100. This can avoid the development of a subconjunctival 114 bleb, and therefore eliminate the side effects associated with the subconjunctival 114 bleb. In addition, draining to the tear film 108 can eliminate the uncertainty in back pressure and drainage efficiency caused by the wound healing around the draining site if the draining site is in the subconjunctival 114, suprachoroidal space 770 or any other place in the eye 100. Third, the ocular device provides way to prevent bacteria from gaining entry into the anterior chamber 106 through the fluid conduit. Fourth, this ocular device can be easily and safely inserted into an eye 100 through a small incision in the cornea 107, limbus 110, sclera 109 or conjunctiva 114. Fifth, the aqueous humor can be expelled to the tear film 108, enhancing moisture and lubrication in the eye 100. Sixth, this ocular device comprises features, such as retainers or suture holes to secure the device in an eye 100. Last, the flow resistance of the ocular device and the resulting IOP in the eye 100 can be easily and safely adjusted after implantation without invasive surgical procedure.

Figure 2:
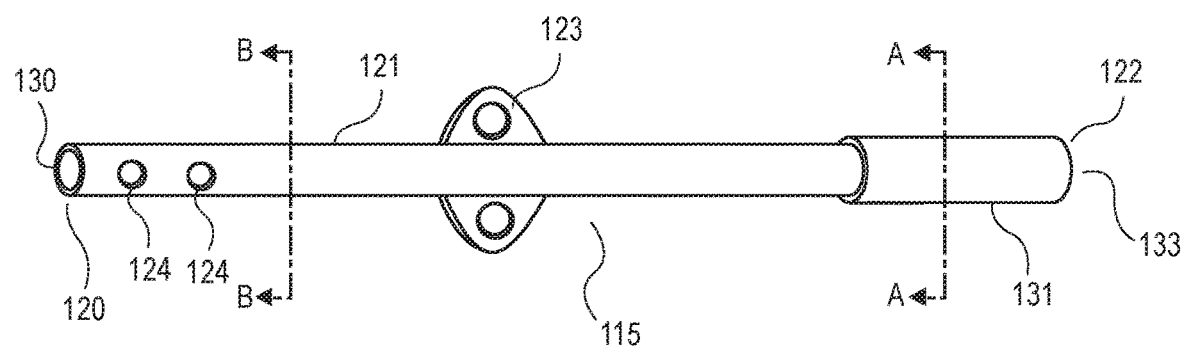
FIG. 2 is a perspective view of the ocular device in one embodiment of this disclosure.
Figure 3:
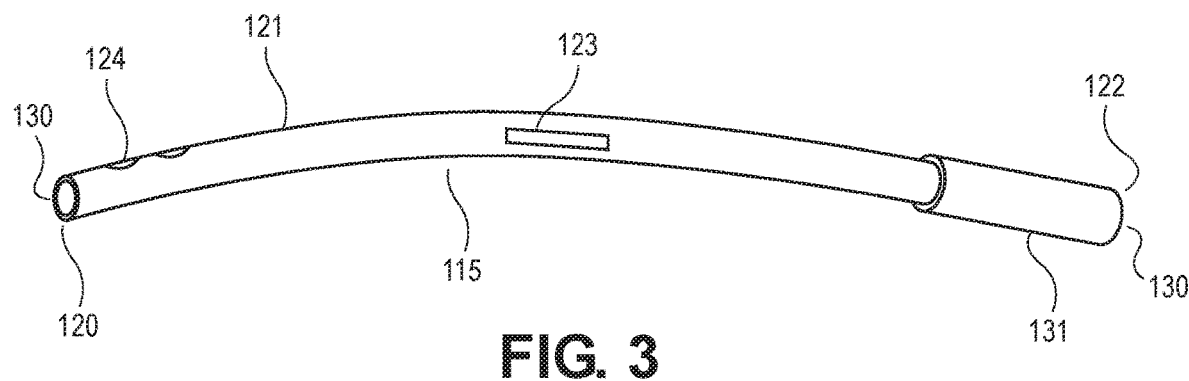
FIG. 3 is a side view of the ocular device according to FIG. 2.
Figure 4:
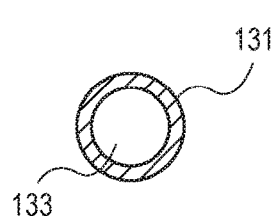
FIG. 4 is a cross-sectional view (along Line AA) of the ocular device according to FIG. 2.
Figure 5:
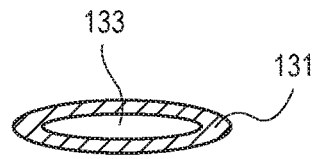
FIG. 5 is a cross-sectional view (along Line AA) of the ocular device according to FIG. 2 when the device is under pressure from the eyelid or hand.
Figure 7:
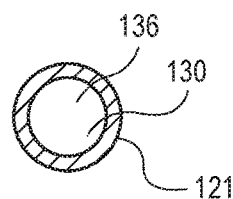
FIG. 7 is a cross-sectional view (along Line BB) of the ocular device according to FIG. 6.

FIG. 2 is a perspective view of an ocular device 115 with a body 121, one or more suture holes 123, a distal end 120 and a proximal end 122 according to an embodiment of the present invention. The distal end 120, the body 121, suture holes 123, and the proximal end 122 of the ocular device 115 may all be formed integrally as a unit. The ocular device 115 is configured with a generally tubular shape without blocking the trabecular meshwork 112 or interfering the patients' field of vision when it is implanted in the eye 100. The tubular-shaped body 121 defines a fluid conduit 130 with a fixed or an expanded lumen size along the fluid conduit 130 that connects the distal end 120 and the proximal end 122. The distal end 120 comprises a plurality of opening 124, thereby reducing the chance for blocking the entrance of the fluid conduit 130 and the clogging of the device 115. The one or more suture holes 123 on the ocular device 115 are configured to receive suture, and thereby increasing the fixation of the device 115 in the eye 100 when it is implanted in the eye 100. The proximal end 122 includes a compliant tube 131. FIG. 7 shows the cross-sectional view of the ocular device 115 along Line BB in FIG. 2. While the lumen 136 of the ocular device 115 comprises round shape, some embodiments of the device 115 can have different shapes and different dimensions that may be accommodated by the eye. For example, the lumen of the ocular device 115 may assume an oval, round, square, rectangular, flat or irregular shape. The compliant tube 131 of the ocular device 115 is configured to protrude out of the external surface of the eye 100 when the ocular device 115 is implanted in the eye 100. FIG. 4 shows the cross-sectional view of the ocular device 115 along Line AA in FIG. 2. As shown in this figure, the cross section of the compliant tube 131 may be round to reduce irritation to the eye 100 and eyelids (not shown). The compliant tube 131 has a thickness between 0.001 mm and 1.0 mm. While this circular shape of the compliant tube 131 appears particularly advantageous in providing comfort to the eye and minimizing foreign body sensation, other shapes may be designed to provide the same advantages. The compliant tube 131 also comprises a lubricious or non-sticky surface or a coating configured to reduce tissue or cell attachment on the compliant tube 131. The compliant tube 131 also includes an enlarged lumen 133 relative to the lumen 136 of the fluid conduit 130. The non-sticky surface and enlarged lumen 133 of the compliant tube 131 is configured to reduce the chance for clogging of the ocular device 115 after implantation and allow easy access for the cleaning tool and IOP adjustment if needed. In another embodiment of this invention, the compliant tube 131 is configured to be flexible to comply with eyelid movement or collapsible under pressure from either the eyelid or the hand. FIG. 5 shows the cross-sectional view of the collapsed compliant tube 131 along Line AA in FIG. 2. The lumen 133 of the collapsed compliant tube 131 remains larger than the lumen 136 of the fluid conduit 130. This configuration allows continuous aqueous humor flow through the collapsed compliant tube 131 with minimum irritation to the eye 100 or eyelid. FIG. 3 is a side view of the ocular device 115 with a curved body 121. The curvature is configured to follow the curvature of the eye 100 when the device 115 is implanted in the eye 100.

Figure 6:
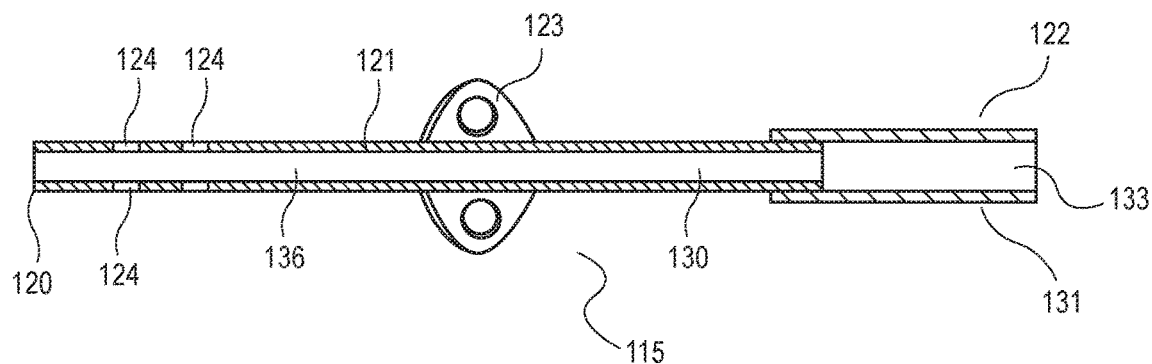
FIG. 6 is a cross-sectional view of the ocular device according to FIG. 2.

FIG. 6 shows the cross-sectional view of the ocular device 115. The ocular device 115 includes the body 121 defining the fluid conduit 130 with the fixed lumen size along the length of the fluid conduit 130, the distal end 120 and the proximal end 122 to allow the aqueous humor to flow from the distal end 120 to the proximal end 122. There is no valve, narrowing or filter in the fluid conduit 130. The distal end 120 is configured to seat in the anterior chamber 106 pointing away from the trabecular meshwork 112 when the ocular device 115 is implanted in the eye 100. This distal end 120 configuration is to discourage the formation of scar tissue on the distal end 120 and prevent clogging of the inlet during the healing of the implant site. The distal end 120 further comprises one or more openings 124 serving as part of the flow path way to regulate the flow rate of aqueous humor. The one or more openings 124 are configured to promote fluid communication near the flow inlet and prevent clogging of the inlet. The proximal end 122 includes the compliant tube 131. The compliant tube 131 is configured to protrude out of the exterior surface of the cornea 107, sclera 109 or conjunctiva 114 and is flexible to comply with eyelid movement or collapsible under the pressure from the eyelid or hand. This configuration allows continuous aqueous humor flow through the compliant tube 131 with minimum irritation to the eye 100 or eyelid. The length of the fluid conduit 130 is sized to permit drainage of aqueous humor from the anterior chamber 106 to the tear film 108 of the eye 100 when the ocular device 115 is implanted in the cornea 107, limbus 110, sclera 109 or conjunctiva 114.

Figure 8:
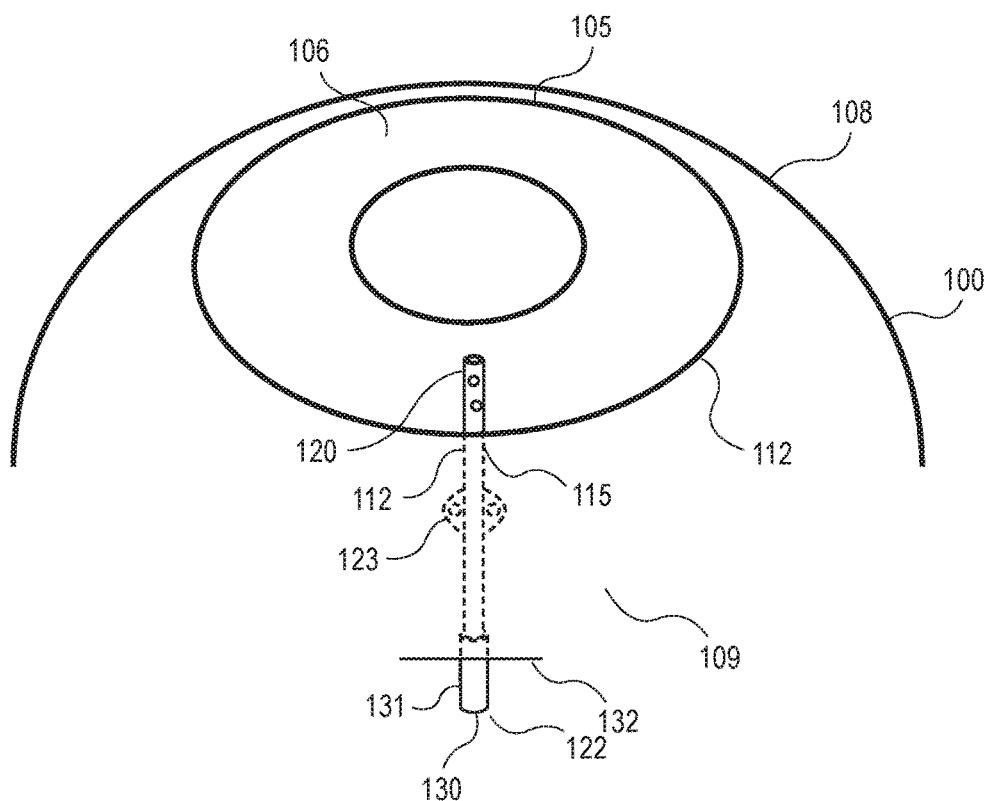
FIG. 8 is a perspective view of an eye showing the cornea, sclera, and iris with the implanted ocular device according to FIG. 2.

FIG. 8 shows the ocular device 115 dimensionally adapted for trans-sclera 109 position after it is implanted in the eye 100. The ocular device 115 includes the body 121 defining the fluid conduit 130 with a fixed lumen size along the length of the fluid conduit 130, the distal end 120 and the proximal end 122 to allow the aqueous humor to flow from the distal end 120 to the proximal end 122. The proximal end 122 comprises the compliant tube 131. A portion of the body 121 (shown in dotted line) is embedded in the sclera 109 of the eye 100. A portion of the compliant tube 131 (as shown in the solid lines) protrudes out of the external surface of the sclera 109 through the incision 132 within the sclera 109. As shown in this figure, the edge of the compliant tube 131 may be rounded to reduce irritation to the eye 100 and eyelids. In another embodiment of this invention, the compliant tube 131 is flexible to comply with eyelid movement or collapsible under pressure from either the eyelid or the hand. The one or more suture holes 123 are configured to receive suture and secure the ocular device 115 in the eye 100. The distal end 120 (as shown in the solid lines) is seated in the anterior chamber 106 and pointing away from the angle 105 of the anterior chamber 106 and the trabecular meshwork 112. The above dimensions and arrangement are exemplary only, and other sizes and arrangements are contemplated. When the device 115 is implanted in the eye 100, it provides IOP relief by draining the aqueous humor from the anterior chamber 106 of the eye 100 to the tear film 108 in a controlled manner as shown in FIG. 8.

Figure 9:
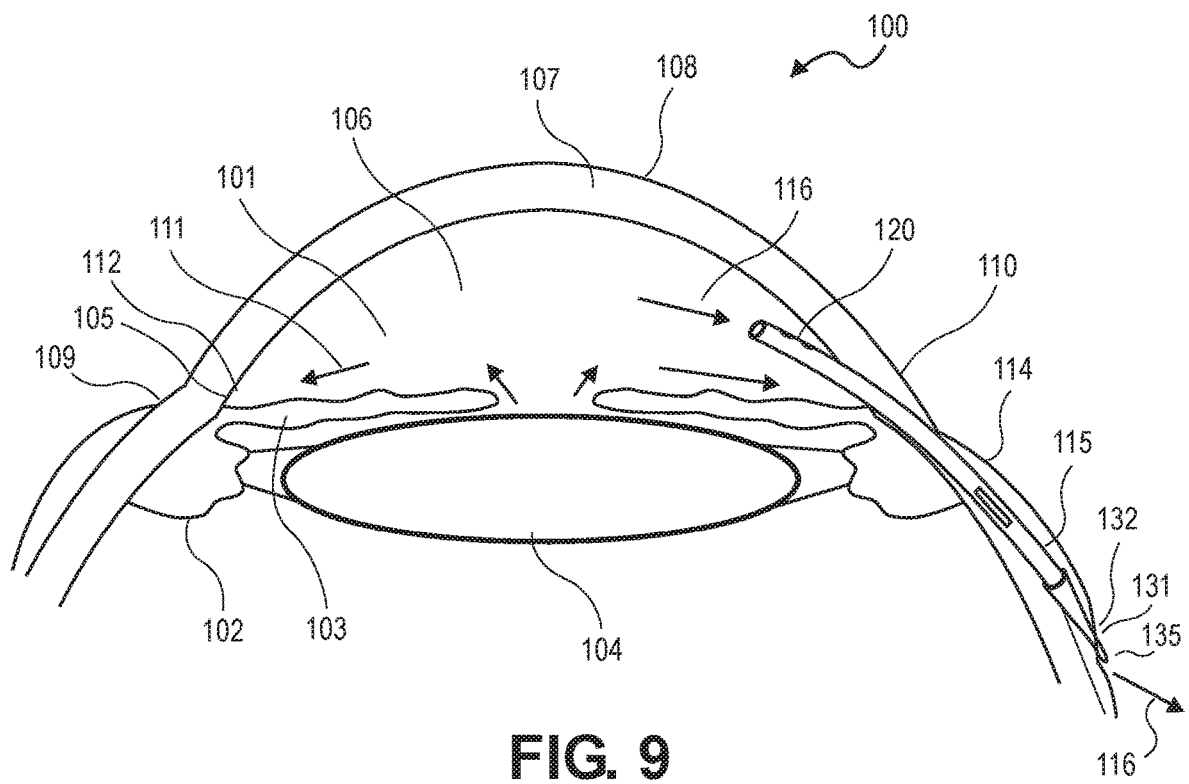
FIG. 9 is a cross-sectional view of the anterior segment of an eye showing the cornea, sclera, and conjunctiva with the implanted ocular device according to FIG. 2. The protruded portion of the compliant tube was compressed and conforming to the surface of the eyeball.

FIG. 9 is a cross-sectional view of the anterior segment 101 of an eye 100 with the implanted ocular device 115. The distal end 120 is seated in the anterior chamber 106 and directing away from the angle 105 of the anterior chamber 106 and the trabecular meshwork 112. A portion 135 of the compliant tube 131 protrudes out of the external surface of the conjunctiva 114 through the incision 132. As shown in the figure, the protruded portion 135 of the compliant tube 131 collapses under the pressure from the eyelid (not shown) and conforms to the surface of the eye 100 with minimum irritation to the eye 100 or eyelid. Because the lumen 133 of the collapsed compliant tube 131 remains larger than the lumen 136 of the fluid conduit 130, this configuration allows continuous aqueous humor flow through the compliant tube 131 when the compliant tube 131 is collapsed. The implanted ocular device 115 provides IOP relief by draining the aqueous humor from the anterior chamber 106 of the eye 100 to the tear film 108 in a controlled manner as shown in FIG. 9. The flow direction of the aqueous humor is indicated by the arrows 116.

Figure 10:
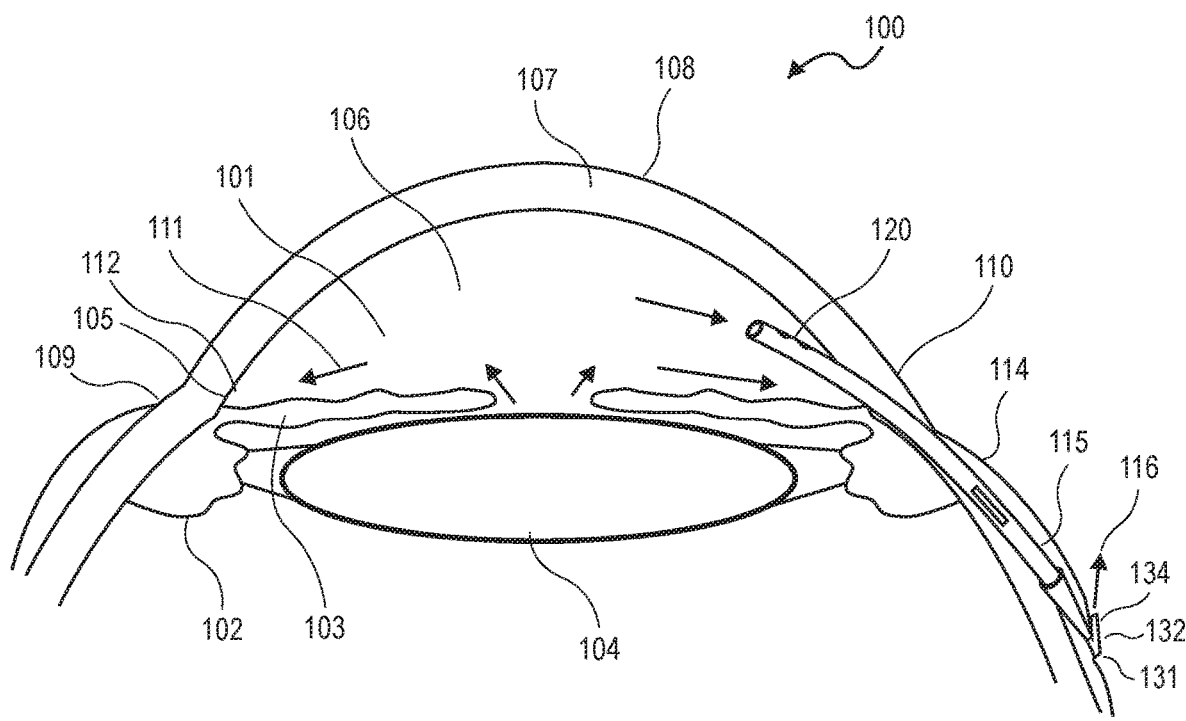
FIG. 10 is a cross-sectional view of the anterior segment of an eye showing the cornea, sclera, and conjunctiva with the implanted ocular device according to FIG. 2. The protruded portion of the compliant tube was moved by the eyelid, and thereby flexing to the other side of the incision and conforming to the surface of the eyeball.

In another embodiment of this invention, the compliant tube 131 is flexible and complies with the movement of the eyelid (not shown) on the surface of the eyeball 100 to minimalize irritation to the eye 100 or eyelid. As shown in FIG. 10, a portion 134 of the compliant tube 131 protrudes out of the external surface of the conjunctiva 114 through the incision 132. Normal eye 100 can brinks up to 20-30 blinks/minute. As the eyelid moves on the eyeball 100, any rigid foreign body may cause irritation to both the eyelid and the eyeball 100. In this invention, the protruded portion 134 of the compliant tube 131 is flexible and complies to the movement of the eyelid to reduce irritation to the eyelid and the eyeball 100. As shown in FIG. 10, the protruded portion 134 of the compliant tube 131 complies to the movement of the eyelid and may be moved by the eyelid, and thereby flexing to the other side of the incision 132 with a large flexing angle. The compliant tube 131 remains conformed to the surface of the eyeball 100 after the flexing. In one embodiment of this invention, the flexing angle ranges from 10 degree to 300 degree. Because the lumen 133 of the flexed compliant tube 131 remains larger than the lumen 136 of the fluid conduit 130, this configuration allows continuous aqueous humor flow through the compliant tube 131 with minimum irritation to the eye 100 or eyelid even when the compliant tube 131 is flexed. The flow direction of the aqueous humor is indicated by the arrows 116.

In another embodiment of this invention, the fluid conduit 130 comprises a slowly enlarged lumen 136 along the length of the fluid conduit 130. The lumen 136 size increases from the distal end 120 to the proximal end 122 to reduce the chance for clogging in the fluid conduit 130 because the slowly enlarged lumen 136 allows the aqueous humor outflow to remove any debris deposition in the fluid conduit 130. The lumen of the fluid conduit 130 comprises a generally round shape. However, it is understood that other lumen shapes may be suitable as well. For example, the lumen shapes of the fluid conduit 130 may be round, oval, rectangular, square, multiple lumens, half-round, half-oval or irregular, etc.

Figure 11:
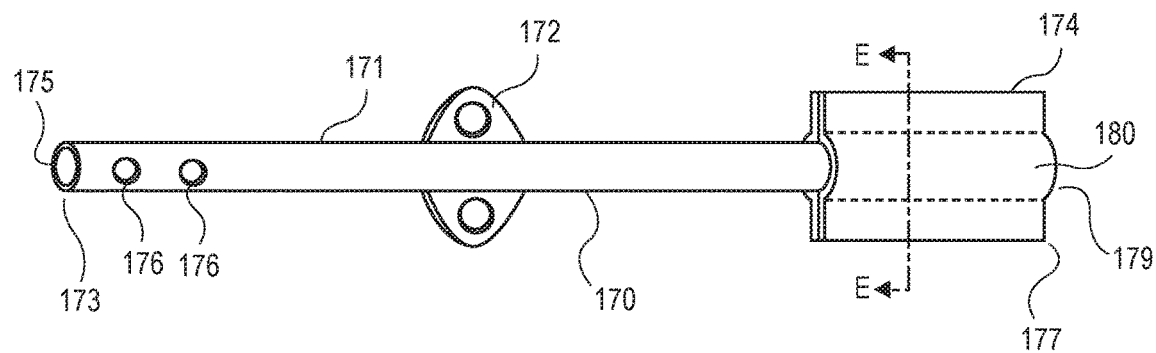
FIG. 11 is a perspective view of an ocular device with compliant tube as described in another embodiment of this disclosure. The compliant tube comprises bonded sheets.
Figure 12:
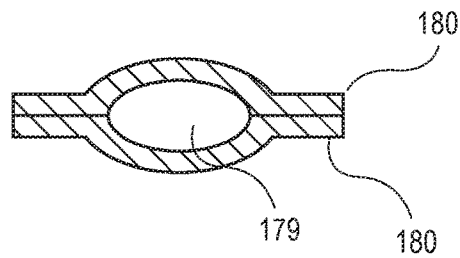
FIG. 12 is a cross-sectional view (along Line EE) of the ocular device according to FIG. 11.

In another embodiment of this invention, the compliant tube of an ocular device comprises bonded sheets. FIG. 11 is a perspective view of an ocular device 170 with a body 171, a plurality of suture holes 172, a distal end 173 and a proximal end 174 according to an embodiment of the present invention. The distal end 173, the body 171, suture holes 172, and the proximal end 174 of the ocular device 170 may all be formed integrally as a unit. The tubular-shaped body 171 defines a fluid conduit 175 with a fixed lumen size along the length of the fluid conduit 175, the distal end 173 and the proximal end 174 to allow the aqueous humor to flow from the distal end 173 to the proximal end 174. There is no valve, narrow section or filter in the fluid conduit 175. The distal end 173 comprises a plurality of opening 176, thereby reducing the chance for blocking the entrance of the fluid conduit 175 and the clogging of the device 170. The suture holes 172 on the ocular device 170 are configured to receive suture, and thereby increasing the fixation of the device 170 in the eye 100 when it is implanted in the eye 100. The proximal end 174 includes a compliant tube 177. The compliant tube 177 comprises bound sheets 180 with a low cross-sectional profile. FIG. 12 shows the cross-sectional view of the compliant tube 177 along Line EE in FIG. 11. A patent lumen 179 is formed between the two sheets 180 that are bound together along the edges of the sheets 180. Because the lumen 179 of the compliant tube 177 remains larger than the lumen of the fluid conduit 175, this configuration allows continuous aqueous humor flow through the compliant tube 177 with minimum irritation to the eye 100 or eyelid even when the compliant tube 177 is collapsed under the pressure from the eyelid. In addition, the compliant tube 177 is also flexible to comply with the movement of the eyelid, and thereby minimizing irritation to the eye 100 or eyelid.

In yet another embodiment of this invention, the fluid conduit 175 comprises an enlarged lumen along the length of the fluid conduit 175. The lumen size increases from the distal end 173 to the proximal end 174 to reduce the chance for clogging in the fluid conduit 175 because the enlarged lumen allows the aqueous humor outflow to remove any possible debris deposition in the fluid conduit 175. The lumen of the fluid conduit 175 comprises a generally round shape. However, it is understood that other lumen shapes may be suitable as well. For example, the lumen shapes of the fluid conduit 175 may be round, oval, rectangular, square, multiple lumens, half-round, half-oval or irregular, etc.

In another embodiment of this invention, the ocular device 115 is surgically implanted in the eye 100 with the proximal end 122 seated on the external surface of the sclera 109. The distal end 120 of the ocular device 115 remains in the anterior chamber 106. Alternatively, the ocular device 115 is implanted in the eye 100 with the proximal end 122 seated on the external surface of the cornea 107. The distal end 120 of the ocular device 115 remains in the anterior chamber 106. In one embodiment, the ocular device 115 is implanted in the eye 100 with the proximal end 122 seated on the external surface of the conjunctiva 114. The distal end 120 of the ocular device 115 remains in the anterior chamber 106.

Figure 13:
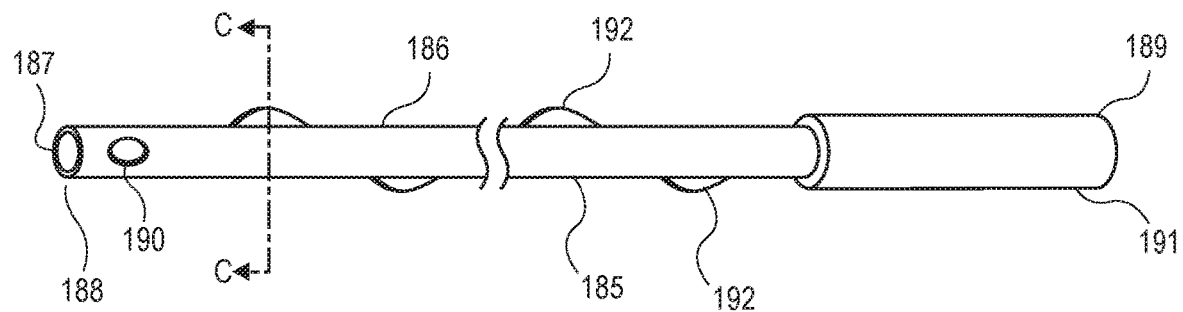
FIG. 13 is a perspective view of the ocular device with one or more retainers described in one embodiment of this disclosure.
Figure 14:
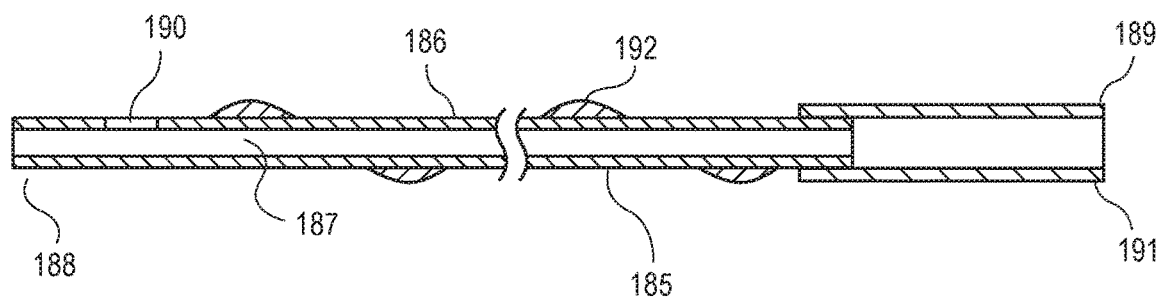
FIG. 14 is a cross-sectional view of the ocular device according to FIG. 13 with one or more retainers.
Figure 15:
FIG. 15 is a cross-sectional view (along Line CC) of the ocular device according to FIG. 13.
Figure 16:
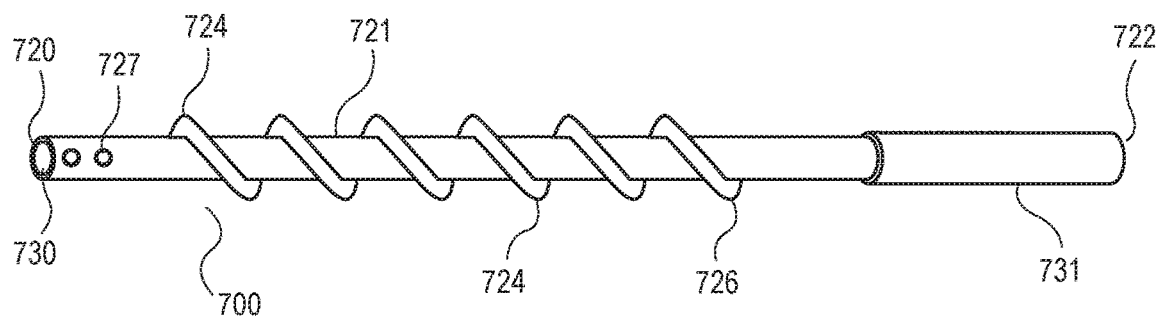
FIG. 16 is a perspective view of the ocular device with wire shaped retainer described in one embodiment of this disclosure.

In yet another embodiment of this invention, the body of an ocular device comprises one or more retainers on the exterior surface of the body as shown in FIG. 13. The ocular device 185 includes a body 186 defining a fluid conduit 187 with a fixed lumen size along the length of the fluid conduit 187, a distal end 188 and a proximal end 189 to allow the aqueous humor to flow from the distal end 188 to the proximal end 189. There is no valve, narrowing or filter in the fluid conduit 187. The distal end 188 comprises a plurality of opening 190, thereby reducing the chance for the debris in the aqueous humor to block the entrance of the fluid conduit 187 and clogging of the device 185. The proximal end 189 of the device 185 comprises a compliant tube 191. The compliant tube 191 is configured to be flexible to comply with the movement of the eyelid or collapsible under pressure from either the eyelid or the hand to minimize irritation to the eyelid or the eye 100. The ocular device 185 may include, by way of non-limiting example, any number of retainers 192. The retainers 192 extend beyond the exterior surface of the body 186 and are configured to anchor the ocular device 185 in the eye 100 by introducing a higher friction between the ocular device 185 and the eye 100. The retainers 192 may be made of an elastic material such that they are able to be flexed inward to reduce their cross-sectional profiles for easier penetration through the cornea 107 or sclera 109. However, after the retainer 192 is placed in the eye 100, it acquires a shape to anchor the ocular device 185 in the eye 100. FIG. 14 shows the cross-sectional view of the ocular device 185. FIG. 15 shows the cross-sectional view of the ocular device 185 along Line CC in FIG. 13. The retainer 192 is seated on the exterior surface of the body 186. While the shape the retainer 192 illustrated in the FIGS. 13 and 14 is shown as a dome shape, it is understood that other shapes to increase friction may be suitable as well. For example, the shape of the retainer 192 may be round, oval, cylinder, square, triangular, disk, or irregular, etc. In addition, the one or more retainers 192 may be arranged in linear, in random, in spiral patterns on the surface of the body 186. In another embodiment of this invention, the retainer 192 may be fiber, wire (as shown in FIG. 16), thread, nodule, ridge, protrusion, mesh, brush, foam, or scaffold, etc. The retainer 192 can be made by material such as stainless steel, shape memory material, Nitinol, plastic, or metal.

In one embodiment of this invention, the fluid conduit 187 comprises an enlarged lumen along the length of the fluid conduit 187. The lumen size increases from the distal end 188 to the proximal end 189 to reduce the chance for clogging in the fluid conduit 187 because the enlarged lumen allows the aqueous humor outflow to remove any possible debris deposition in the fluid conduit 187. The lumen of the fluid conduit 187 comprises a generally round shape. However, it is understood that other lumen shapes may be suitable as well. For example, the lumen shapes of the fluid conduit 187 may be round, oval, rectangular, square, multiple lumens, half-round, half-oval or irregular, etc.

In further another embodiment of this invention, the retainer 192 of an ocular device comprises one or more wires on the exterior surface of the ocular device. As shown in FIG. 16, the ocular device 700 includes a body 721 defining a fluid conduit 730 with a fixed lumen along the length of the fluid conduit 730, a distal end 720 and a proximal end 722 to allow the aqueous humor to flow from the distal end 720 to the proximal end 722. There is no valve, narrowing or filter in the fluid conduit 730. The distal end 720 comprises a plurality of opening 727, thereby reducing the chance for the debris in the aqueous humor to block the entrance of the fluid conduit 730 and the clogging of the device 700. The proximal end 722 comprises the compliant tube 731. The compliant tube 731 is configured to be flexible to comply with the movement of the eyelid or collapsible under pressure from either the eyelid or the hand to minimize irritation to the eyelid or the eye 100. The ocular device 700 further comprises one or more retainers 726 on the exterior surface of the body 721. The one or more retainers 726 comprise one or more wires 724. Each wire 724 is wrapped around the exterior surface of the body 721 and engages with the eye 100 when it is implanted in the eye 100. The wire 724 is configured to anchor the ocular device 700 in the eye 100 by introducing a higher friction between the ocular device 700 and the eye 100. The wire 724 may also be made of an elastic material and serve as a reinforcement for the ocular device 700. Therefore, the ocular device 700 is able to be flexed to reduce its cross-sectional profile for fitting into the delivery device, allowing easier penetration through the cornea 107 or sclera 109. After the ocular device 700 is implanted in the eye 100, the ocular device 700 can recover to its original shape. While the cross-sectional shape of the wire 724 illustrated in the FIG. 16 is shown as a round shape, it is understood that other cross-sectional shapes to increase friction may be suitable as well. For example, the cross-sectional shape of the wire 724 may be round, oval, cylinder, square, triangular, or irregular, etc. While the wire 724 illustrated in this figure is shown to wrap around the ocular device 700, it is understood that other wire 724 arrangement may be suitable as well. For example, the wire 724 may be arranged in linear, in helix, in random, or in spiral pattern on the surface of the body 721. The wire 724 can be made by material such as stainless steel, shape memory material, Nitinol, plastic, or metal.

In another embodiment of this invention, the fluid conduit 730 comprises an enlarged lumen along the length of the fluid conduit 730. The lumen size increases from the distal end 720 to the proximal end 722 to reduce the chance for clogging in the fluid conduit 730 because the enlarged lumen allows the aqueous humor outflow to remove any possible debris deposition in the fluid conduit 730. The lumen of the fluid conduit 730 comprises a generally round shape. However, it is understood that other lumen shapes may be suitable as well. For example, the lumen shapes of the fluid conduit 730 may be round, oval, rectangular, square, multiple lumens, half-round, half-oval or irregular, etc.

In yet another embodiment of this invention, the exterior surface of the body 721 is configured to promote tissue ingrowth or tissue integration with the eye 100. The body 721 of the ocular device 700 is in contact with eye 100 tissue after the ocular device 700 is implanted in the cornea 107 or sclera 109. The tissue ingrowth or tissue integration can increase the fixation of the ocular device 700 in the implantation site. Additionally, the tissue ingrowth or tissue integration can also eliminate potential dead space around the ocular device 700, thus reducing or removing the risk of a tunnel infection into the eye 100. To achieve those goals, the surfaces of the body 721 can be coated with polymer coatings or biologically active materials to promote tissue ingrowth or tissue integration with the implanted ocular device 700. Alternatively, the exterior surface of the body 721 is treated with chemicals, textured or roughened to increase surface roughness promoting tissue ingrowth or tissue integration with the eye 100.

In further embodiment of this invention, the ocular device comprises a fluid conduit with a length sufficient to provide fluid communication between the anterior chamber 106 and the tear film 108 when the ocular device is implanted in the cornea 107, limbus 110, sclera 109 or conjunctiva 114. The fluid conduit also comprises a fixed lumen size along the length of the fluid conduit and is sufficiently large to allow the aqueous humor to flow through the fluid conduit to relieve the IOP without being blocked by debris in the aqueous humor. At the same time, the fluid conduit comprises a geometry (i.e. length, lumen size, tortuosity) to provide sufficient aqueous humor flow resistance to maintain a minimum IOP in the eye 100 to avoid hypotony without using pressure regulation mechanisms such as a valve, a filter or a narrowing in the fluid conduit. The length of the fluid conduit should also be sufficiently long to impede the bacteria from moving against the aqueous humor outflow and migrating through the fluid conduit. Alternatively, the fluid conduit further comprises an antibacterial material with antibacterial surface area to prevent bacteria from gaining entry into the anterior chamber 106 through the fluid conduit without the use of a valve, a filter, or a narrowing in the fluid conduit. In another embodiment of this invention, the ocular device is configured to include, by way of non-limiting example, any number of fluid conduit. Alternatively, the fluid conduit comprises an enlarged lumen along the length of the fluid conduit. The lumen size increases from the distal end to the proximal end to reduce the chance for clogging in the fluid conduit because the enlarged lumen allows the aqueous humor outflow to remove any possible debris deposition in the fluid conduit. The lumen of the fluid conduit comprises a generally round shape. However, it is understood that other lumen shapes may be suitable as well. For example, the lumen shapes of the fluid conduit may be round, oval, rectangular, square, multiple lumens, half-round, half-oval or irregular, etc.

In this invention, the geometry (i.e. length, lumen size, tortuosity) of the fluid conduit provides sufficient aqueous humor outflow through the fluid conduit to relieve the high pressure and determine the IOP of the eye 100 when the ocular device is implanted in the eye 100. The IOP of normal eye 100 ranges from 12-22 mm Hg, and eye pressure of greater than 22 mm Hg is considered higher than normal, and eye pressure of less than 5 mm Hg is considered hypotony. In this embodiment, the geometry of the flow conduit is selected so as to achieve an IOP ranges from 6 mm Hg to 22 mm Hg. The geometry of the fluid conduit may also be selected to provide sufficient outflow resistance to avoid the hypotony, and simultaneously prevent clogging from the debris in the aqueous humor.

Assuming the lumen of a fluid conduit is round shape, the pressure difference ($\Delta P$) and flow resistance (R) between the two ends of the straight fluid conduit can be calculated by fluid-dynamics Hagen-Poiseuille equation:

$$\Delta P = 8\mu L Q/\pi r^4 \quad \text{(Equation 1)}$$

where $\Delta P$ is the pressure difference between the two ends of the fluid conduit in this invention, L is the length of the fluid conduit, $\mu$ is the dynamic viscosity of the aqueous humor, p=7.2× $10^{-4}$ Pa·sec at 37° C.

Q is the volumetric flow rate of the aqueous humor in the fluid conduit, r is the radius of the fluid conduit.

$$R = 1/Ct = 8\mu L/\pi r^4 \quad \text{(Equation 2)}$$

where
R is the flow resistance between the two ends of the fluid conduit. It is inversely proportional to the device facility (Ct) of the ocular device.

The pressure difference and flow resistance between the two ends of the fluid conduit is directly proportional to the length (L) of the fluid conduit and the viscosity (η) of the aqueous humor, and inversely proportional to the radius to the fourth power ($r^4$). As a result, very small changes in fluid conduit radius lead to large changes in pressure difference and flow resistance. Because the device facility (Ct) is inversely proportional to the flow resistance of the ocular device, the device facility is also strongly affected by the geometry (i.e. lumen size and length) of the fluid conduit. The device facility of the ocular device is proportional to the conduit lumen size and inversely proportional to the fluid conduit length.

The viscosity of the aqueous humor normally stays within a small range. The required aqueous humor flow rate in the fluid conduit of the ocular device is usually lower than the typical aqueous humor production rate (i.e. 1.5 to 3.0 micro liters per minute) because some of the aqueous humor flows out of the interior chamber 106 through the traditional outflow route. For the ocular device in this invention, the proximal end of the device is in direct communication with the tear film 108 at about one atmospheric pressure without additional pressure regulation mechanisms such as a valve, a filter or a narrowing in the fluid conduit. On the other hand, the distal end of the ocular device is placed in the anterior chamber 106 at the same pressure with the anterior chamber 106 (IOP).

In this invention, the ocular device bypasses the clog-prone trabecular meshwork 112 providing additional draining pathway for the aqueous humor after it is implanted in the eye 100. The aqueous humor formation rate can be estimated by the expanded form of the Goldmann's equation:

$$F=C^*(IOP-EVP)+Q+Uv \quad \text{(Equation 3)}$$

where
F is the aqueous humor formation rate,
C is the outflow facility through the trabecular meshwork 112 pathway,
IOP is the intraocular pressure and can be measured by a tonometry,
EVP is the episcleral venous pressure,
Uv is the aqueous humor flow rate contribution of the uveoscleral pathway,
Q is the aqueous humor flow rate through the ocular device, and it is proportional to the IOP as shown in Equations 1, 2 and 4.

$$Q=IOP^*Ct \quad \text{(Equation 4)}$$

where
Ct is the device facility of the ocular device and is inversely proportional to the flow resistance (R) of the ocular device, then the Goldmann's equation becomes:

$$F=C^*(IOP-EVP)+IOP^*Ct+Uv \quad \text{(Equation 5)}$$

$$\text{or } IOP=(F-Uv+C^*EVP)/(C+Ct) \quad \text{(Equation 6)}$$

The aqueous humor formation rate (F) for human eye 100 ranges from 1.5 to 3.0 μL/min and can be measured by a fluorophotometry. Aqueous humor formation rate is normally about 3.0 μL/min in the morning, 2.5 μL/min in the afternoon, and drops to 1.5 μL/min at night. The mean outflow facility (C) for healthy human eye 100 is about 0.22 μL/min/mm Hg. The outflow facility of the eye can be determined noninvasively by using a Schiotz tonometer or the tonography setting on a pneumotonometer. The EVP is approximately 8 to 9 mm Hg. The aqueous humor flow rate through the uveoscleral pathway (Uv) is estimated to be about 0.4 μL/min and can be measured by a venomanometry. From Equation 4, the outflow facility of the ocular device (Ct) can be obtained by measuring the pressure drop through the ocular device at various flow rates (Q).

As shown in Equation 6, the IOP of the eye 100 is proportional to the aqueous humor formation rate (F) and is inversely proportional to the device facility (Ct) of the implanted ocular device. An ocular device with a high device facility would yield a lower IOP in the eye 100 due to the higher aqueous humor draining efficiency in the implanted ocular device. On the other hand, an ocular device with a low device facility would yield a higher IOP in the eye 100. As indicated in Equation 2, device facility (Ct) is inversely proportional to the flow resistance (R) between the two ends of the fluid conduit. As a result, the IOP of the eye can be regulated by the device facility or the flow resistance of the ocular device without the need for a pressure regulation mechanism such as a valve, a narrowing or a filter in the fluid conduit.

As shown in Equation 2, the flow resistance and the device facility (Ct) of the ocular device with various fluid conduit lengths and lumen size can be calculated. Otherwise, the device facility can be acquired from the flow rate (Q) vs. pressure (IOP) data obtained from the experiment as indicated in Equation 4. The device facility is strongly affected by the geometry (i.e. lumen size and length) of the fluid conduit. The device facility of the ocular device is proportional to the conduit lumen size and inversely proportional to the fluid conduit length. As a consequence, the IOP of the eye 100 can be regulated by the geometry (i.e. lumen size and length) of the fluid conduit of the implanted ocular device in the eye 100.

With the expanded Goldmann's equation (Equation 6), outflow facility (C) and the acquired device facility (Ct), the IOP of the eye 100 with the implanted ocular devices at various aqueous humor formation rate can be simulated. As indicated in the Equation 6, the IOP of the eye 100 is strongly affected by the aqueous humor formation rate (F). A lower aqueous humor formation rate will lead to a lower IOP in the eye 100. Because the aqueous humor formation rate normally drops to the lowest at 1.5 μL/min at night, a minimum IOP of the eye 100 at night after the device is implanted in the eye 100 can be estimated by Equation 6 with the acquired device facility and the eye's 100 outflow facility. On the other hand, because 6.0 mmHg is considered the threshold for hypotony, a maximum device facility to avoid hypotony can be estimated by using this minimum IOP at night and the eye's outflow facility in the Equation 6. In one embodiment of this invention, ocular devices of various device facilities are available for implantation. The clinician can use Equation 6 and the eye's outflow facility to estimate the maximum device facility that can be used in the eye 100 to avoid hypotony, and then implant the ocular device with the appropriate device facility in the eye 100.

Similarly, as indicated in the Equation 6, a higher aqueous humor formation rate will lead to a higher IOP in the eye 100. Because the aqueous humor formation rate normally raises to the highest at 3.0 μL/min in the morning, a maximum IOP of the eye 100 after the ocular device is implanted in the eye 100 can be estimated by Equation 6, the eye's 100 outflow facility and the acquired device facility. In one embodiment of this invention, ocular devices of various device facilities are fabricated. Because 22.0 mmHg is the threshold for normal IOP, a minimum device facility can be estimated by using this maximum IOP and eye's 100 outflow facility by Equation 6. In another embodiment of this invention, ocular devices of various device facilities are available for implantation. The clinician can use Equation 6 and the eye's 100 outflow facility to estimate the minimum device facility that can be used in the eye 100 to achieve the target IOP, and then implant the ocular device with the appropriate device facility in the eye 100.

As discussed in the previous embodiments, an ocular device with a high device facility (Ct) is more effective in draining the aqueous humor, and thereby providing a lower IOP after the ocular device is implanted in the eye 100. On the other hand, an ocular device with a low device facility can yield a higher IOP after the ocular device is implanted in the eye 100. Because the device facility is strongly affected by the geometry (i.e. lumen size and length) of the fluid conduit an ocular device with a larger fluid conduit lumen size yields a higher device facility, and thereby leading to a lower IOP in the eye 100. In addition, a larger lumen size in the fluid conduit also reduces the chance for clogging caused by the debris in the aqueous humor. However, an ocular device with an excess large lumen size (with an excess high device facility) has a higher risk for hypotony in the eye 100. Similarly, an ocular device with a short fluid conduit length yields a higher device facility, and thereby leading to a lower IOP in the eye 100. However, an ocular device with an excess short fluid conduit length has a higher risk for bacteria migration through the fluid conduit. On the other hand, an ocular device with a longer fluid conduit length increases the conduit's ability in impeding the transmission of microorganisms into the anterior chamber by increasing the difficulty for the microorganisms to move against the aqueous humor outflow.

In one embodiment of this invention, the ocular device comprises a conduit geometry (length and lumen size) to yield a sufficient device facility to reduce IOP, and simultaneously prevent low pressure or hypotony in the eye 100. As shown in Equation 2, the increase in conduit length enables the increase in fluid conduit lumen size without affecting the device facility and its effectiveness in reducing IOP and preventing hypotony in the eye 100. A large fluid conduit lumen size can reduce the risk of clogging caused by the debris in the aqueous humor. As discussed previously, a longer fluid conduit also increases the conduit's ability in impeding the transmission of microorganisms into the anterior chamber by increasing the difficulty for the microorganisms to move against the aqueous humor outflow. The increase in fluid conduit's lumen size also provides a larger antimicrobial surface area to further impede the transmission of microorganisms into the anterior chamber 106. As a result, the IOP of the eye 100 can be regulated by the geometry of the ocular device, particularly the geometry (i.e. lumen size and length) of the fluid conduit, without using a pressure regulation mechanism such as a valve, a filter or a narrowing in the fluid conduit. A normal IOP can be maintained by using the ocular device with an appropriate conduit lumen size and length.

As discussed in previous sections, an ocular device with a longer fluid conduit length is advantageous in allowing a larger conduit lumen size to reduce IOP, avoid hypotony, clogging, and simultaneously reducing the chance for the bacterial to migrate into the anterior chamber 106. However, the ocular device with a long fluid conduit length may interfere with patient's field of vision or block the trabecular meshwork 112. In another embodiment of this invention, the ocular device offers several methods to reduce IOP, avoid hypotony, clogging and bacterial migration issues without interfering with patient's field of vision or blocking the trabecular meshwork 112. In another embodiment of this invention, the ocular device provides a method to impede the transmission of microorganisms into the anterior chamber without using a filter, a valve or a narrow conduit. The fluid conduit of the device comprises a sufficient length to prevent bacteria from migrating against the aqueous humor flow, and thereby gaining entry into the anterior chamber through the fluid conduit. In addition, the surface of the fluid conduit comprises an antimicrobial material to prevent bacteria from migrating into the anterior chamber through the fluid conduit. Because the antimicrobial effectiveness of this antimicrobial surface is proportional to its surface area, the increase in conduit length and surface roughness can increase the antimicrobial surface area and the conduit's efficiency for impeding the transmission of microorganisms into the anterior chamber. The antimicrobial material comprises material such as metals, metal ion, metal oxide, metal compound, silver, silver oxide, silver nitrate, silver compound, silver nanoparticles, copper, zinc, and platinum, etc. Alternatively, the ocular device is made by the antimicrobial material. In addition, the antimicrobial surface of the fluid conduit also prevents debris or deposits build-up in the fluid pathway.

In one embodiment of this invention, the surface of the fluid conduit comprises an antifouling material to prevent bacteria from migrating into the anterior chamber through the fluid conduit. The antifouling material comprises material such as: poly ethylene glycol, poly ethylene glycol copolymers, poly propylene glycol, hydrogel, poly (vinyl alcohol), poly (2-hydroxyethyl methacrylate) (PHEMA), crosslinked PEG diacrylate, Zwitterionic compound, poly carboxybetaine methacrylate, etc. Alternatively, the ocular device is made by the antifouling material. In addition, the antifouling surface of the fluid conduit can also prevent debris or deposits build-up in the fluid pathway.

Figure 18:
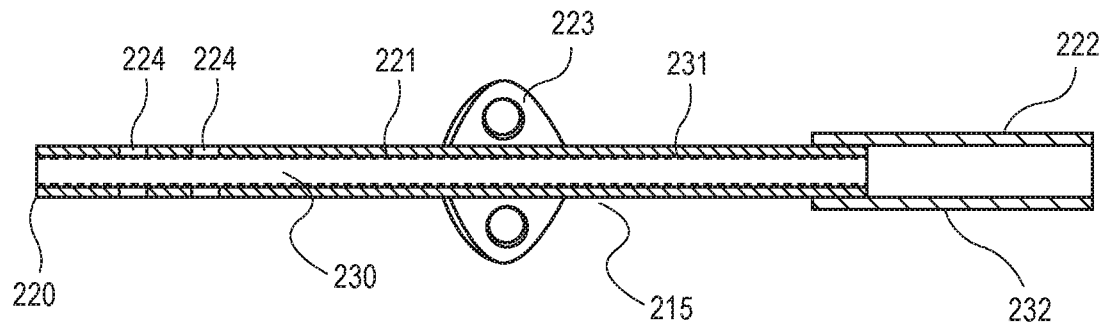
FIG. 18 is a cross-sectional view of the ocular device with rough conduit surface as described in one embodiment of this disclosure.

In further another embodiment of this invention, the IOP of the eye 100 and the device facility (Ct) of the ocular device can be regulated by the surface roughness of the fluid conduit. A rough conduit surface can increase the friction between the aqueous humor and the conduit surface, thereby increasing the flow resistance of the ocular device. The flow resistance is usually proportional to the degree of roughness on the fluid conduit surface. The rougher the conduit surface, the higher the flow resistance. This increase in flow resistance can reduce the device facility because the device facility is inversely proportional to the flow resistance as shown in Equation 2. FIG. 18 shows an example of the increased surface roughness caused by bumps or texture on the inner surface of the fluid conduit. The ocular device 215 has a similar perspective appearance with the ocular device 115 shown in FIG. 2. As shown in the cross-sectional view of the ocular device 215, the ocular device 215 includes a body 221 defining a fluid conduit 230 with a fixed lumen size along the length of the fluid conduit 230, a distal end 220 and a proximal end 222 to allow the aqueous humor to flow from the distal end 220 to the proximal end 222 when it is implanted in the eye 100. There is no valve, narrowing or filter in the fluid conduit 230. The distal end 220 is configured to seat in the anterior chamber 106 and is pointing away from the trabecular meshwork 112 when it is implanted in the anterior chamber 106. The distal end 220 further comprises one or more openings 224 serving as part of the flow pathway to regulate the flow rate of aqueous humor. The one or more openings 224 are configured to promote fluid communication near the flow inlet and prevent clogging of the inlet. The distal end 220 is configured to discourage the formation of scar tissue on the distal end 220 and prevents clogging of the inlet during the healing of the implant site. The proximal end 222 further comprises a compliant tube 232 that is configured to protrude out of the exterior surface of the cornea 107, sclera 109 or conjunctiva 114 and to minimize irritation to the eyelids. The compliant tube 232 is flexible to comply with the movement of the eyelid or collapsible under pressure from either the eyelid or the hand to minimize irritation to the eyelid or the eye 100. The body 221 also comprises one or more suture holes 223 or retainers on the exterior surface of the body 221. The fluid conduit 230 is sized to permit drainage of aqueous humor from the anterior chamber 106 to the tear film 108 of the eye 100 when the ocular device 215 is implanted in the cornea 107, limbus 110, sclera 109 or conjunctiva 114. The fluid conduit 230 also comprises surface roughness 231 on the inner surface of the fluid conduit 230. Compared with the ocular device 115 with similar conduit length and lumen size, the device 215 with a rough conduit surface would yield a higher IOP in the eye 100 due to its higher flow resistance and therefore a lower device facility. The increase in IOP is proportional to the degree of roughness in the fluid conduit 230. As a result, the IOP of the eye 100 and the device facility (Ct) can be regulated by the degree of roughness on the fluid conduit surface without the need for a pressure regulation mechanism such as a valve, a narrowing or a filter in the fluid conduit. Alternatively, the fluid conduit 230 comprises an enlarged lumen along the length of the fluid conduit 230. The lumen size increases from the distal end 220 to the proximal end 222 to reduce the chance for clogging in the fluid conduit 230 because the enlarged lumen allows the aqueous humor outflow to remove any possible debris deposition in the fluid conduit 230. The lumen of the fluid conduit 230 comprises a generally round shape. However, it is understood that other lumen shapes may be suitable as well. For example, the lumen shapes of the fluid conduit 230 may be round, oval, rectangular, square, multiple lumens, half-round, half-oval or irregular, etc.

It is understood that many types of roughness to increase friction and flow resistance may be suitable as well. For example, the shape of the surface roughness 231 may be round, oval, cylinder, disk, rectangular, ridge, protrusion, nodule or irregular, etc. In addition, the surface roughness 231 may be arranged in linear, in random, in continuous or in spiral patterns on the inner surface of the fluid conduit 230. In further another embodiment of this invention, it is understood that other means to increase conduit surface roughness and flow resistance may be suitable as well. The inner surface of the conduit may comprise fiber, scaffold, wire, thread, mesh, brush, foam, groove, or scaffold, etc. They comprise material selected from the group consisting of polymer, metal, glass, and ceramic materials.

As described in the previous sections, the ocular device with sufficient long conduit length is effective in lowering IOP in the eye 100, preventing clogging, avoiding hypotony, impeding the transmission of microorganisms into the anterior chamber 106. However, a long fluid conduit may interfere with patient's field of vision. In this invention, the fluid conduit 230 surface of the ocular device 215 may include sufficient roughness with a higher flow resistance. This increase in flow resistance caused by the surface roughness enables the increase in fluid conduit 230 lumen size without affecting the device facility and its effectiveness in reducing IOP. As a result, an ocular device 215 with a relative shorter fluid conduit 230 can be used to achieve a sufficient flow resistance to avoid hypotony, and thereby reducing the chance for the ocular device 215 to interfere with patient's field of vision. In addition, the antimicrobial effect of the antimicrobial conduit surface is proportional to its surface area. The larger the antimicrobial surface area, the more antimicrobial material can be released to stop the microorganisms from passing through the conduit. The increase in conduit's surface roughness can also increase the conduit's antimicrobial surface area and its ability to impede the transmission of microorganisms into the anterior chamber 106.

Figure 19A:
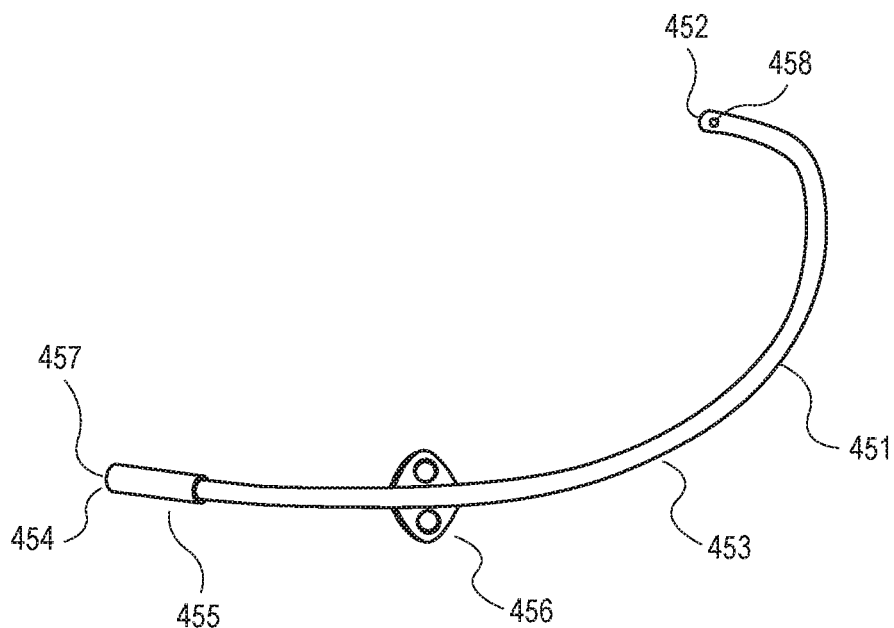
FIG. 19A is a perspective view of the ocular device in one embodiment of this disclosure with tortuous shape.
Figure 19B:
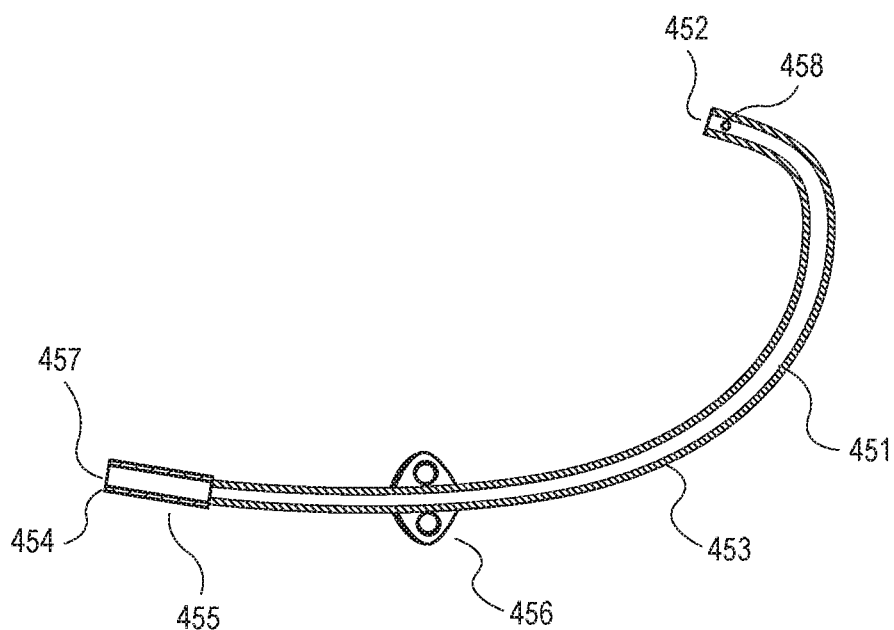
FIG. 19B is a cross-sectional view of the ocular device in one embodiment of this disclosure with tortuous shape.

In another embodiment of this invention, an increase in fluid conduit's tortuosity can increase fluid conduit's total length without interfering with patient's field of vision or blocking the trabecular meshwork 112 after the ocular device is implanted in the eye 100. As shown in FIG. 19*a*, an ocular device 451 includes a tortuous body 453 defining a tortuous fluid conduit 457 with a fixed lumen size along the length of the fluid conduit 457, a distal end 452 and a proximal end 454 to allow the aqueous humor to flow from the distal end 452 to the proximal end 454. The distal end 452 is configured to seat in the anterior chamber 106 pointing away from the trabecular meshwork 112. The one or more openings 458 near the distal end 452 are configured to promote fluid communication near the flow inlet and prevent clogging of the inlet. The proximal end 454 comprises a compliant tube 455. As shown in the cross-sectional view of the ocular device 451 in FIG. 19*b*, there is no valve, narrowing or filter in the fluid conduit 457.

Figure 20:
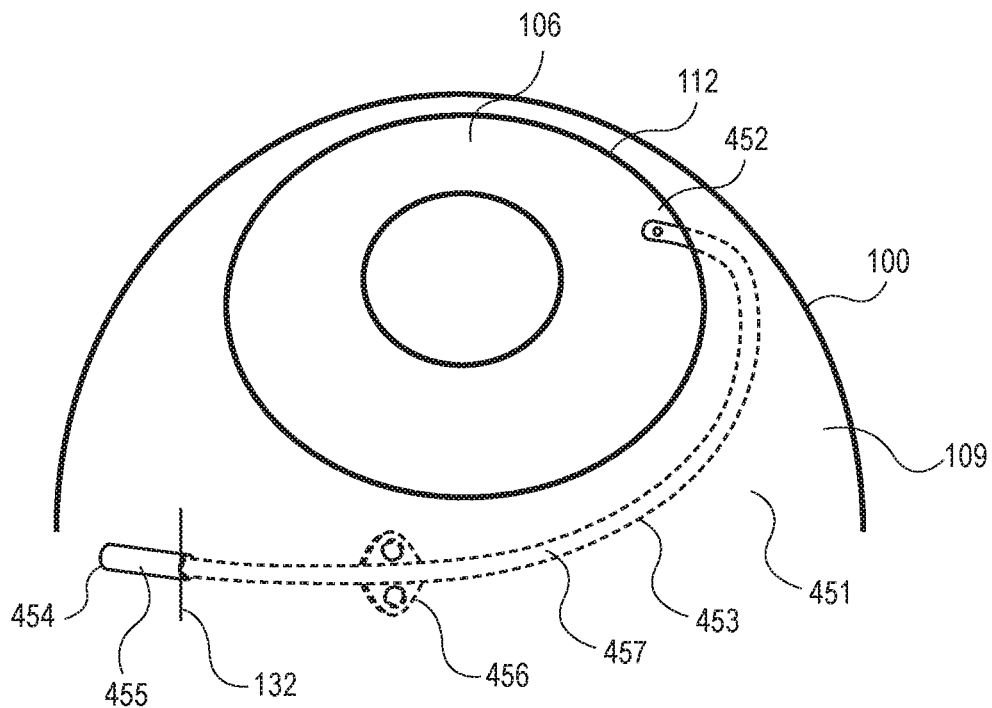
FIG. 20 is a perspective view of an eye showing the cornea, sclera, and iris with the implanted ocular device according to FIG. 19 with tortuous shape.

As shown in FIG. 20, the ocular device 451 has been implanted in the eye 100. The distal end 452 (shown in solid line) is positioned in the anterior chamber 106. A portion of the body 453 (shown in dotted line) is embedded in the sclera 109 of the eye 100 with a tortuous shape, extending circumferentially around the outer perimeter of the anterior chamber 106 without blocking the patient's field of vision or the trabecular meshwork 112. This tortuosity also increases the fluid conduit's total length without changing the linear distance between the distal end 452 and the proximal end 454 of the fluid conduit 457. As shown in Equation 2, the increase in conduit's total length enables the increase in fluid conduit's 457 lumen size without affecting the device facility and its effectiveness in reducing IOP and preventing hypotony in the eye 100. A large fluid conduit's 457 lumen size can reduce the risk of clogging caused by the debris in the aqueous humor. As discussed previously, a longer fluid conduit also increases the fluid conduit's 457 ability in impeding the transmission of microorganisms into the anterior chamber 106 by increasing the difficulty for the microorganisms to move against the aqueous humor outflow. In addition, a longer fluid conduit 457 can also provide a larger antimicrobial surface area to further impede the transmission of microorganisms into the anterior chamber 106.

The compliant tube 455 (shown in solid line) at the proximal end 454 protrudes out of the external surface of the eye 100 through the incision 132. As shown in this figure, the edge of the compliant tube 455 may be rounded to reduce irritation to the eye 100 and eyelids. In another embodiment of this invention, the compliant tube 455 is configured to be flexible to comply with the movement of the eyelid or collapsible under pressure from either the eyelid or the hand to minimize irritation to the eyelid or the eye 100. Alternatively, the compliant tube 455 is configured with low profile to minimize irritation to the eyelids or the eye 100. The one or more suture holes 456 are to receive suture and thereby fixing the ocular device 451 in place during the implantation.

The lumen of the fluid conduit 457 comprises a generally round shape. However, it is understood that other lumen shapes may be suitable as well. For example, the lumen shapes of the fluid conduit 457 may be round, oval, rectangular, square, multiple lumens, half-round, half-oval or irregular, etc.

In one embodiment of this invention, the fluid conduit 457 comprises an enlarged lumen along the length of the fluid conduit 457. The lumen size increases from the distal end 452 to the proximal end 454 to reduce the chance for clogging in the fluid conduit 457 because the enlarged lumen allows the aqueous humor outflow to remove any possible debris deposition in the fluid conduit 457.

While the shape of the ocular device 451 illustrated in the FIGS. 19a and 20 is shown as a half circle shape, it is understood that other tortuous shape to increase fluid conduit's 457 length without interfering with patient's field of vision or blocking the trabecular meshwork 112 may be suitable as well. For example, the ocular device 451 and the coupled fluid conduit 457 may assume a quarter circle, a half circle, a three quarters circle, a full circle, a two-full circle, a zig-zag shape, a spiral shape, a helix shape, a random shape, etc.

Figure 21:
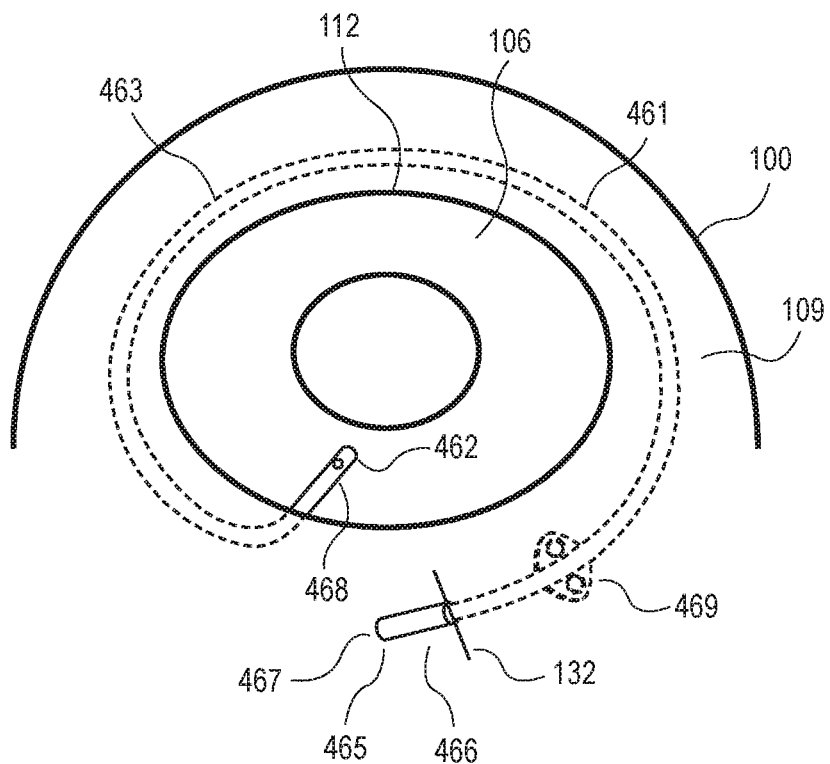
FIG. 21 is a perspective view of an eye showing the cornea, sclera, and iris with the implanted ocular device described in one embodiment of this disclosure with tortuous shape.

In another embodiment of this invention, the ocular device and the coupled flow conduit may assume a full circle shape. As illustrated in the FIG. 21, an ocular device 461 with a tortuous fluid conduit 467 is implanted in the eye 100. The ocular device 461 includes a tortuous body 463 defining a tortuous fluid conduit 467 with a fixed lumen size along the length of the fluid conduit 467, a distal end 462 and a proximal end 465 to allow the aqueous humor to flow from the distal end 462 to the proximal end 465. There is no pressure regulation mechanism such as valve, narrowing or filter in the fluid conduit 467. The distal end 462 (shown in solid line) is seated in the anterior chamber 106 pointing away from the trabecular meshwork 112. The one or more openings 468 near the distal end 462 are configured to promote fluid communication near the flow inlet and prevent clogging of the inlet. The proximal end 465 comprises a compliant tube 466. The compliant tube 466 (shown in solid line) protrudes out of the external surface of the eye 100 through the incision 132 in the eye 100. The compliant tube 466 is configured to be flexible to comply with the movement of the eyelid or collapsible under pressure from either the eyelid or the hand to minimize irritation to the eyelid or the eye 100. The one or more suture holes 469 are to receive suture, and thereby fixing the ocular device 461 in place during the implantation. Portion of the body 463 (shown in dotted line) is embedded in the sclera 109 of the eye 100 with a tortuous shape, extending circumferentially around the outer perimeter of the anterior chamber 106. This increase in conduit tortuosity also increase the conduit's total length without blocking the patient's field of vision or the trabecular meshwork 112.

This tortuosity in the fluid conduit 467 also increases the fluid conduit's 467 total length without changing the linear distance between the distal end 462 and the proximal end 465 of the fluid conduit 467. As shown in Equation 2, the increase in fluid conduit's total length enables the increase in fluid conduit's 467 lumen size without affecting the device facility and its effectiveness in reducing IOP and preventing hypotony in the eye 100. A large fluid conduit's 467 lumen size can reduce the risk of clogging caused by the debris in the aqueous humor. As discussed previously, a longer fluid conduit 467 also increases the conduit's ability in impeding the transmission of microorganisms into the anterior chamber 106 by increasing the difficulty for the microorganisms to move against the aqueous humor outflow. In addition, a longer fluid conduit 467 can also provide a larger antimicrobial surface area to further impede the transmission of microorganisms into the anterior chamber 106. The lumen of the fluid conduit 467 comprises a generally round shape. However, it is understood that other lumen shapes may be suitable as well. For example, the lumen shapes of the fluid conduit 467 may be round, oval, rectangular, square, multiple lumens, half-round, half-oval or irregular, etc.

In one embodiment of this invention, the fluid conduit 467 comprises an enlarged lumen along the length of the fluid conduit 467. The lumen size increases from the distal end 462 to the proximal end 465 to reduce the chance for clogging in the fluid conduit 467 because the enlarged lumen allows the aqueous humor outflow to remove any possible debris deposition in the fluid conduit 467.

Figure 22:
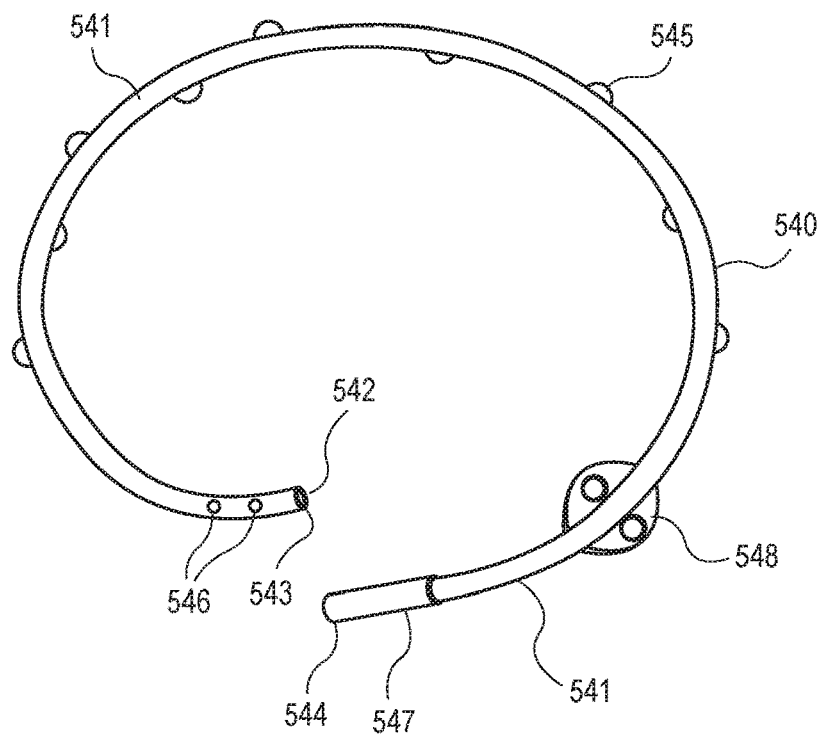
FIG. 22 is a perspective view of the ocular device in one embodiment of this disclosure with tortuous shape.

In another embodiment of this invention, a new ocular device can increase fluid conduit's total length without interfering with patient's field of vision or blocking the trabecular meshwork after the device is implanted in the patient's eye. FIG. 22 shows the perspective view of the ocular device 540, it includes a tortuous body 541 defining a tortuous fluid conduit 542 with a fixed lumen size along the length of the fluid conduit 542, a distal end 543 and a proximal end 544 to allow the aqueous humor to flow from the distal end 543 to the proximal end 544 when it is implanted in the eye 100. There is pressure regulation mechanism such as valve, narrowing or filter in the fluid conduit 542. The body 541 comprises a plurality of retainers 545. The distal end 543 further comprises one or more openings 546 serving as part of the flow pathway to regulate the flow rate of aqueous humor. The one or more openings 546 are configured to promote fluid communication near the flow inlet and prevent clogging of the inlet. The proximal end 544 comprises a compliant tube 547 that is configured to protrude out of the exterior surface of the eyeball 100 through the incision 132 on the eye 100. The compliant tube 547 is flexible to comply with the movement of the eyelid or collapsible under pressure to minimize its profile on the surface of the eye 100 and irritation to the eyelids or eye 100. The one or more suture holes 548 are configured to receive suture, and thereby fixing the ocular device 540 in the eye 100 the implantation. The body 541 of the ocular device 540 is configured with a tortuous shape which can conform generally to the angle 105 of the anterior chamber 106 without blocking the patient's field of vision or the trabecular meshwork 112 when it is implanted. The distal end 543 is configured to be in an angle with the body 541, thereby directing away from the angle 105 of the anterior chamber 106 and the trabecular meshwork 112 when it is implanted in the anterior chamber 106. This can reduce the chance for tissue ingrowth into the fluid conduit 542 and the clogging of the device 540. While the cross section of the ocular device 540 illustrated in this figure is shown as a round shape, it is understood that other shapes of tubular structure may be suitable as well. For example, the cross section of the ocular device 540 may assume an oval, round, square or irregular shape. The retainers 545 on the ocular device 540 are configured to increase the fixation of the device 540 in the eye by creating a higher friction between the ocular device 540 and the eye 100 when it is implanted in the eye 100. In addition, the retainers 545 also serve as spacers between the ocular device 540 and the angle 105 of the anterior chamber 106 to prevent blocking the trabecular meshwork 112. While the ocular device 540 illustrated in this figure is shown as a full-circle shape configured to extend circumferentially around the inner perimeter of the anterior chamber 106, it is understood that other shapes may be suitable as well. For example, the ocular device 1115 may assume a quarter-circle, a half-circle, a three-quarters circle, a full-circle, a five-quarters circle, a two-full-circles, a zig-zag, a spiral, or a helix shape, etc.

Figure 23:
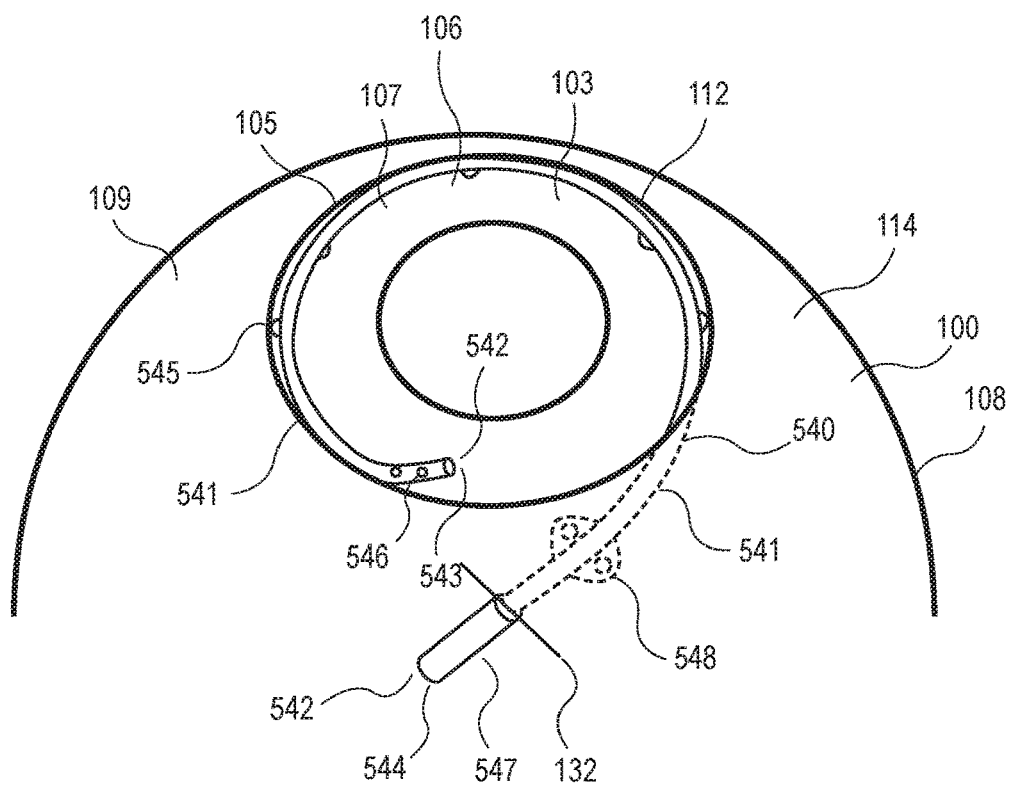
FIG. 23 is a perspective view of an eye showing the cornea, sclera, and iris with the implanted ocular device according to FIG. 22.

FIG. 23 shows the ocular device 540 dimensionally adapted for trans-sclera position after it is implanted in the eye 100. The ocular device 540 includes the tortuous body 541 defining the tortuous fluid conduit 542 with the distal end 543 and the proximal end 544 to allow the aqueous humor to flow from the distal end 543 to the proximal end 544. The compliant tube 547 of the ocular device 540 (shown in solid line) protrudes out of the external surface of the eye 100 through the incision 132 on the eye 100. As shown in this figure, the edge of the compliant tube 547 may be rounded to reduce irritation to the eye 100 and eyelids. While this circular shape of the compliant tube 547 appears particularly advantageous in providing comfort to the eye 100 and minimizing foreign body sensation, other shapes may be designed to provide the same advantages. The compliant tube 547 is flexible to comply with the movement of the eyelid or collapsible under pressure to minimize its profile on the surface of the eye 100 and irritation to the eyelids or eye 100.

Part of the body 541 (shown in dotted line) of the ocular device 540 is configured to be embedded in the sclera 109 of the eye 100. Portion of the body 541 (shown in solid line) is configured to seat in the anterior chamber 106. The body 541 in the anterior chamber 106 comprises a curved shape which extends circumferentially around the inner perimeter of the anterior chamber 106, and conforms generally to the angle 105 of the anterior chamber 106 without blocking the patient's field of vision or the trabecular meshwork 112. The retainers 545 serve as spacers between the ocular device 540 and the angle 105 of the anterior chamber 106 to prevent blocking the trabecular meshwork 112. The distal end 543 is seated in the anterior chamber 106 and is in an angle to the body 541, thereby directing away from the angle 105 of the anterior chamber 106 and the trabecular meshwork 112. The angle between the distal end 543 and the body 541 is within a range from about 10 degree to about 180 degree. The above dimensions and arrangement are exemplary only, and other sizes and arrangements are contemplated. When the ocular device 540 is implanted in the eye 100, it provides IOP relief by draining the aqueous humor from the anterior chamber 106 of the eye 100 to the tear film 108 in a controlled manner as shown in FIG. 23. As a result, this increase in conduit tortuosity can increase the fluid conduit's 542 total length without blocking the patient's field of vision or the trabecular meshwork 112. Alternatively, the ocular device 540 is configured with a curved shape and conformed generally to the ciliary body 102 which lies beneath the iris 103.

This tortuosity in the fluid conduit 542 also increases the fluid conduit's 542 total length without changing the linear distance between the distal end 543 and the proximal end 544 of the fluid conduit 542. As shown in Equation 2, the increase in fluid conduit's 542 total length enables the increase in fluid conduit's 542 lumen size without affecting the device facility and its effectiveness in reducing IOP and preventing hypotony in the eye 100. A large fluid conduit's 542 lumen size can reduce the risk of clogging caused by the debris in the aqueous humor. As discussed previously, a longer fluid conduit 1130 also increases the fluid conduit's 542 ability in impeding the transmission of microorganisms into the anterior chamber 106 by increasing the difficulty for the microorganisms to move against the aqueous humor outflow. In addition, a longer fluid conduit 467 can also provide a larger antimicrobial surface area to further impede the transmission of microorganisms into the anterior chamber 106. The lumen of the fluid conduit 467 comprises a generally round shape. However, it is understood that other lumen shapes may be suitable as well. For example, the lumen shapes of the fluid conduit 467 may be round, oval, rectangular, square, multiple lumens, half-round, half-oval or irregular, etc.

In another embodiment of this invention, this ocular device 540 is surgically implanted in the eye 100 with the compliant tube 547 seated on the external surface of the sclera 109. Alternatively, the ocular device 540 is implanted in the eye 100 with the compliant tube 547 seated on the external surface of the cornea 107. In yet another embodiment of this invention, the ocular device 540 is implanted in the eye 100 with the compliant tube 547 seated on the external surface of the conjunctiva 114.

In one embodiment of this invention, the fluid conduit 542 comprises an enlarged lumen along the length of the fluid conduit 542. The lumen size increases from the distal end 543 to the proximal end 544 to reduce the chance for clogging in the fluid conduit 542 because the enlarged lumen allows the aqueous humor outflow to remove any possible debris deposition in the fluid conduit 542.

Figure 24A:
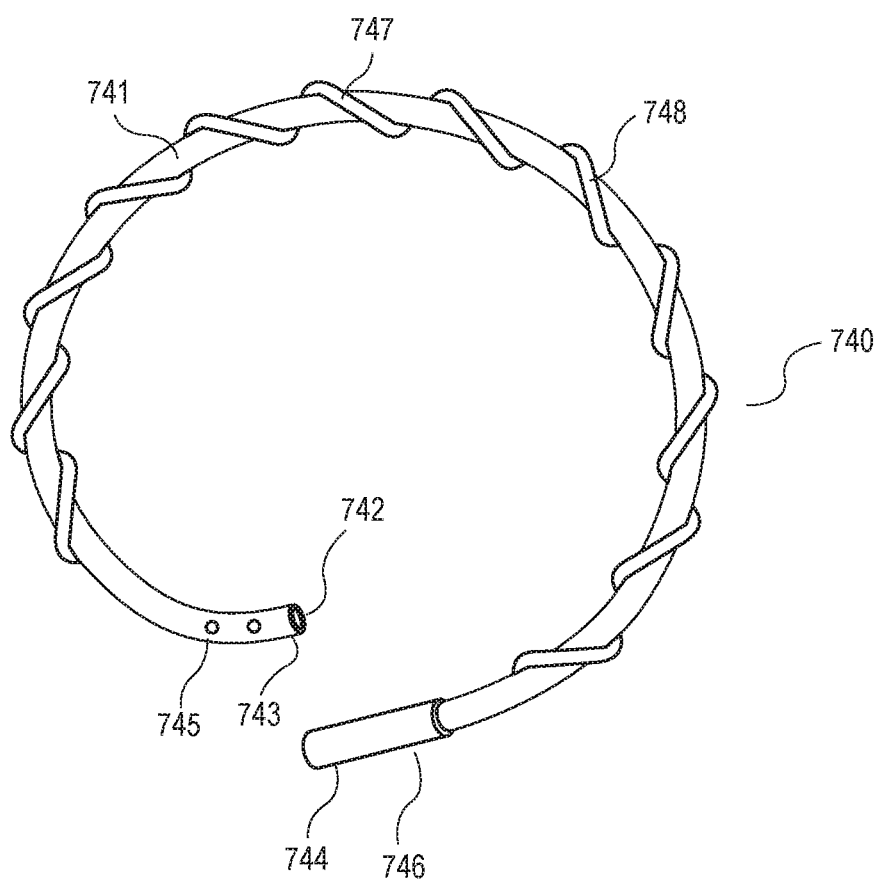
FIG. 24A is a perspective view of the ocular device in another embodiment of this disclosure with "wire shape" retainer on the device.

In further another embodiment of this invention, as shown in FIG. 24a, an ocular device 740 includes a tortuous body 741 defining a tortuous fluid conduit 742 with a fixed lumen size along the length of the fluid conduit 742, a distal end 743 and a proximal end 744 to allow the aqueous humor to flow from the distal end 743 to the proximal end 744. There is pressure regulation mechanism such as valve, narrow section or filter in the fluid conduit 742. The tortuous body 741 of the ocular device 740 is configured to conform generally to the angle 105 of the anterior chamber 106 and extend circumferentially around the inner perimeter of the anterior chamber 106. This increase in conduit tortuosity can also increase the conduit's total length without blocking the patient's field of vision or the trabecular meshwork 112 when it is implanted in the eye 100. The distal end 743 further comprises one or more openings 745 serving as part of the flow pathway to regulate the flow rate of aqueous humor. The one or more openings 745 are configured to promote fluid communication near the flow inlet and prevent clogging of the inlet. The proximal end 744 comprises a compliant tube 746 that is configured to protrude out of the exterior surface of the eyeball 100 through the incision 132 on the eye 100. The compliant tube 746 is flexible to comply with the movement of the eyelid or collapsible under pressure to minimize its profile on the surface of the eye 100 and irritation to the eyelids or eye 100. The ocular device 740 further comprises one or more retainer 747 on the exterior surface of the body 741. The retainer 747 may include, by way of non-limiting example, any number of wire 748 as shown in FIG. 24a. The wire 748 is wrapped around the exterior surface of the body 741 and engages with anterior chamber 106 when it is implanted. The retainer 747 is configured to anchor the device 740 in the eye 100 by introducing a higher friction between the device 740 and the eye 100. In addition, the retainer 747 also serves as spacer between the ocular device 740 and the trabecular meshwork 112 to prevent blocking the angle 105 of the anterior chamber 106 and the trabecular meshwork 112. The wire 748 also reinforces the ocular device 740 so that the ocular device 740 may expand radially and conform generally to the angle 105 of the anterior chamber 106 when it is implanted in the eye 100. The wire 748 may be made of an elastic material such that it is able to be flexed to reduce its cross-sectional profile for fitting into the delivery device, thereby allowing easier penetration through the cornea 107 or sclera 109. While the cross-sectional shape of the wire 748 illustrated in the FIG. 24a is shown as a round shape, it is understood that other cross-sectional shapes to increase friction may be suitable as well. For example, the cross-sectional shape of the wire 748 may be round, oval, cylinder, square, triangular, or irregular, etc. In addition, the wire 748 may be arranged in coaxial, in helix, in irregular or in spiral patterns on the surface of the body 741. The wire 748 can be made by material such as stainless steel, shape memory material, Nitinol, plastic, or metal. The lumen of the fluid conduit 742 comprises a generally round shape. However, it is understood that other lumen shapes may be suitable as well. For example, the lumen shapes of the fluid conduit 742 may be round, oval, rectangular, square, multiple lumens, half-round, half-oval or irregular, etc.

In one embodiment of this invention, the fluid conduit 742 comprises an enlarged lumen along the length of the fluid conduit 742. The lumen size increases from the distal end 743 to the proximal end 744 to reduce the chance for clogging in the fluid conduit 742 because the enlarged lumen allows the aqueous humor outflow to remove any possible debris deposition in the fluid conduit 742.

Figure 24B:
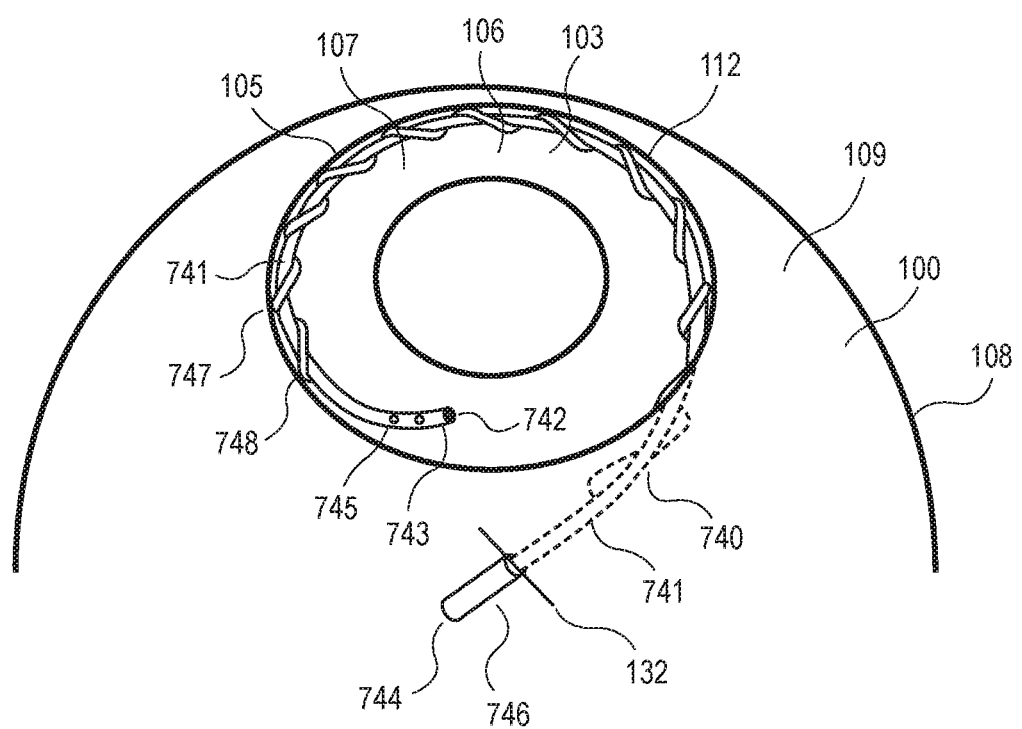
FIG. 24B is a perspective view of the ocular device dimensionally adapted for trans-sclera position in the eye

FIG. 24B shows the ocular device 740 dimensionally adapted for trans-sclera position in the eye 100. The ocular device 740 includes the tortuous body 741 defining the tortuous fluid conduit 742 with a fixed lumen size along the length of the fluid conduit 742, the distal end 743 and the proximal end 744 to allow the aqueous humor to flow from the distal end 743 to the proximal end 744. The compliant tube 746 (shown in solid line) of the ocular device 740 protrudes out of the external surface of the eye 100 through the incision 132 on the eye 100. The compliant tube 746 is flexible to comply with the movement of the eyelid or collapsible under pressure to minimize its profile on the surface of the eye 100 and irritation to the eyelids or eye 100. Part of the body 741 (shown in dotted line) of the ocular device 740 is embedded in the sclera 109 of the eye 100. The distal end 743 (shown in solid line) of the body 741 is seated in the anterior chamber 106. The body 741 in the anterior chamber 106 comprises a curved shape which extends circumferentially around the inner perimeter of the anterior chamber 106, and conforms generally to the angle 105 of the anterior chamber 106 without blocking the patient's field of vision or the trabecular meshwork 112. In addition, the retainer 747 also serves as spacer between the ocular device 740 and the trabecular meshwork 112 to prevent blocking the angle 105 of the anterior chamber 106 and the trabecular meshwork 112. The distal end 743 is also configured to seat in the anterior chamber 106 in an angle to the body 741, thereby directing away from the angle 105 of the anterior chamber 106 and the trabecular meshwork 112. The angle between the distal end 743 and the body 741 is within a range from about 10 degree to about 180 degree. The above dimensions and arrangement are exemplary only, and other sizes and arrangements are contemplated. When the ocular device 740 is implanted in the eye 100, it provides IOP relief by draining the aqueous humor from the anterior chamber 106 of the eye 100 to the tear film 108 in a controlled manner as shown in FIG. 24B. As a result, this increase in conduit tortuosity can increase the fluid conduit's 742 total length without blocking the patient's field of vision or the trabecular meshwork 112.

This tortuosity in the fluid conduit 742 also increases the fluid conduit's 742 total length without changing the linear distance between the distal end 743 and the proximal end 744 of the fluid conduit 742. As shown in Equation 2, the increase in fluid conduit's 742 total length enables the increase in fluid conduit's 742 lumen size without affecting the device facility and its effectiveness in reducing IOP and preventing hypotony in the eye 100. A larger lumen size in the fluid conduit 742 can reduce the risk of clogging caused by the debris in the aqueous humor. As discussed previously, a longer fluid conduit 742 also increases the conduit's ability in impeding the transmission of microorganisms into the anterior chamber 106 by increasing the difficulty for the microorganisms to move against the aqueous humor outflow. In addition, a longer fluid conduit 742 can also provide a larger antimicrobial surface area to further impede the transmission of microorganisms into the anterior chamber 106.

In another embodiment of this invention, an ocular device 800 includes a tortuous body 821 defining a tortuous fluid conduit 830 with a fixed lumen size along the length of the fluid conduit 830, a distal end 820 and a proximal end 822 to allow the aqueous humor to flow from the distal end 820 to the proximal end 822. There is no pressure regulation mechanism such as valve, narrowing or filter in the fluid conduit 830. The body 821 of the ocular device 800 is configured with a tortuous shape which can conform generally to the angle 105 of the anterior chamber 106 and extend circumferentially around the inner perimeter of the anterior chamber 106. This increase in conduit tortuosity can also increase the conduit's total length without blocking the patient's field of vision or the trabecular meshwork when it is implanted in the eye 100. As shown in the FIG. 25a, the fluid conduit 830 is sized to permit drainage of aqueous humor from the anterior chamber 106 to the tear film 108 of the eye 100 when the ocular device 800 is implanted in the cornea 107, limbus 110, sclera 109 or conjunctiva 114. The proximal end 822 comprises a compliant tube 827 that is configured to protrude out of the exterior surface of the cornea 107, sclera 109 or conjunctiva 114 through the incision 132 on the eye 100. The compliant tube 827 is flexible to comply with the movement of the eyelid or collapsible under pressure to minimize its profile on the surface of the eye 100 and irritation to the eyelids or eye 100. The ocular device 800 further comprises an extension 825 configured to extend beyond the distal end 820 of the body 821 and engage with anterior chamber 106 to stabilize the device 800 in the anterior chamber 106. The distal end 820 is configured to seat in the anterior chamber 106 and is in an angle with the body 821, thereby directing away from the trabecular meshwork 112 when it is implanted in the anterior chamber 106. The distal end 820 further comprises one or more openings 829 serving as part of the flow pathway to regulate the flow rate of aqueous humor. The one or more openings 829 are configured to promote fluid communication near the flow inlet and prevent clogging of the inlet. The angulated distal end 820 is configured to discourage the formation of scar tissue on the distal end 820 and prevents clogging of the inlet during the healing of the implant site. The device may also comprise one or more retainers 823 on the exterior surface of the body 821. The lumen of the fluid conduit 830 comprises a generally round shape. However, it is understood that other lumen shapes may be suitable as well. For example, the lumen shapes of the fluid conduit 830 may be round, oval, rectangular, square, multiple lumens, half-round, half-oval or irregular, etc.

In one embodiment of this invention, the fluid conduit 830 comprises an enlarged lumen along the length of the fluid conduit 830. The lumen size increases from the distal end 820 to the proximal end 822 to reduce the chance for clogging in the fluid conduit 830 because the enlarged lumen allows the aqueous humor outflow to remove any possible debris deposition in the fluid conduit 830.

Figure 25A:
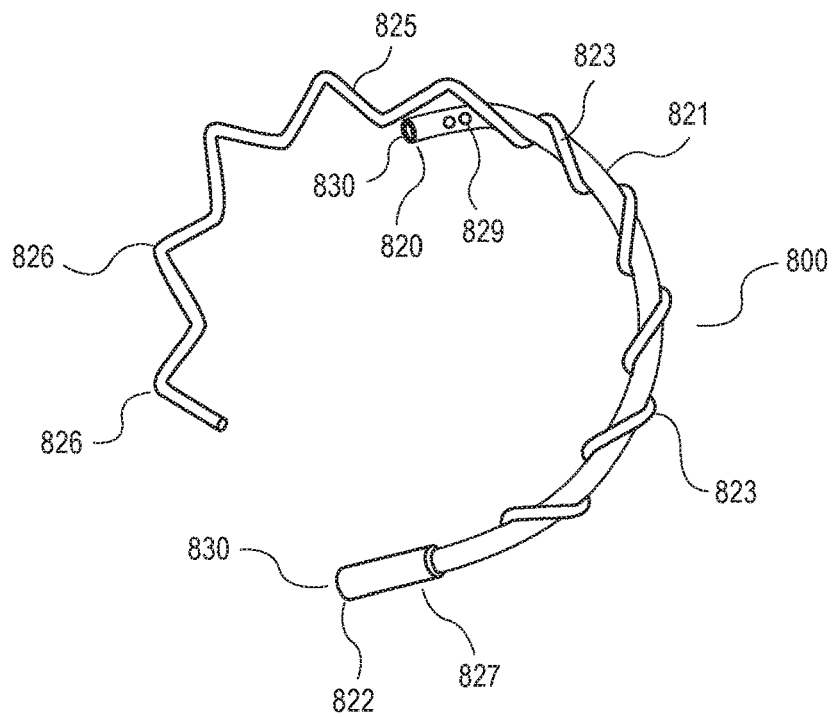
FIG. 25A is a perspective view of the ocular device in another embodiment of this disclosure with "wire shape" retainer and extension on the device.

As shown in the FIG. 25a, the extension 825 is configured to anchor the device 800 in the anterior chamber 106 by introducing a higher radial force to the device 800 and by adding more contact surface between the device 800 and the anterior chamber 106. The longer the extension 825, the higher the anchoring force. The increase in anchoring force is especially advantageous for a device 800 with a body 821 length less than a full circle when it is implanted in the eye 100 and can't extend circumferentially around the entire inner perimeter of the anterior chamber 106. In addition, the extension 825 is also configures to prevent blocking the patient's field of vision and the trabecular meshwork 112 when it is implanted in the eye. As shown in the FIG. 25a, the extension 825 comprises a zig-zag shape with a plurality of apexes 826. The one or more apexes 826 serve as spacers between the extension 825 and the angle 105 of the anterior chamber 106 to prevent blocking the trabecular meshwork 112. While the shape of the extension 825 illustrated in the FIG. 25a is shown as a tortuous zig-zag shape, it is understood that other extension 825 shape to increase contact surface and anchoring force of the device 800 may be suitable as well. For example, the extension 825 may assume a quarter circle, a half circle, a three quarters circle, a full circle, a two-full circles, a zig-zag shape, a spiral shape, a helix shape, a random shape, etc. While the cross-sectional shape of the extension 825 illustrated in the FIG. 25a is shown as a round shape, it is understood that other cross-sectional shape may be suitable as well. For example, the cross-sectional shape of the extension 825 may be round, oval, cylinder, disk, rectangular, or irregular, etc.

Figure 25B:
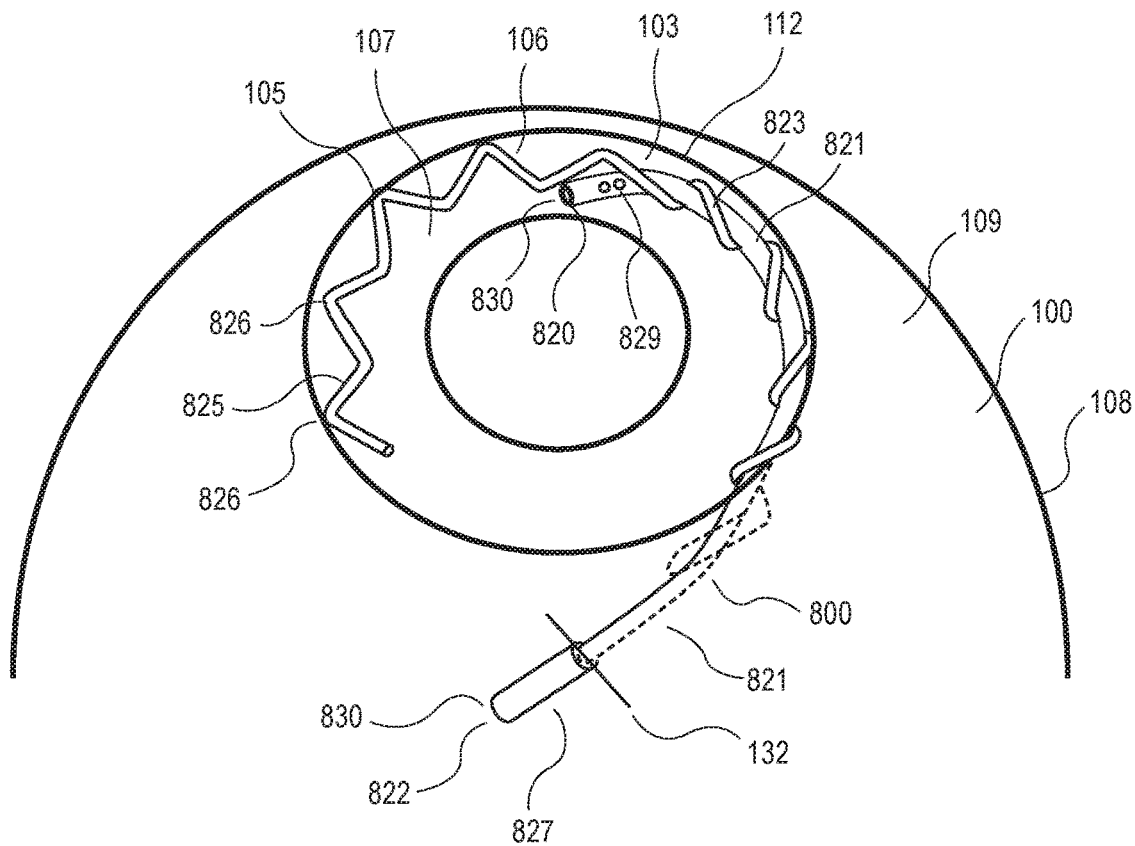
FIG. 25B is a perspective view of the ocular device according to FIG. 25A dimensionally adapted for trans-sclera position in the eye.

FIG. 25b shows the ocular device 800 dimensionally adapted for trans-sclera 109 position in the eye 100. The ocular device 800 includes the tortuous body 821 defining the tortuous fluid conduit 830 with a fixed lumen size along the length of the fluid conduit 830, the distal end 820 and the proximal end 822 to allow the aqueous humor to flow from the distal end 820 to the proximal end 822. The compliant tube 827 of the ocular device 800 (shown in solid line) protrudes out of the external surface of the eye 100 through the incision 132 on the eye 100. The compliant tube 827 is flexible to comply with the movement of the eyelid or collapsible under pressure to minimize its profile on the surface of the eye 100 and irritation to the eyelids or eye 100. Part of the body 821 (shown in dotted line) of the ocular device 800 is embedded in the sclera 109 of the eye 100. The distal end 820 of the body 821 (shown in solid line) is seated in the anterior chamber 106. The portion of the body 821 in the anterior chamber 106 comprises a curved shape which extends circumferentially around the inner perimeter of the anterior chamber 106, and conforms generally to the angle 105 of the anterior chamber 106 without blocking the patient's field of vision or the trabecular meshwork 112. In addition, the retainer 823 also serves as spacer between the ocular device 800 and the trabecular meshwork 112 to prevent blocking the angle 105 of the anterior chamber 106 and the trabecular meshwork 112. The distal end 820 is seated in the anterior chamber 106 and is in an angle to the body 821, thereby directing away from the angle 105 of the anterior chamber 106 and the trabecular meshwork 112. The angle between the distal end 820 and the body 821 is within a range from about 10 degree to about 180 degree. The above dimensions and arrangement are exemplary only, and other sizes and arrangements are contemplated. When the ocular device 800 is implanted in the eye 100, it provides IOP relief by draining the aqueous humor from the anterior chamber 106 of the eye 100 to the tear film 108 in a controlled manner as shown in FIG. 25b. As a result, this increase in conduit tortuosity can increase the fluid conduit's 830 total length without blocking the patient's field of vision or the trabecular meshwork 112.

This tortuosity in the fluid conduit 830 also increases the fluid conduit's 830 total length without changing the linear distance between the distal end 820 and the proximal end 822 of the fluid conduit 830. As shown in Equation 2, the increase in fluid conduit's 830 total length enables the increase in the lumen size of the fluid conduit 830 without affecting the device facility and its effectiveness in reducing IOP and preventing hypotony in the eye 100. A larger lumen size in the fluid conduit 830 can reduce the risk of clogging caused by the debris in the aqueous humor. As discussed previously, a longer fluid conduit 830 also increases the conduit's ability in impeding the transmission of microorganisms into the anterior chamber 106 by increasing the difficulty for the microorganisms to move against the aqueous humor outflow. In addition, a longer fluid conduit 830 can also provide a larger antimicrobial surface area to further impede the transmission of microorganisms into the anterior chamber 106.

Figure 26:
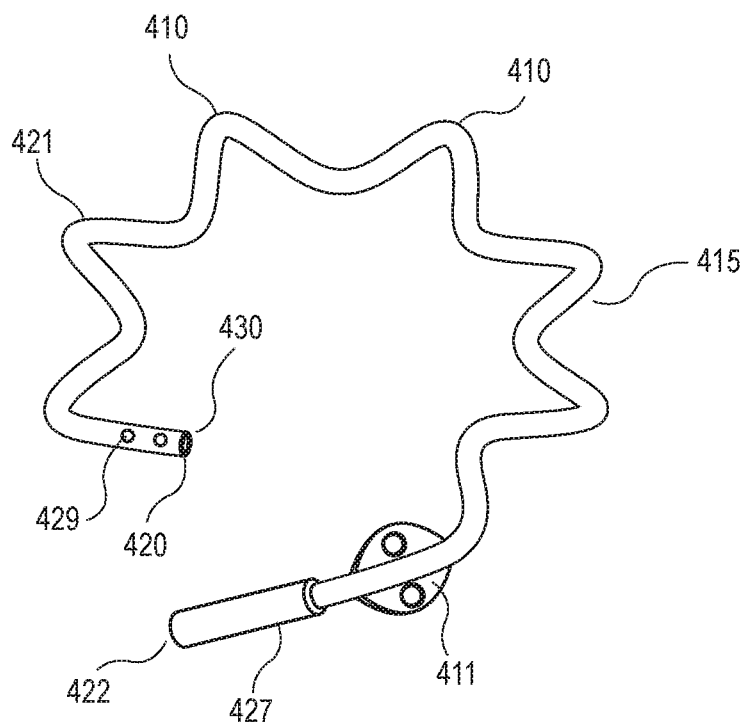
FIG. 26 is a perspective view of the ocular device in another embodiment of this disclosure with tortuous shape.

In yet another embodiment of this invention, an ocular device 415 comprises a tortuous body and a fluid conduit. FIG. 26 shows the perspective view of the ocular device 415, it includes the tortuous body 421 defining the tortuous fluid conduit 430 with a fixed lumen size along the length of the fluid conduit 430, a distal end 420 and a proximal end 422 to allow the aqueous humor to flow from the distal end 420 to the proximal end 422 when it is implanted in the eye 100. There is pressure regulation mechanism such as valve, narrowing or filter in the fluid conduit 430. The distal end 420 is configured to seat in the anterior chamber 106 and is in an angle with the body 421, thereby directing away from the trabecula meshwork 112 when it is implanted in the anterior chamber 106. The distal end 420 further comprises one or more openings 429 serving as part of the flow pathway to regulate the flow rate of aqueous humor. The one or more openings 429 are configured to promote fluid communication near the flow inlet and prevent clogging of the inlet. The angulated distal end 420 is configured to discourage the formation of scar tissue on the distal end 420 and prevents clogging of the inlet during the healing of the implant site. The proximal end 422 comprises a compliant tube 427 that is configured to protrude out of the exterior surface of the eyeball 100 through the incision 132 on the eye 100. The compliant tube 427 is flexible to comply with the movement of the eyelid or collapsible under pressure to minimize its profile on the surface of the eye 100 and irritation to the eyelids or eye 100. The one or more suture holes 411 are configured to receive suture, and thereby fixing the ocular device 415 in the eye 100 during the implantation. The tortuous body 421 and the coupled fluid conduit 430 comprise a generally curved zig-zag shape with one or more apexes 410. The one or more apexes 410 are configured to prevent the body 421 from blocking the patient's field of vision or the trabecular meshwork 112 when it is implanted in the eye 100. The fluid conduit 430 is sized to permit drainage of aqueous humor from the anterior chamber 106 to the tear film 108 of the eye 100 when the ocular device 415 is implanted in the cornea 107, limbus 110, sclera 109 or conjunctiva 114.

Figure 27:
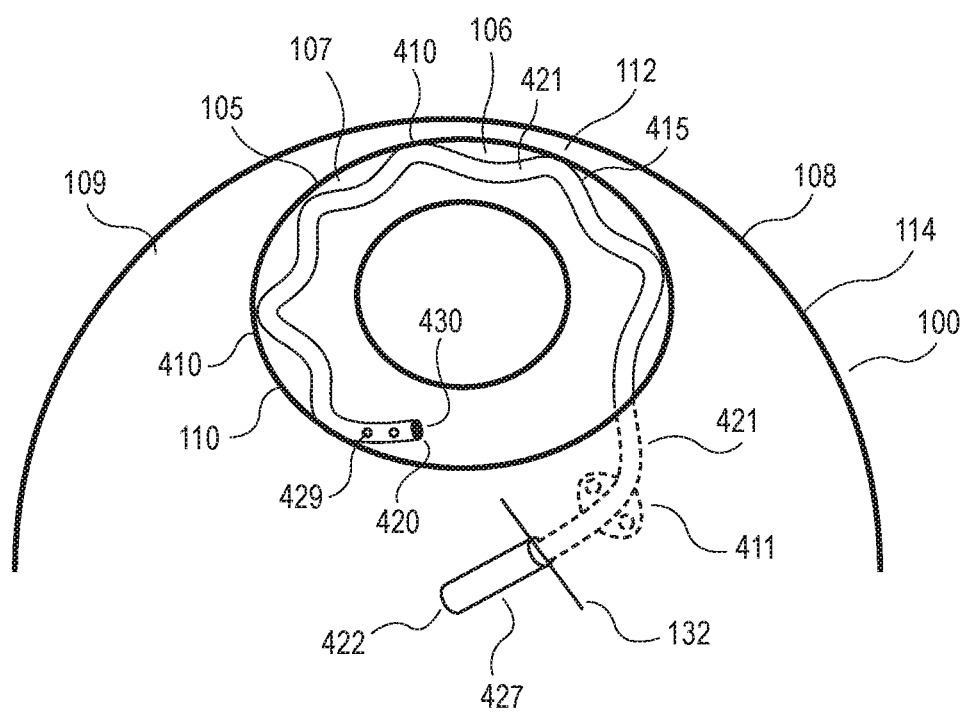
FIG. 27 is a perspective view of an eye showing the cornea, sclera, and iris with the implanted ocular device according to FIG. 26.

As shown in FIG. 27, the body 421 (shown in solid line) of the ocular device 415 conforms generally to the angle 105 of the anterior chamber 106 and extends circumferentially around the inner perimeter of the anterior chamber 106 without blocking the patient's field of vision or the trabecular meshwork 112 in the eye 100. Part of the body 421 (shown in dotted line) of the ocular device 415 is embedded in the sclera 109 of the eye 100. The distal end 420 of the body 421 (shown in solid line) is seated in the anterior chamber 106. In addition, the one or more apexes 410 serve as spacers between the ocular device 415 and the angle 105 of the anterior chamber 106 to prevent blocking the trabecular meshwork 112. The fluid conduit 430 is sized to permit drainage of aqueous humor from the anterior chamber 106 to the tear film 108 of the eye 100 when the ocular device 415 is implanted in the cornea 107, limbus 110, sclera 109 or conjunctiva 114. The compliant tube 427 protrudes out of the exterior surface of the eyeball 100 through the incision 132 on the eye 100. The lumen of the fluid conduit 430 comprises a generally round shape. However, it is understood that other lumen shapes may be suitable as well. For example, the lumen shapes of the fluid conduit 430 may be round, oval, rectangular, square, multiple lumens, half-round, half-oval or irregular, etc.

In one embodiment of this invention, the fluid conduit 430 comprises an enlarged lumen along the length of the fluid conduit 430. The lumen size increases from the distal end 420 to the proximal end 422 to reduce the chance for clogging in the fluid conduit 430 because the enlarged lumen allows the aqueous humor outflow to remove any possible debris deposition in the fluid conduit 430.

While the shape of the ocular device 415 illustrated in the FIGS. 26 and 27 is shown as a tortuous zig-zag shape, it is understood that other tortuous shape may be suitable as well. For example, the ocular device and the coupled flow conduit may assume a quarter circle, a half circle, a three quarters circle, a full circle, two full circles, a zig-zag shape, a spiral shape, a helix shape, a random shape, etc. In addition, the ocular device with a tortuous shape also enhances the fixation of the ocular device in the eye by creating a higher friction between the device and the eye. This increase in conduit tortuosity can also increase the conduit's total length without blocking the iris 103 or the trabecular meshwork 112 when it is implanted in the eye 100.

This tortuosity in the fluid conduit 430 also increases the fluid conduit's 430 total length without changing the linear distance between the distal end 420 and the proximal end 422 of the fluid conduit 430. As shown in Equation 2, the increase in fluid conduit's 430 total length enables the increase in the lumen size of the fluid conduit 430 without affecting the device facility and its effectiveness in reducing IOP and preventing hypotony in the eye 100. A larger lumen size in the fluid conduit 430 can reduce the risk of clogging caused by the debris in the aqueous humor. As discussed previously, a longer fluid conduit 430 also increases the conduit's ability in impeding the transmission of microorganisms into the anterior chamber 106 by increasing the difficulty for the microorganisms to move against the aqueous humor outflow. In addition, a longer fluid conduit 430 can also provide a larger antimicrobial surface area to further impede the transmission of microorganisms into the anterior chamber 106.

Figure 28A:
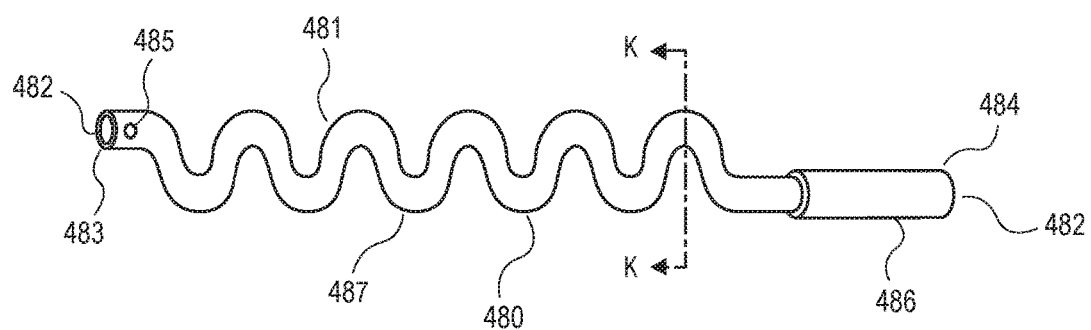
FIG. 28A is a perspective view of the ocular device in accordance with another embodiment of this disclosure with tortuous shape.

As discussed in the previous embodiments, several methods are used to minimum the exposure of the ocular device in the visual field, and thereby preventing the ocular device from interfering the patients' field of vision after the ocular device is implanted in the patients. The ocular device can be implanted circumferentially around the outer perimeter of the anterior chamber 106 in the eye 100. Alternatively, the ocular device can be implanted circumferentially around the inner perimeter of the anterior chamber 106 (above or below the iris 103) without blocking the patients' field of vision or the trabecular meshwork 112. In addition to those, there are several other methods to increase fluid conduit's total length without interfering with patient's field of vision or blocking the trabecular meshwork 112 after the ocular device is implanted in the eye 100. In yet another embodiment of this invention, an ocular device with a tortuous fluid conduit can increase fluid conduit's total length without interfering with patient's field of vision or blocking the trabecular meshwork 112 after the ocular device is implanted in the eye 100. FIG. 28a shows a perspective view of an ocular device 480, the device 480 includes a tortuous body 481 defining a tortuous fluid conduit 482 with a fixed lumen size along the length of the fluid conduit 482, a distal end 483 and a proximal end 484 to allow the aqueous humor to flow from the distal end 483 to the proximal end 484 when it is implanted in the eye 100. There is no pressure regulation mechanism such as valve, narrowing or filter in the fluid conduit 482. The distal end 483 is configured to seat in the anterior chamber 106 and is directing away from the trabecular meshwork 112 when it is implanted in the anterior chamber 106. The distal end 483 further comprises one or more openings 485 serving as part of the flow pathway to regulate the flow rate of aqueous humor. The one or more openings 485 are configured to promote fluid communication near the flow inlet and prevent clogging of the inlet. The proximal end 484 further comprises a compliant tube 486 which is configured to protrude out of the exterior surface of the cornea 107, sclera 109 or conjunctiva 114 and to minimize irritation to the eye 100 or eyelids. The body 481 and the coupled fluid conduit 482 comprise a generally zig-zag shape with one or more apexes 487. The fluid conduit 482 is sized to permit drainage of aqueous humor from the anterior chamber 106 to the tear film 108 of the eye 100 when the ocular device 480 is implanted in the cornea 107, limbus 110, sclera 109 or conjunctiva 114.

Figure 28B:
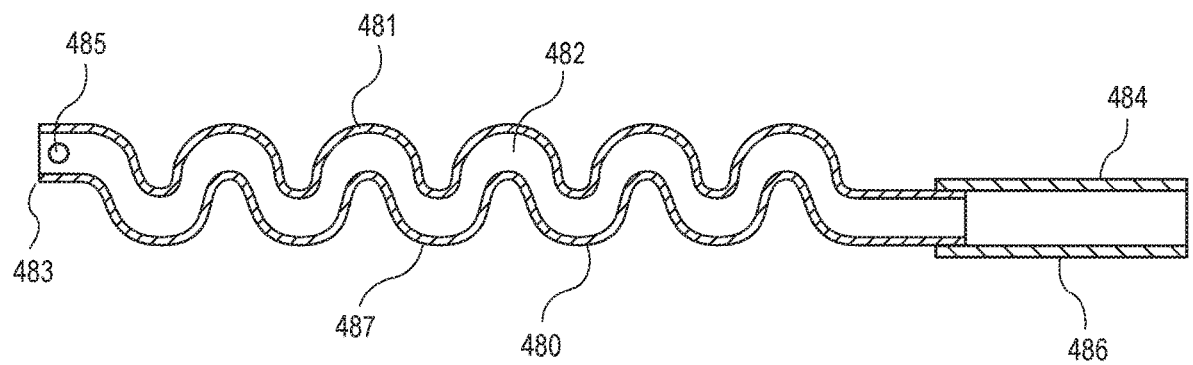
FIG. 28B is a cross sectional view along a central axis of the ocular device according to FIG. 28A.
Figure 28C:
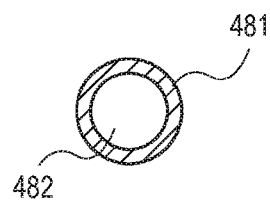
FIG. 28C is a cross sectional view K-K of the ocular device according to FIG. 28A.
Figure 29:
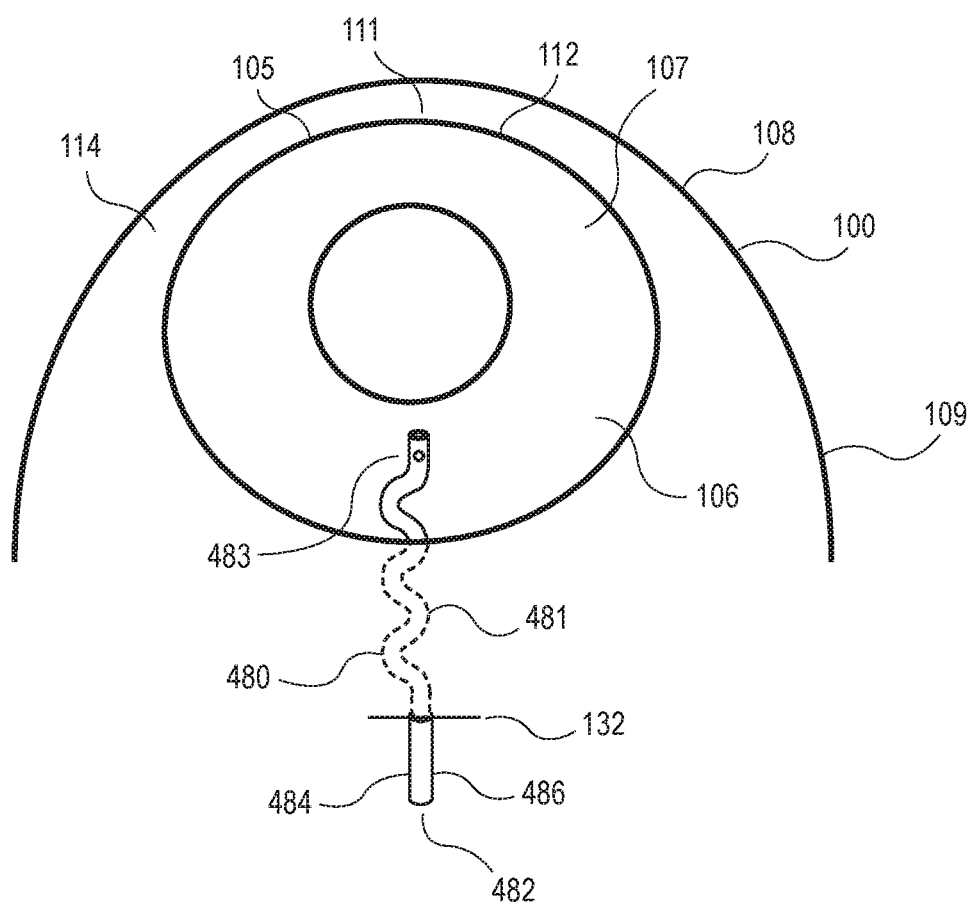
FIG. 29 is a perspective view of an eye showing the cornea, sclera, and iris with the implanted ocular device according to FIG. 28A.

FIG. 28b shows the cross-sectional view of the device 480, the device 480 includes the tortuous body 481 defining the tortuous fluid conduit 482 with a fixed lumen size along the length of the fluid conduit 482, the distal end 483 and the proximal end 484 to allow the aqueous humor to flow from the distal end 483 to the proximal end 484 when it is implanted in the eye 100. There is no valve, narrow section or filter in the fluid conduit 482. FIG. 28c shows the cross-sectional view of the device 480 along Line KK in FIG. 28a. The lumen of the fluid conduit 482 comprises a generally round shape. However, it is understood that other lumen shapes may be suitable as well. For example, the lumen shapes of the fluid conduit 482 may be round, oval, rectangular, square, multiple lumens, half-round, half-oval or irregular, etc. As shown in FIG. 29, the ocular device 480 is implanted in the eye 100. The distal end 483 (shown in solid line) is seated in the anterior chamber 106 pointing away from the trabecular meshwork 112. Portion of the tortuous body 481 (shown in dotted line) is embedded in the sclera 109 of the eye 100. The proximal end 484 comprises the compliant tube 486 (shown in solid line) that is protruded out of the exterior surface of the eyeball 100 through the incision 132. The compliant tube 486 is flexible to comply with the movement of the eyelid or collapsible under pressure to minimize its profile on the surface of the eye 100 and irritation to the eyelids or eye 100. In addition, the ocular device 480 with the tortuous shape also enhances the fixation of the ocular device 480 in the eye 100 by creating a higher friction between the ocular device 480 and the eye 100. As seen in the figure, this increase in fluid conduit's 482 tortuosity can increase the fluid conduit's 482 total length without the risk of interfering with patient's field of vision or blocking the trabecular meshwork 112.

In one embodiment of this invention, the fluid conduit 482 comprises an enlarged lumen along the length of the fluid conduit 482. The lumen size increases from the distal end 483 to the proximal end 484 to reduce the chance for clogging in the fluid conduit 482 because the enlarged lumen allows the aqueous humor outflow to remove any possible debris deposition in the fluid conduit 482.

In another embodiment of this invention, while the linear distance between the distal end 483 and the proximal end 484 remains the same, the increase in fluid conduit's 482 tortuosity increases the fluid conduit's 482 total length. As shown in Equation 2, the ocular device's flow resistance is proportional to the total length of the fluid conduit 482 and is inversely proportional to the fluid conduit's 482 lumen size to the fourth power. While maintaining a sufficient flow resistance to reduce the IOP and avoid hypotony, the increase in fluid conduit's 482 total length allows the increase in fluid conduit's lumen size. The larger lumen size can effectively reduce the chance for clogging caused by the debris in the aqueous humor. The longer total length in the fluid conduit 482 also increases the fluid conduit's 482 ability in impeding the transmission of microorganisms into the anterior chamber 106 by increasing the difficulty for the microorganisms to move against aqueous humor outflow in the long fluid conduit 482. In addition, the longer fluid conduit 482 can also provide a larger antimicrobial surface area to further impede the transmission of microorganisms into the anterior chamber 106. In this invention, the increase in fluid conduit's 482 tortuosity can increase the fluid conduit's 482 total length without affecting the linear distance between the distal end 483 and the proximal end 484, and thereby reducing the risk of interfering with patient's field of vision or blocking the trabecular meshwork 112.

In one embodiment of this invention, while the shape of the ocular device 480 illustrated in the FIGS. 28a and 29 is shown as a tortuous zig-zag shape, it is understood that other tortuous ocular device with tortuous flow conduit to increase flow resistance may be suitable as well.

In one embodiment of this invention, the IOP of the eye 100 can be regulated by the tortuosity of the ocular device implanted in the eye 100. While the linear distance between the distal end and the proximal end remains the same, the increase in fluid conduit's tortuosity increases the fluid conduit's total length. The higher the tortuosity in the fluid conduit, the longer the fluid conduit's total length. As shown in Equation 2, the ocular device's flow resistance is proportional to the total length of the fluid conduit. Because the ocular device's flow resistance is inversely proportional to the device facility, the increase in fluid conduit tortuosity leads to a reduction in device facility. As shown in Equation 6, the IOP of the eye 100 is inversely proportional to the device facility (Ct) of the implanted ocular device. An ocular device with a lower device facility would yield a higher IOP in the eye 100 due to the lower aqueous humor draining efficiency in the implanted ocular device. As a result, the IOP of the eye 100 can be regulated by the tortuosity of the ocular device without using pressure regulation mechanism such as a valve, a filter or a narrowing in the fluid conduit.

A normal IOP (6-22 mmHg) can be maintained by using ocular device with an appropriate fluid conduit tortuosity to reduce IOP and avoid hypotony in the eye 100. However, unlike the tortuous path created by a porous filter described in prior art, the tortuosity in the fluid conduit of this invention does not comprise narrowing that is vulnerable for clogging caused by debris in the aqueous humor.

In yet another embodiment of this invention, while the fluid conduit's total length remains the same, the tortuosity in the fluid conduit can reduce the linear distance between the distal end and the proximal end of the ocular device without affecting the device's aqueous humor draining capacity or device facility. As a consequence, the reduced linear distance between the distal end and the proximal end of the ocular device can also reduce the chance for the device to interfere with patient's field of vision or block the trabecular meshwork.

Figure 30A:
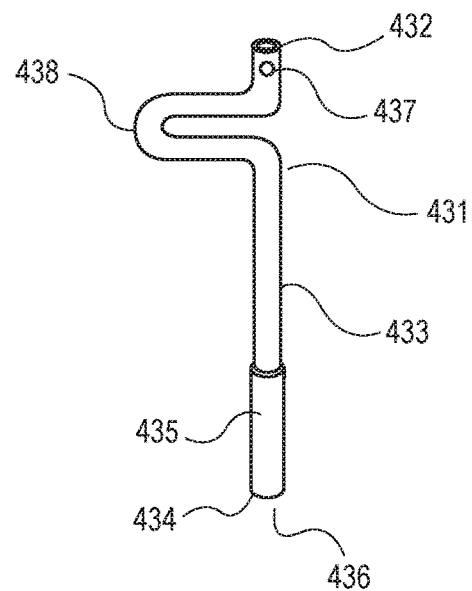
FIG. 30A is a perspective view of an ocular device in accordance with another embodiment of this disclosure with tortuous shape.

In yet another embodiment of this invention, an ocular device includes a tortuous fluid conduit seated in the anterior chamber 106 without interfering with patient's field of vision or blocking the trabecular meshwork 112 after the ocular device is implanted in the eye 100. FIG. 30a shows a perspective view of an ocular device 431, the ocular device 431 includes a tortuous body 433 defining a tortuous fluid conduit 436 with a fixed lumen size along the length of the fluid conduit 436, a distal end 432 and a proximal end 434 to allow the aqueous humor to flow from the distal end 432 to the proximal end 434 when it is implanted in the eye 100. There is no pressure regulation mechanism such as valve, narrowing or filter in the fluid conduit 436. The tortuous fluid conduit 436 is positioned close to the distal end 432 and is configured to seat in the anterior chamber 106 directing away from the trabecular meshwork 112 when it is implanted. The distal end 432 further comprises one or more openings 437 serving as part of the flow pathway to regulate the flow rate of aqueous humor. The one or more openings 437 are configured to promote fluid communication near the flow inlet and prevent clogging of the inlet. The proximal end 434 further comprises a compliant tube 435 which is configured to protrude out of the exterior surface of the cornea 107, sclera 109 or conjunctiva 114 and to minimize irritation to the eye 100 or eyelids. The body 433 and the coupled fluid conduit 436 comprise a zig-zag shape with one or more apexes 438. The fluid conduit 436 is sized to permit drainage of aqueous humor from the anterior chamber 106 to the tear film 108 of the eye 100 when the ocular device 431 is implanted in the cornea 107, limbus 110, sclera 109 or conjunctiva 114. The lumen of the fluid conduit 436 comprises a generally round shape. However, it is understood that other lumen shapes may be suitable as well. For example, the lumen shapes of the fluid conduit 436 may be round, oval, rectangular, square, multiple lumens, half-round, half-oval or irregular, etc.

Figure 30B:
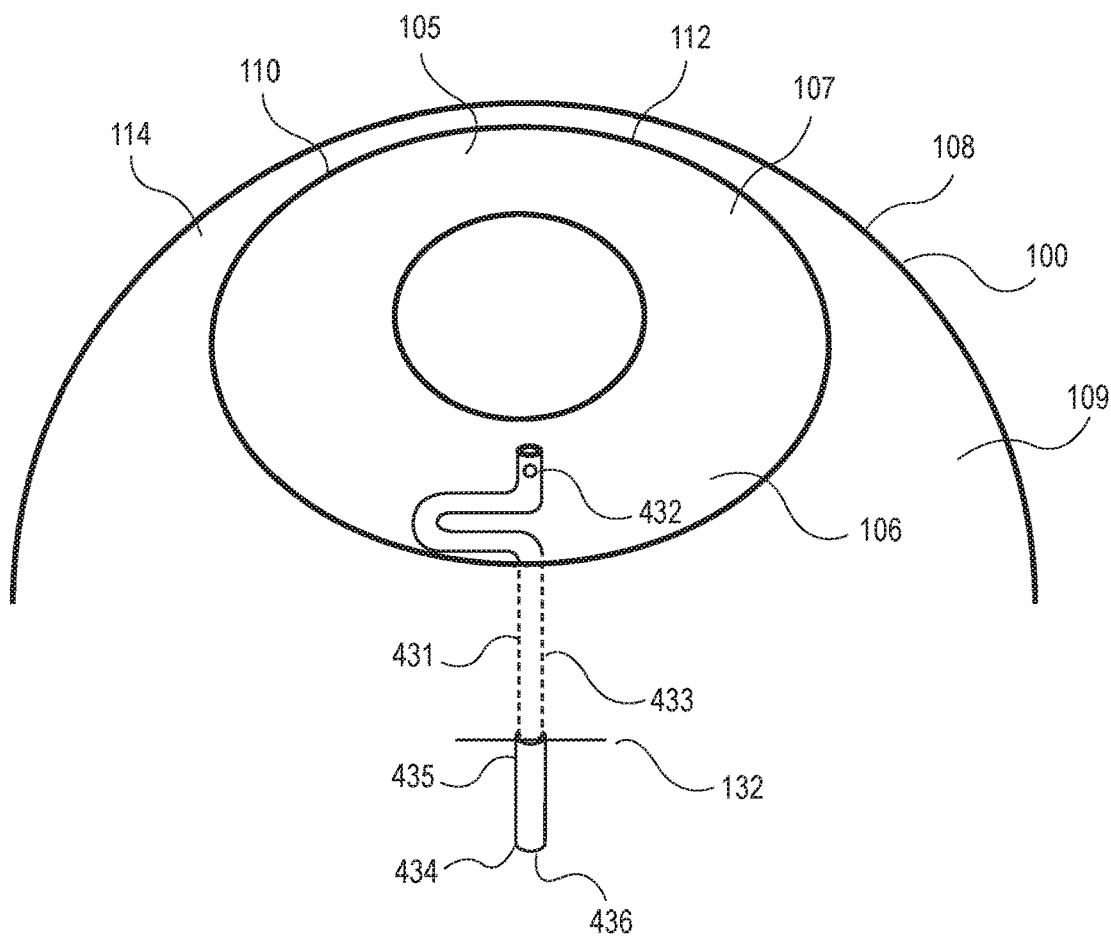
FIG. 30B is a perspective view of an eye showing the cornea, sclera, and iris with the implanted tortuous ocular device according to FIG. 30A.

In another embodiment of this invention, as shown in FIG. 30b, the ocular device 431 is implanted in the eye 100. The ocular device 431 includes the tortuous body 433 defining the tortuous fluid conduit 436 with the distal end 432 and the proximal end 434 to allow the aqueous humor to flow from the distal end 432 to the proximal end 434. The tortuous distal end 432 (shown in solid line) is seated in the anterior chamber 106 and is pointing away from the trabecular meshwork 112. Portion of the body 433 (shown in dotted line) is embedded in the sclera 109 of the eye 100. The proximal end 434 comprises the low-profile compliant tube 435 protruding out of the exterior surface of the eyeball 100 through the incision 132. The low-profile compliant tube 435 is flexible to comply with the movement of the eyelid or collapsible under pressure to minimize its profile on the surface of the eye 100 and irritation to the eyelids or eye 100. The tortuous ocular device 431 also enhances the fixation of the ocular device 431 in the eye 100 by creating a higher friction between the ocular device 431 and the eye 100. This increase in fluid conduit's 436 tortuosity can also increase the fluid conduit's 436 total length without interfering with patient's field of vision or the trabecular meshwork 112 when it is implanted in the eye 100.

This increase in the fluid conduit's 436 tortuosity in the anterior chamber 106 also increases the fluid conduit's 436 total length without changing the linear distance between the distal end 432 and the proximal end 434 of the fluid conduit 436. As shown in Equation 2, the increase in fluid conduit's 436 total length enables the increase in the lumen size of the fluid conduit 436 without affecting the device facility and its effectiveness in reducing IOP and preventing hypotony in the eye 100. A larger lumen size in the fluid conduit 436 can reduce the risk of clogging caused by the debris in the aqueous humor. As discussed previously, a longer fluid conduit 436 also increases the conduit's ability in impeding the transmission of microorganisms into the anterior chamber 106 by increasing the difficulty for the microorganisms to move against the aqueous humor outflow. In addition, a longer fluid conduit 436 can also provide a larger antimicrobial surface area to further impede the transmission of microorganisms into the anterior chamber 106.

In one embodiment of this invention, the fluid conduit 436 comprises an enlarged lumen along the length of the fluid conduit 436. The lumen size increases from the distal end 432 to the proximal end 434 to reduce the chance for clogging in the fluid conduit 436 because the enlarged lumen allows the aqueous humor outflow to remove any possible debris deposition in the fluid conduit 436.

Figure 31A:
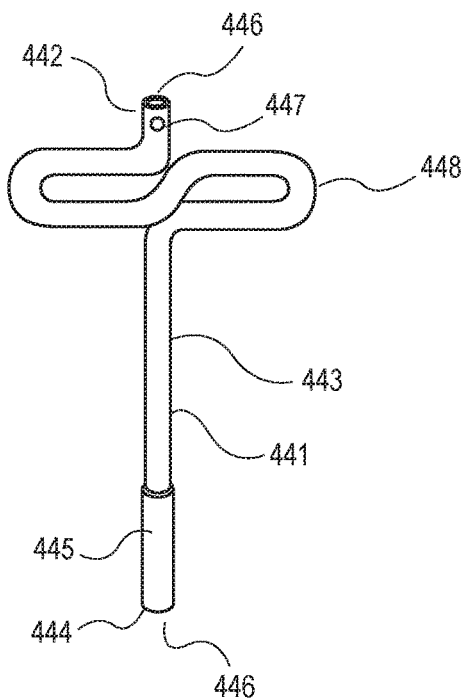
FIG. 31A is a perspective view of an ocular device in accordance with another embodiment of this disclosure with tortuous shape.

In another embodiment of this invention, an ocular device with a tortuous fluid conduit seated in the anterior chamber 106 without interfering with patient's field of vision or blocking the trabecular meshwork 112 after the ocular device is implanted in the patients. FIG. 31a shows a perspective view of the ocular device 441, the device 441 includes a tortuous body 443 defining a tortuous fluid conduit 446 with a fixed lumen size along the length of the fluid conduit 446, a distal end 442 and a proximal end 444 to allow the aqueous humor to flow from the distal end 442 to the proximal end 444 when it is implanted in the eye 100. There is no pressure regulation mechanism such as valve, narrowing or filter in the fluid conduit 446. The tortuous distal end 442 is configured to seat in the anterior chamber 106 and is directing away from the trabecular meshwork 112 when it is implanted in the eye 100. The distal end 442 further comprises one or more openings 447 serving as part of the flow pathway to regulate the flow rate of aqueous humor. The one or more openings 447 are configured to promote fluid communication near the flow inlet and prevent clogging of the inlet. The proximal end 444 further comprises a compliant tube 445 which is configured to protrude out of the exterior surface of the cornea 107, sclera 109 or conjunctiva 114 and to minimize irritation to the eye 100 or eyelids. The body 443 and the coupled fluid conduit 446 comprise a zig-zag shape with one or more apexes 448. The fluid conduit 446 is sized to permit drainage of aqueous humor from the anterior chamber 106 to the tear film 108 of the eye 100 when the ocular device 431 is implanted in the cornea 107, limbus 110, sclera 109 or conjunctiva 114. The lumen of the fluid conduit 446 comprises a generally round shape. However, it is understood that other lumen shapes may be suitable as well. For example, the lumen shapes of the fluid conduit 446 may be round, oval, rectangular, square, multiple lumens, half-round, half-oval or irregular, etc.

Figure 31B:
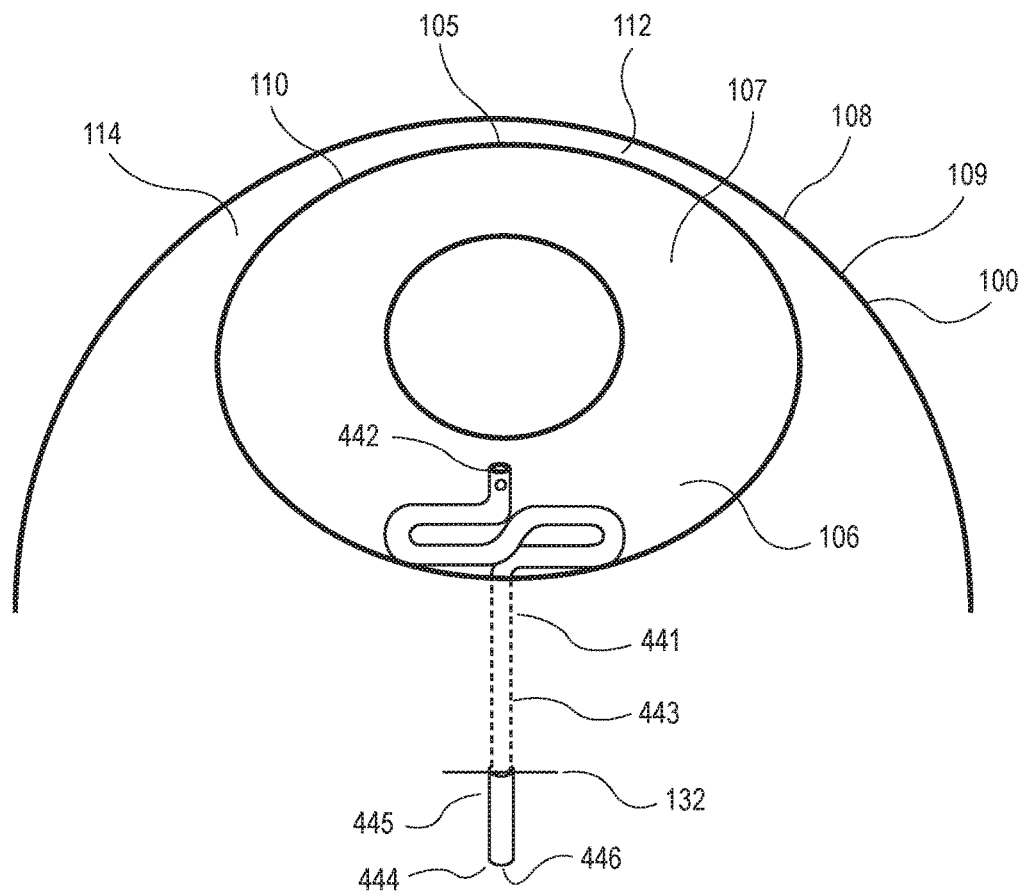
FIG. 31B is a perspective view of an eye showing the cornea, sclera, and iris with the implanted tortuous ocular device according to FIG. 31A.

In one embodiment of this invention, as shown in FIG. 31b, the ocular device 441 is implanted in the eye 100. The ocular device 441 includes the tortuous body 443 defining the tortuous fluid conduit 446 with the distal end 442 and the proximal end 444 to allow the aqueous humor to flow from the distal end 442 to the proximal end 444. The tortuous distal end 442 (shown in solid line) is seated in the anterior chamber 106 pointing away from the trabecular meshwork 112. Portion of the body 443 (shown in dotted line) is embedded in the sclera 109 of the eye 100. The proximal end 444 comprises the low-profile compliant tube 445 that is protruded out of the exterior surface of the eyeball 100 through the incision 132. The low-profile compliant tube 445 is flexible to comply with the movement of the eyelid or collapsible under pressure to minimize its profile on the surface of the eye 100 and irritation to the eyelids or eye 100. The tortuous ocular device 441 also enhances the fixation of the ocular device 441 in the eye 100 by creating a higher friction between the device 441 and the eye 100. This increase in fluid conduit's 446 tortuosity can also increase the fluid conduit's 446 total length without interfering with patient's field of vision or the trabecular meshwork 112 when it is implanted in the eye 100.

This increase in the fluid conduit's 446 tortuosity in the anterior chamber 106 also increases the fluid conduit's 446 total length without changing the linear distance between the distal end 442 and the proximal end 444 of the fluid conduit 446. As shown in Equation 2, the increase in fluid conduit's 446 total length enables the increase in the lumen size of the fluid conduit 446 without affecting the device facility and its effectiveness in reducing IOP and preventing hypotony in the eye 100. A larger lumen size in the fluid conduit 446 can reduce the risk of clogging caused by the debris in the aqueous humor. As discussed previously, a longer fluid conduit 446 also increases the conduit's ability in impeding the transmission of microorganisms into the anterior chamber 106 by increasing the difficulty for the microorganisms to move against the aqueous humor outflow. In addition, a longer fluid conduit 446 can also provide a larger antimicrobial surface area to further impede the transmission of microorganisms into the anterior chamber 106.

In one embodiment of this invention, the fluid conduit 446 comprises an enlarged lumen along the length of the fluid conduit 446. The lumen size increases from the distal end 442 to the proximal end 444 to reduce the chance for clogging in the fluid conduit 446 because the enlarged lumen allows the aqueous humor outflow to remove any possible debris deposition in the fluid conduit 446.

Figure 32:
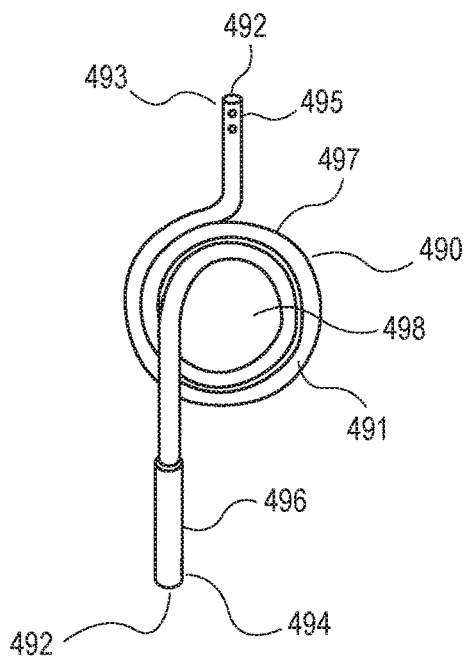
FIG. 32 is a perspective view of a tortuous ocular device disclosed in another embodiment of this disclosure.

In another embodiment of this invention, an ocular device comprises a tortuous fluid conduit in the sclera 109 without interfering with patient's field of vision or blocking the trabecular meshwork 112 after the ocular device is implanted in the eye 100. FIG. 32 shows the perspective view of an ocular device 490, it includes a tortuous body 491 defining a tortuous fluid conduit 492 with a fixed lumen size along the length of the fluid conduit 492, a distal end 493 and a proximal end 494 to allow the aqueous humor to flow from the distal end 493 to the proximal end 494 when it is implanted in the eye 100. There is no pressure regulation mechanism such as valve, narrowing or filter in the fluid conduit 492. The distal end 493 is configured to seat in the anterior chamber 106 and is directing away from the trabecular meshwork 112 when it is implanted in the anterior chamber 106. The distal end 493 further comprises one or more openings 495 serving as part of the flow pathway to regulate the flow rate of aqueous humor. The one or more openings 495 are configured to promote fluid communication near the flow inlet and prevent clogging of the inlet. The proximal end 494 comprises a low-profile compliant tube 496 that is configured to protrude out of the exterior surface of the eyeball 100 through the incision 132. The low-profile compliant tube 496 is flexible to comply with the movement of the eyelid or collapsible under pressure to minimize its profile on the surface of the eye 100 and irritation to the eyelids or eye 100. The tortuous body 491 and the coupled fluid conduit 492 comprise a generally circular shape with one or more circles 497. The center of the circles 497 can serve as a suture hole 498 configured to receive suture during the implantation. The tortuous fluid conduit 492 is sized to permit drainage of aqueous humor from the anterior chamber 106 to the tear film 108 of the eye 100 when the ocular device 490 is implanted in the cornea 107, limbus 110, sclera 109 or conjunctiva 114. The one or more circles 497 in the device 490 are configured to increase the total length and tortuosity of the fluid conduit 492 without increasing the linear distance between the proximal end 494 and distal end 493. This design is also configured to change aqueous humor flow direction in the fluid conduit 492, thereby increasing turbulent flow and flow resistance of the ocular device 490. The lumen of the fluid conduit 492 comprises a generally round shape. However, it is understood that other lumen shapes may be suitable as well. For example, the lumen shapes of the fluid conduit 492 may be round, oval, rectangular, square, multiple lumens, half-round, half-oval or irregular, etc.

Figure 33:
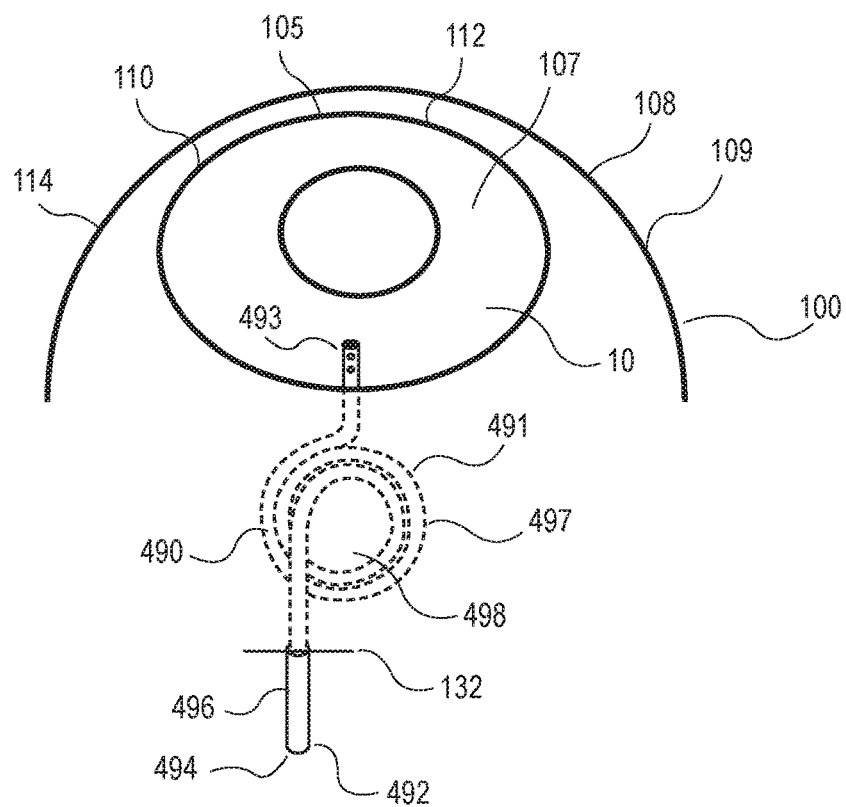
FIG. 33 is a perspective view of an eye showing the cornea, sclera, and iris with the implanted tortuous ocular device according to FIG. 32.

In one embodiment of this invention, as shown in FIG. 33, the ocular device 490 is implanted in the eye 100. The ocular device 490 includes the tortuous body 491 defining the tortuous fluid conduit 492 with the distal end 493 and the proximal end 494 to allow the aqueous humor to flow from the distal end 493 to the proximal end 494. The distal end 493 (shown in solid line) is seated in the anterior chamber 106 pointing away from the trabecular meshwork 112. The tortuous portion of the body 491 (shown in dotted line) is embedded in the sclera 109 of the eye 100. The proximal end 494 comprises a low-profile compliant tube 496 (shown in solid line) that is protruded out of the exterior surface of the eyeball 100 through the incision 132. The low-profile compliant tube 496 is flexible to comply with the movement of the eyelid or collapsible under pressure to minimize its profile on the surface of the eye 100 and irritation to the eyelids or eye 100. The center of the circles 497 can serve as a suture hole 498 to receive suture during the implantation. The tortuous ocular device 490 also enhances the fixation of the ocular device 490 in the eye 100 by creating a higher friction between the ocular device 490 and the eye 100. The tortuous fluid conduit 492 is sized to permit drainage of aqueous humor from the anterior chamber 106 to the tear film 108 of the eye 100 when the ocular device 490 is implanted in the cornea 107, limbus 110, sclera 109 or conjunctiva 114. This increase in fluid conduit's 492 tortuosity can also increase the conduit's total length without interfering with patient's field of vision or the trabecular meshwork 112 when it is implanted in the eye 100.

This increase in the fluid conduit's 492 tortuosity in the sclera 109 also increases the fluid conduit's 492 total length without changing the linear distance between the distal end 493 and the proximal end 494 of the fluid conduit 492. As shown in Equation 2, the increase in fluid conduit's 492 total length enables the increase in the lumen size of the fluid conduit 492 without affecting the device facility and its effectiveness in reducing IOP and preventing hypotony in the eye 100. A larger lumen size in the fluid conduit 492 can reduce the risk of clogging caused by the debris in the aqueous humor. As discussed previously, a longer fluid conduit 492 also increases the conduit's ability in impeding the transmission of microorganisms into the anterior chamber 106 by increasing the difficulty for the microorganisms to move against the aqueous humor outflow. In addition, a longer fluid conduit 492 can also provide a larger antimicrobial surface area to further impede the transmission of microorganisms into the anterior chamber 106.

In one another embodiment of this invention, the tortuous fluid conduit 492 comprises an enlarged lumen along the length of the fluid conduit 492. The lumen size increases from the distal end 493 to the proximal end 494 to reduce the chance for clogging in the fluid conduit 492 because the enlarged lumen allows the aqueous humor outflow to remove any debris deposition in the fluid conduit 492.

In one embodiment of this invention, while the body 491 of the tortuous ocular device 490 illustrated in the FIGS. 32 and 33 is shown as a circular shape, it is understood that other ocular device with tortuous flow conduit to increase the total length in the flow conduit of the ocular device may be suitable as well. For example, the tortuous ocular device with tortuous flow conduit may assume a quarter circle, a half circle, a three quarters circle, a full circle, a two-full circle, a zig-zag shape, a spiral shape, a helix shape, a random shape, etc.

Figure 34:
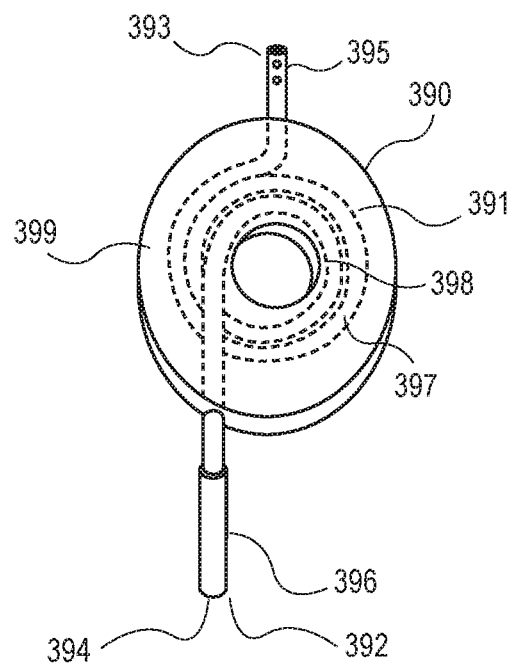
FIG. 34 is a perspective view of the ocular device according to FIG. 32 with a coating or an encapsulation on the device.

In one another embodiment of this invention, the tortuous ocular device is embedded in a coating or a plate. FIG. 34 shows the perspective view of an ocular device 390, it includes a tortuous body 391 defining a tortuous fluid conduit 392 with a fixed lumen size along the length of the fluid conduit 392, a distal end 393 and a proximal end 394 to allow the aqueous humor to flow from the distal end 393 to the proximal end 394 when it is implanted in the eye 100. There is no pressure regulation mechanism such as valve, narrowing or filter in the fluid conduit 392. The distal end 393 is configured to seat in the anterior chamber 106 and is directing away from the trabecular meshwork 112 when it is implanted in the anterior chamber 106. The distal end 393 further comprises one or more openings 395 serving as part of the flow pathway to regulate the flow rate of aqueous humor. The one or more openings 395 are configured to promote fluid communication near the flow inlet and prevent clogging of the inlet. The proximal end 394 comprises a low-profile compliant tube 396 that is configured to protrude out of the exterior surface of the eyeball 100 through the incision 132. The low-profile compliant tube 396 is flexible to comply with the movement of the eyelid or collapsible under pressure to minimize its profile on the surface of the eye 100 and irritation to the eyelids or eye 100. The tortuous body 391 and the coupled fluid conduit 392 comprise a generally circular shape with one or more circles 397. The center of the circles 397 can serve as a suture hole 398 configured to receive suture during the implantation. The tortuous fluid conduit 392 is sized to permit drainage of aqueous humor from the anterior chamber 106 to the tear film 108 of the eye 100 when the ocular device 390 is implanted in the cornea 107, limbus 110, sclera 109 or conjunctiva 114. The tortuous body 391 is embedded in a coating or a plate 399. The coating or the plate 399 is used to bind the tortuous body 391 together, thereby retaining the tortuous configuration of the ocular device 390 and preventing the ocular device 390 from being damaged by the external force. The one or more circles 397 in the ocular device 390 are configured to increase the total length and tortuosity of the fluid conduit 392 without increasing the linear distance between the proximal end 394 and distal end 393. This design is also configured to change aqueous humor flow direction in the fluid conduit 392, thereby increasing turbulent flow and flow resistance of the ocular device 390. The lumen of the fluid conduit 392 comprises a generally round shape. However, it is understood that other lumen shapes may be suitable as well. For example, the lumen shapes of the fluid conduit 392 may be round, oval, rectangular, square, multiple lumens, half-round, half-oval or irregular, etc.

In one embodiment of this invention, while the shape of the plate 399 illustrated in the FIG. 34 is shown as an oval shape, it is understood that other shape to protect the device 390 and restrain the shape of the ocular device 390 may be suitable as well. For example, the plate 399 may assume a circle shape, a square shape, a rectangular shape, or a random shape, etc.

Figure 35:
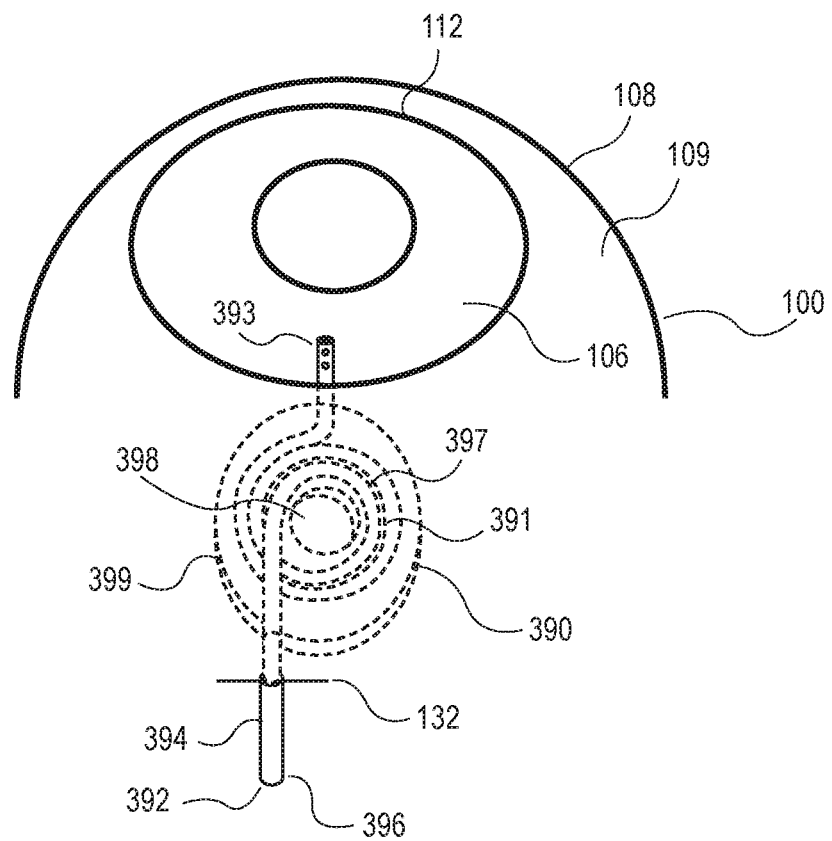
FIG. 35 is a perspective view of an eye showing the cornea, sclera, and iris with the implanted ocular device according to FIG. 34.

In one embodiment of this invention, as shown in FIG. 35, the ocular device 390 is implanted in the eye 100. The distal end 393 (shown in solid line) is seated in the anterior chamber 106 pointing away from the trabecular meshwork 112. The tortuous portion of the body 391 (shown in dotted line) is embedded in the coating or the plate 399 and then implanted in the sclera 109 of the eye 100. The proximal end 394 comprises a low-profile compliant tube 396 (shown in solid line) that is protruded out of the exterior surface of the eyeball 100 through the incision 132. The low-profile compliant tube 396 is flexible to comply with the movement of the eyelid or collapsible under pressure to minimize its profile on the surface of the eye 100 and irritation to the eyelids or eye 100. The center of the circles 397 can serve as a suture hole 398 to receive suture during the implantation. The tortuous fluid conduit 392 is sized to permit drainage of aqueous humor from the anterior chamber 106 to the tear film 108 of the eye 100. This increase in fluid conduit's 392 tortuosity can also increase the conduit's total length without interfering with patient's field of vision or the trabecular meshwork 112 when it is implanted in the eye 100.

In one another embodiment of this invention, the tortuous fluid conduit 392 comprises an enlarged lumen along the length of the fluid conduit 392. The lumen size increases from the distal end 393 to the proximal end 394 to reduce the chance for clogging in the fluid conduit 392 because the enlarged lumen allows the aqueous humor outflow to remove any debris deposition in the fluid conduit 392.

In another embodiment of this invention, the ocular device 390 and the plate 399 are integrated as one part. This integrated part can be fabricated by methods such as laser machining, chemical etching, plasma etching, 3D printing, photo etching, and the like.

In one embodiment of this invention, an ocular device comprises a tortuous fluid conduit in the sclera 109 without interfering with patient's field of vision or blocking the trabecular meshwork 112 after the ocular device is implanted in the patients. FIG. 36 shows the perspective view of an ocular device 580, it includes a tortuous body 581 defining a tortuous fluid conduit 582 with a fixed lumen size along the length of the fluid conduit 582, a distal end 583 and a proximal end 584 to allow the aqueous humor to flow from the distal end 583 to the proximal end 584 when it is implanted in the eye 100. There is no pressure regulation mechanism such as valve, narrowing or filter in the fluid conduit 582. The distal end 583 is configured to seat in the anterior chamber 106 and is directing away from the trabecular meshwork 112 when it is implanted in the anterior chamber 106. The distal end 583 further comprises one or more openings 585 serving as part of the flow pathway to regulate the flow rate of aqueous humor. The one or more openings 585 are configured to promote fluid communication near the flow inlet and prevent clogging of the inlet. The proximal end 584 comprises a low-profile compliant tube 586 that is configured to protrude out of the exterior surface of the eyeball 100 through the incision 132. The low-profile compliant tube 586 is flexible to comply with the movement of the eyelid or collapsible under pressure to minimize its profile on the surface of the eye 100 and irritation to the eyelids or eye 100. The tortuous body 581 and the coupled fluid conduit 582 comprise a generally circular shape with one or more circles 587 side by side. The center of the circles 587 can serve as a suture hole 588 configured to receive suture during the implantation. The tortuous fluid conduit 582 is sized to permit drainage of aqueous humor from the anterior chamber 106 to the tear film 108 of the eye 100 when the ocular device 580 is implanted in the cornea 107, limbus 110, sclera 109 or conjunctiva 114. The one or more circles 587 in the device 580 are configured to increase the total length and tortuosity of the fluid conduit 582 without increasing the linear distance between the proximal end 584 and distal end 583. This design is also configured to change aqueous humor flow direction in the fluid conduit 582, thereby increasing turbulent flow and flow resistance of the ocular device 580. The lumen of the fluid conduit 582 comprises a generally round shape. However, it is understood that other lumen shapes may be suitable as well. For example, the lumen shapes of the fluid conduit 582 may be round, oval, rectangular, square, multiple lumens, half-round, half-oval or irregular, etc.

In one embodiment of this invention, as shown in FIG. 37, the ocular device 580 is implanted in the eye 100. The ocular device 580 includes the tortuous body 581 defining the tortuous fluid conduit 582 with the distal end 583 and the proximal end 584 to allow the aqueous humor to flow from the distal end 583 to the proximal end 584. The distal end 583 (shown in solid line) is seated in the anterior chamber 106 pointing away from the trabecular meshwork 112. The tortuous portion of the body 581 (shown in dotted line) is embedded in the sclera 109 of the eye 100. The proximal end 584 comprises the low-profile compliant tube 586 (shown in solid line) that is protruded out of the exterior surface of the eyeball 100 through the incision 132. The low-profile compliant tube 586 is flexible to comply with the movement of the eyelid or collapsible under pressure to minimize its profile on the surface of the eye 100 and irritation to the eyelids or eye 100. The centers of the one or more circles 587 can serve as suture holes 588 to receive suture during the implantation. The tortuous ocular device 580 also enhances the fixation of the ocular device 580 in the eye 100 by creating a higher friction between the ocular device 580 and the eye 100. The tortuous fluid conduit 582 is sized to permit drainage of aqueous humor from the anterior chamber 106 to the tear film 108 of the eye 100 when the ocular device 580 is implanted in the cornea 107, limbus 110, sclera 109 or conjunctiva 114. This increase in fluid conduit's 582 tortuosity can also increase the conduit's total length without interfering with patient's field of vision or the trabecular meshwork 112 when it is implanted in the eye 100.

This increase in the fluid conduit's 582 tortuosity in the sclera 109 also increases the fluid conduit's 582 total length without changing the linear distance between the distal end 583 and the proximal end 584 of the fluid conduit 582. As shown in Equation 2, the increase in fluid conduit's 582 total length enables the increase in the lumen size of the fluid conduit 582 without affecting the device facility and its effectiveness in reducing IOP and preventing hypotony in the eye 100. A larger lumen size in the fluid conduit 582 can reduce the risk of clogging caused by the debris in the aqueous humor. As discussed previously, a longer fluid conduit 582 also increases the conduit's ability in impeding the transmission of microorganisms into the anterior chamber 106 by increasing the difficulty for the microorganisms to move against the aqueous humor outflow. In addition, a longer fluid conduit 582 can also provide a larger antimicrobial surface area to further impede the transmission of microorganisms into the anterior chamber 106.

In one another embodiment of this invention, the tortuous fluid conduit 582 comprises an enlarged lumen along the length of the fluid conduit 582. The lumen size increases from the distal end 583 to the proximal end 584 to reduce the chance for clogging in the fluid conduit 582 because the enlarged lumen allows the aqueous humor outflow to remove any debris deposition in the fluid conduit 582.

In one another embodiment of this invention, the tortuous ocular device is embedded in a coating or a plate. FIG. 38 shows the perspective view of an ocular device 290, it includes a tortuous body 291 defining a tortuous fluid conduit 292 with a fixed lumen size along the length of the fluid conduit 292, a distal end 293 and a proximal end 294 to allow the aqueous humor to flow from the distal end 293 to the proximal end 294 when it is implanted in the eye 100. There is no pressure regulation mechanism such as valve, narrowing or filter in the fluid conduit 292. The distal end 293 is configured to seat in the anterior chamber 106 and is directing away from the trabecular meshwork 112 when it is implanted in the anterior chamber 106. The distal end 293 further comprises one or more openings 295 serving as part of the flow pathway to regulate the flow rate of aqueous humor. The one or more openings 295 are configured to promote fluid communication near the flow inlet and prevent clogging of the inlet. The proximal end 294 comprises a low-profile compliant tube 296 that is configured to protrude out of the exterior surface of the eyeball 100 through the incision 132. The low-profile compliant tube 296 is flexible to comply with the movement of the eyelid or collapsible under pressure to minimize its profile on the surface of the eye 100 and irritation to the eyelids or eye 100. The tortuous body 291 and the coupled fluid conduit 292 comprise a generally circular shape with one or more circles 297. The center of the one or more circles 297 can serve as a suture holes 298 configured to receive suture during the implantation. The tortuous fluid conduit 292 is sized to permit drainage of aqueous humor from the anterior chamber 106 to the tear film 108 of the eye 100 when the ocular device 290 is implanted in the cornea 107, limbus 110, sclera 109 or conjunctiva 114. The tortuous body 291 is embedded in a coating or a plate 299. The coating or the plate 299 is used to bind the tortuous body 291 together, thereby retaining the tortuous configuration of the ocular device 290 and preventing the ocular device 290 from being damaged by the external force. The one or more circles 297 in the device 290 are configured to increase the total length and tortuosity of the fluid conduit 292 without increasing the linear distance between the proximal end 294 and distal end 293. This design is also configured to change aqueous humor flow direction in the fluid conduit 292, thereby increasing turbulent flow and flow resistance of the ocular device 290. The lumen of the fluid conduit 292 comprises a generally round shape. However, it is understood that other lumen shapes may be suitable as well. For example, the lumen shapes of the fluid conduit 292 may be round, oval, rectangular, square, multiple lumens, half-round, half-oval or irregular, etc.

In another embodiment of this invention, the tortuous fluid conduit 292 comprises an enlarged lumen along the length of the fluid conduit 292. The lumen size increases from the distal end 293 to the proximal end 294 to reduce the chance for clogging in the fluid conduit 292 because the enlarged lumen allows the aqueous humor outflow to remove any debris deposition in the fluid conduit 292.

In one embodiment of this invention, while the shape of the plate 299 illustrated in the FIG. 38 is shown as an oval shape, it is understood that other shape to protect the device 290 and restrain the shape of the ocular device 290 may be suitable as well. For example, the plate 299 may assume a circle shape, a square shape, a rectangular shape, or a random shape, etc.

Figure 39:
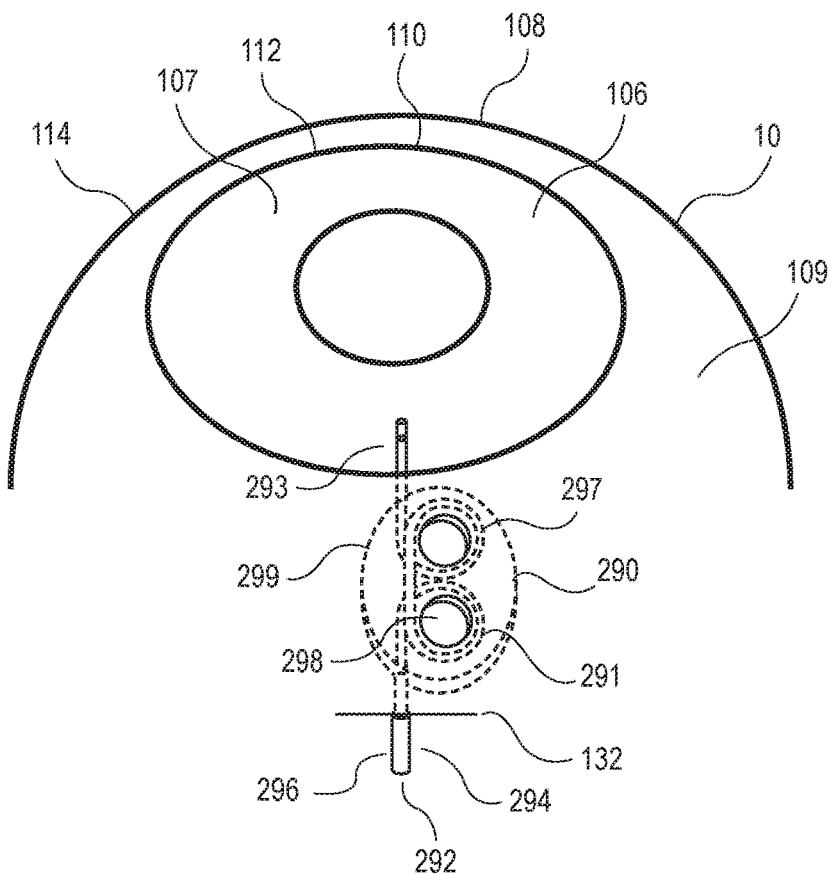
FIG. 39 is a perspective view of an eye showing the cornea, sclera, and iris with the implanted ocular device according to FIG. 38.

In one embodiment of this invention, as shown in FIG. 39, the ocular device 290 is implanted in the eye 100. The distal end 293 (shown in solid line) is seated in the anterior chamber 106 pointing away from the trabecular meshwork 112. The tortuous portion of the body 291 (shown in dotted line) is embedded in the coating or the plate 299 and then implanted in the sclera 109 of the eye 100. The proximal end 294 comprises a low-profile compliant tube 296 (shown in solid line) that is protruded out of the exterior surface of the eyeball 100 through the incision 132. The low-profile compliant tube 296 is flexible to comply with the movement of the eyelid or collapsible under pressure to minimize its profile on the surface of the eye 100 and irritation to the eyelids or eye 100. The center of the circles 297 can serve as a suture hole 298 to receive suture during the implantation. The tortuous fluid conduit 292 is sized to permit drainage of aqueous humor from the anterior chamber 106 to the tear film 108 of the eye 100. This increase in fluid conduit's 292 tortuosity can also increase the conduit's total length without interfering with patient's field of vision or the trabecular meshwork 112 when it is implanted in the eye 100.

In another embodiment of this invention, the ocular device 290 and the plate 299 are integrated as one part. This integrated part can be fabricated by methods such as laser machining, chemical etching, plasma etching, 3D printing, photo etching, and the like.

Figure 40:
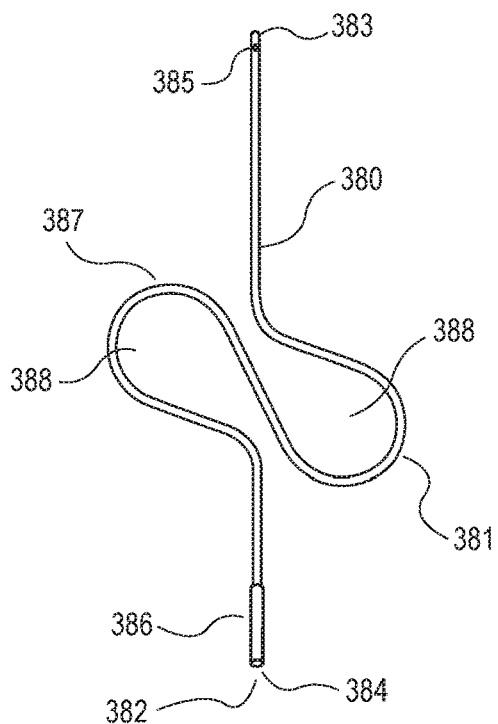
FIG. 40 is a perspective view of a tortuous ocular device described in another embodiment of this disclosure.

In another embodiment of this invention, an ocular device with a tortuous fluid conduit positioned in the sclera 109 without interfering with patient's field of vision or blocking the trabecular meshwork 112 after the ocular device is implanted in the patients. FIG. 40 shows the perspective view of an ocular device 380, it includes a tortuous body 381 defining a tortuous fluid conduit 382 with a fixed lumen size along the length of the fluid conduit 382, a distal end 383 and a proximal end 384 to allow the aqueous humor to flow from the distal end 383 to the proximal end 384 when it is implanted in the eye 100. The distal end 383 is configured to seat in the anterior chamber 106 and is directing away from the trabecular meshwork 112 when it is implanted in the anterior chamber 106. The distal end 383 further comprises one or more openings 385 serving as part of the flow pathway to regulate the flow rate of aqueous humor. The one or more openings 385 are configured to promote fluid communication near the flow inlet and prevent clogging of the inlet. The proximal end 384 comprises a low-profile compliant tube 386 that is configured to protrude out of the exterior surface of the eyeball 100 through the incision 132. The low-profile compliant tube 386 is flexible to comply with the movement of the eyelid or collapsible under pressure to minimize its profile on the surface of the eye 100 and irritation to the eyelids or eye 100. The tortous body 381 and the coupled fluid conduit 382 comprise one or more bends 387 side by side. The center of the bends 387 can serve as a suture hole 388 configured to receive suture during the implantation. The tortuous fluid conduit 382 is sized to permit drainage of aqueous humor from the anterior chamber 106 to the tear film 108 of the eye 100 when the ocular device 380 is implanted in the cornea 107, limbus 110, sclera 109 or conjunctiva 114. The one or more bends 387 in the device 380 are configured to increase the total length and tortuosity of the fluid conduit 382 without increasing the linear distance between the proximal end 384 and distal end 383. This design is also configured to change aqueous humor flow direction in the fluid conduit 382, thereby increasing turbulent flow and flow resistance of the ocular device 380. The lumen of the fluid conduit 382 comprises a generally round shape. However, it is understood that other lumen shapes may be suitable as well. For example, the lumen shapes of the fluid conduit 382 may be round, oval, rectangular, square, multiple lumens, half-round, half-oval or irregular, etc.

In another embodiment of this invention, the tortuous fluid conduit 382 comprises an enlarged lumen along the length of the fluid conduit 382. The lumen size increases from the distal end 383 to the proximal end 384 to reduce the chance for clogging in the fluid conduit 382 because the enlarged lumen allows the aqueous humor outflow to remove any debris deposition in the fluid conduit 382.

In one embodiment of this invention, while the shape of the one or more bends 387 illustrated in the FIG. 40 is shown as a circular shape, it is understood that other shape to increase the total length and tortuosity of the fluid conduit 382 without increasing the linear distance between the proximal end 384 and distal end 383 may be suitable as well. For example, the one or more bends 387 may assume a square shape, a rectangular shape, or a random shape, etc.

In one embodiment of this invention, as shown in FIG. 41, the ocular device 380 is implanted in the eye 100. The ocular device 380 includes the tortuous body 381 defining the tortuous fluid conduit 382 with the distal end 383 and the proximal end 384 to allow the aqueous humor to flow from the distal end 383 to the proximal end 384. The distal end 383 (shown in solid line) is seated in the anterior chamber 106 pointing away from the trabecular meshwork 112. The tortuous portion of the body 381 (shown in dotted line) is embedded in the sclera 109 of the eye 100. The proximal end 384 comprises the low-profile compliant tube 386 (shown in solid line) that is protruded out of the exterior surface of the eyeball 100 through the incision 132. The low-profile compliant tube 386 is flexible to comply with the movement of the eyelid or collapsible under pressure to minimize its profile on the surface of the eye 100 and irritation to the eyelids or eye 100. The centers of the one or more bends 387 can serve as suture holes 388 to receive suture during the implantation. The tortuous ocular device 380 also enhances the fixation of the ocular device 380 in the eye 100 by creating a higher friction between the ocular device 380 and the eye 100. The tortuous fluid conduit 382 is sized to permit drainage of aqueous humor from the anterior chamber 106 to the tear film 108 of the eye 100 when the ocular device 380 is implanted in the cornea 107, limbus 110, sclera 109 or conjunctiva 114. This increase in fluid conduit's 382 tortuosity can also increase the fluid conduit's total length without interfering with patient's field of vision or the trabecular meshwork 112 when it is implanted in the eye 100.

This increase in the fluid conduit's 382 tortuosity in the sclera 109 also increases the fluid conduit's 382 total length without changing the linear distance between the distal end 383 and the proximal end 384 of the fluid conduit 382. As shown in Equation 2, the increase in fluid conduit's 382 total length enables the increase in the lumen size of the fluid conduit 382 without affecting the device facility and its effectiveness in reducing IOP and preventing hypotony in the eye 100. A larger lumen size in the fluid conduit 382 can reduce the risk of clogging caused by the debris in the aqueous humor. As discussed previously, a longer fluid conduit 382 also increases the conduit's ability in impeding the transmission of microorganisms into the anterior chamber 106 by increasing the difficulty for the microorganisms to move against the aqueous humor outflow. In addition, a longer fluid conduit 382 can also provide a larger antimicrobial surface area to further impede the transmission of microorganisms into the anterior chamber 106.

In one another embodiment of this invention, the tortuous ocular device is embedded in a coating or a plate. FIG. 42 shows the perspective view of an ocular device 280, it includes a tortuous body 281 defining a tortuous fluid conduit 282 with a fixed lumen size along the length of the fluid conduit 282, a distal end 283 and a proximal end 284 to allow the aqueous humor to flow from the distal end 283 to the proximal end 284 when it is implanted in the eye 100. There is no pressure regulation mechanism such as valve, narrowing or filter in the fluid conduit 282. The distal end 283 is configured to seat in the anterior chamber 106 and is directing away from the trabecular meshwork 112 when it is implanted in the anterior chamber 106. The distal end 283 further comprises one or more openings 285 serving as part of the flow pathway to regulate the flow rate of aqueous humor. The one or more openings 285 are configured to promote fluid communication near the flow inlet and prevent clogging of the inlet. The proximal end 284 comprises a low-profile compliant tube 286 that is configured to protrude out of the exterior surface of the eyeball 100 through the incision 132. The low-profile compliant tube 286 is flexible to comply with the movement of the eyelid or collapsible under pressure to minimize its profile on the surface of the eye 100 and irritation to the eyelids or eye 100. The tortuous body 281 and the coupled fluid conduit 282 comprise one or more bends 287 (shown in dotted line). The center of the bends 287 can serve as a suture hole 288 configured to receive suture during the implantation. The tortuous fluid conduit 282 is sized to permit drainage of aqueous humor from the anterior chamber 106 to the tear film 108 of the eye 100 when the ocular device 280 is implanted in the cornea 107, limbus 110, sclera 109 or conjunctiva 114. The tortuous body 281 is embedded in a coating or a plate 289. The coating or the plate 289 is used to bind the tortuous body 281 together, thereby retaining the tortuous configuration of the ocular device 280 and preventing the ocular device 280 from being damaged by the external force. The one or more bends 287 in the device 280 are configured to increase the total length and tortuosity of the fluid conduit 282 without increasing the linear distance between the proximal end 284 and distal end 283. This design is also configured to change aqueous humor flow direction in the fluid conduit 282, thereby increasing turbulent flow and flow resistance of the ocular device 280. The lumen of the fluid conduit 282 comprises a generally round shape. However, it is understood that other lumen shapes may be suitable as well. For example, the lumen shapes of the fluid conduit 282 may be round, oval, rectangular, square, multiple lumens, half-round, half-oval or irregular, etc.

In another embodiment of this invention, the tortuous fluid conduit 282 comprises an enlarged lumen along the length of the fluid conduit 282. The lumen size increases from the distal end 283 to the proximal end 284 to reduce the chance for clogging in the fluid conduit 282 because the enlarged lumen allows the aqueous humor outflow to remove any debris deposition in the fluid conduit 282.

In one embodiment of this invention, while the shape of the one or more bends 287 illustrated in the FIG. 42 is shown as a circular shape, it is understood that other shape to increase the total length and tortuosity of the fluid conduit 282 without increasing the linear distance between the proximal end 284 and distal end 283 may be suitable as well. For example, the one or more bends 287 may assume a square shape, a rectangular shape, or a random shape, etc.

In one embodiment of this invention, while the shape of the plate 289 illustrated in the FIG. 42 is shown as an irregular shape, it is understood that other shape to protect the device 280 and restrain the shape of the ocular device 280 may be suitable as well. For example, the plate 289 may assume an oval shape, a circle shape, a square shape, a rectangular shape, or a random shape, etc.

FIG. 43 is a side view of the ocular device 280 with a curved body 281. The curvature is configured to follow the curvature of the eye 100 when the ocular device 280 is implanted in the eye 100.

In one embodiment of this invention, as shown in FIG. 44, the ocular device 280 is implanted in the eye 100. The distal end 283 (shown in solid line) is seated in the anterior chamber 106 pointing away from the trabecular meshwork 112. The tortuous portion of the body 281 (shown in dotted line) is embedded in the coating or the plate 289 and then implanted in the sclera 109 of the eye 100. The proximal end 284 comprises the low-profile compliant tube 296 (shown in solid line) that is protruded out of the exterior surface of the eyeball 100 through the incision 132. The low-profile compliant tube 286 is flexible to comply with the movement of the eyelid or collapsible under pressure to minimize its profile on the surface of the eye 100 and irritation to the eyelids or eye 100. The centers of the one or more bends 287 can serve as suture holes 288 to receive suture during the implantation. The tortuous fluid conduit 282 is sized to permit drainage of aqueous humor from the anterior chamber 106 to the tear film 108 of the eye 100. This increase in fluid conduit's 282 tortuosity can also increase the conduit's total length without interfering with patient's field of vision or the trabecular meshwork 112 when it is implanted in the eye 100.

In another embodiment of this invention, the ocular device 280 and the plate 289 are integrated as one part. The integrated part can be fabricated by methods such as laser machining, chemical etching, plasma etching, 3D printing, photo etching, and the like.

In another embodiment of this invention, an ocular device with a tortuous fluid conduit positioned in the sclera 109 without interfering with patient's field of vision or blocking the trabecular meshwork 112 after the ocular device is implanted in the patients. FIG. 45 shows the perspective view of an ocular device 270, it includes a tortuous body 271 defining a tortuous fluid conduit 272 with a fixed lumen size along the length of the fluid conduit 272, a distal end 273 and a proximal end 274 to allow the aqueous humor to flow from the distal end 273 to the proximal end 274 when it is implanted in the eye 100. There is no pressure regulation mechanism such as valve, narrowing or filter in the fluid conduit 272. The distal end 273 is configured to seat in the anterior chamber 106 and is directing away from the trabecular meshwork 112 when it is implanted in the anterior chamber 106. The distal end 273 further comprises one or more openings 275 serving as part of the flow pathway to regulate the flow rate of aqueous humor. The one or more openings 275 are configured to promote fluid communication near the flow inlet and prevent clogging of the inlet. The proximal end 274 comprises a low-profile compliant tube 276 that is configured to protrude out of the exterior surface of the eyeball 100 through the incision 132. The low-profile compliant tube 276 is flexible to comply with the movement of the eyelid or collapsible under pressure to minimize its profile on the surface of the eye 100 and irritation to the eyelids or eye 100. The tortuous body 271 and the coupled fluid conduit 272 comprise one or more zig-zag 277 side by side. The tortuous fluid conduit 272 is sized to permit drainage of aqueous humor from the anterior chamber 106 to the tear film 108 of the eye 100 when the ocular device 270 is implanted in the cornea 107, limbus 110, sclera 109 or conjunctiva 114. The one or more zig-zag 277 in the device 270 are configured to increase the total length and tortuosity of the fluid conduit 272 without increasing the linear distance between the proximal end 274 and distal end 273. This design is also configured to change aqueous humor flow direction in the fluid conduit 272, thereby increasing turbulent flow and flow resistance of the ocular device 270. The lumen of the fluid conduit 272 comprises a generally round shape. However, it is understood that other lumen shapes may be suitable as well. For example, the lumen shapes of the fluid conduit 272 may be round, oval, rectangular, square, multiple lumens, half-round, half-oval or irregular, etc.

In another embodiment of this invention, the tortuous fluid conduit 272 comprises an enlarged lumen along the length of the fluid conduit 272. The lumen size increases from the distal end 273 to the proximal end 274 to reduce the chance for clogging in the fluid conduit 272 because the enlarged lumen allows the aqueous humor outflow to remove any debris deposition in the fluid conduit 272.

In one embodiment of this invention, as shown in FIG. 46, the ocular device 270 is implanted in the eye 100. The ocular device 270 includes the tortuous body 271 defining the tortuous fluid conduit 272 with the distal end 273 and the proximal end 274 to allow the aqueous humor to flow from the distal end 273 to the proximal end 274. The distal end 273 (shown in solid line) is seated in the anterior chamber 106 pointing away from the trabecular meshwork 112. The tortuous portion of the body 271 (shown in dotted line) is embedded in the sclera 109 of the eye 100. The proximal end 274 comprises the low-profile compliant tube 276 (shown in solid line) that is protruded out of the exterior surface of the eyeball 100 through the incision 132. The low-profile compliant tube 276 is flexible to comply with the movement of the eyelid or collapsible under pressure to minimize its profile on the surface of the eye 100 and irritation to the eyelids or eye 100. The tortuous ocular device 270 also enhances the fixation of the ocular device 270 in the eye 100 by creating a higher friction between the ocular device 270 and the eye 100. The tortuous fluid conduit 272 is sized to permit drainage of aqueous humor from the anterior chamber 106 to the tear film 108 of the eye 100 when the ocular device 270 is implanted in the cornea 107, limbus 110, sclera 109 or conjunctiva 114. This increase in fluid conduit's 272 tortuosity can also increase the fluid conduit's total length without interfering with patient's field of vision or the trabecular meshwork 112 when it is implanted in the eye 100.

This increase in the fluid conduit's 272 tortuosity in the sclera 109 also increases the fluid conduit's 272 total length without changing the linear distance between the distal end 273 and the proximal end 274 of the fluid conduit 272. As shown in Equation 2, the increase in fluid conduit's 272 total length enables the increase in the lumen size of the fluid conduit 272 without affecting the device facility and its effectiveness in reducing IOP and preventing hypotony in the eye 100. A larger lumen size in the fluid conduit 272 can reduce the risk of clogging caused by the debris in the aqueous humor. As discussed previously, a longer fluid conduit 272 also increases the conduit's ability in impeding the transmission of microorganisms into the anterior chamber 106 by increasing the difficulty for the microorganisms to move against the aqueous humor outflow. In addition, a longer fluid conduit 272 can also provide a larger antimicrobial surface area to further impede the transmission of microorganisms into the anterior chamber 106.

Figure 47:
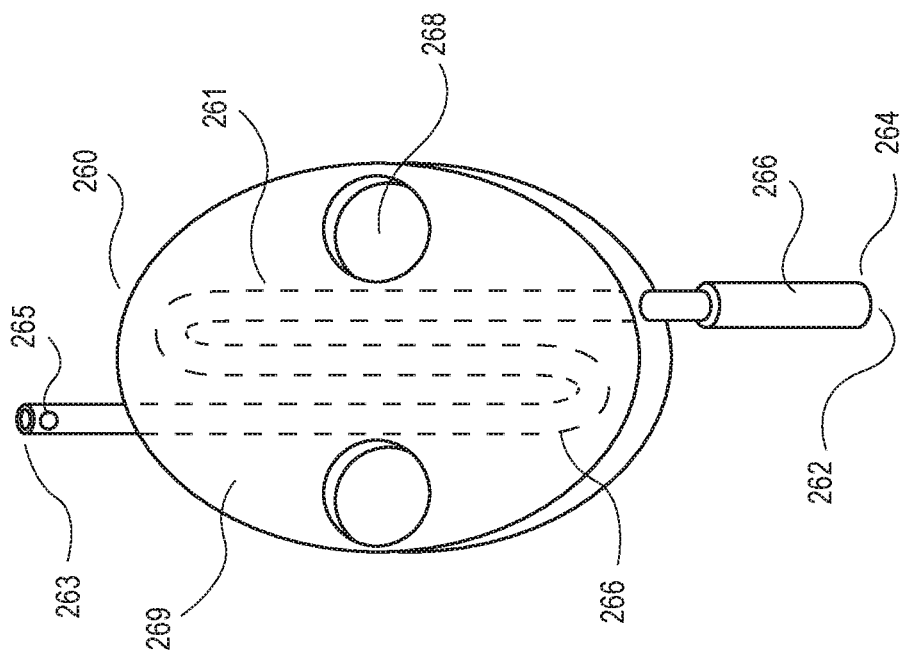
FIG. 47 is a perspective view of the ocular device according to FIG. 45 with a coating or an encapsulation on the device.

In one another embodiment of this invention, the tortuous ocular device is embedded in a coating or a plate. FIG. 47 shows the perspective view of an ocular device 260, it includes a tortuous body 261 defining a tortuous fluid conduit 262 with a fixed lumen size along the length of the fluid conduit 262, a distal end 263 and a proximal end 264 to allow the aqueous humor to flow from the distal end 263 to the proximal end 264 when it is implanted in the eye. There is no valve, narrowing or filter in the fluid conduit 262. The distal end 263 is configured to seat in the anterior chamber 106 and is directing away from the trabecular meshwork 112 when it is implanted in the anterior chamber 106. The distal end 263 further comprises one or more openings 265 serving as part of the flow pathway to regulate the flow rate of aqueous humor. The one or more openings 265 are configured to promote fluid communication near the flow inlet and prevent clogging of the inlet. The proximal end 264 comprises a low-profile compliant tube 266 that is configured to protrude out of the exterior surface of the eyeball 100 through the incision 132. The low-profile compliant tube 266 is flexible to comply with the movement of the eyelid or collapsible under pressure to minimize its profile on the surface of the eye 100 and irritation to the eyelids or eye 100. The tortuous body 261 and the coupled fluid conduit 262 comprise one or more zig-zag 267 (shown in dotted line). The tortuous fluid conduit 262 is sized to permit drainage of aqueous humor from the anterior chamber 106 to the tear film 108 of the eye 100 when the ocular device 260 is implanted in the cornea 107, limbus 110, sclera 109 or conjunctiva 114. The tortuous body 261 is embedded in a coating or a plate 269. The coating or the plate 269 is used to bind the tortuous body 261 together, thereby retaining the tortuous configuration of the ocular device 260 and preventing the ocular device 260 from being damaged by the external force. The one or more suture holes 268 are configured to receive suture, and thereby fixing the ocular device 260 in in the eye 100 during the implantation. The one or more zig-zag 267 in the ocular device 260 are configured to increase the total length and tortuosity of the fluid conduit 262 without increasing the linear distance between the proximal end 264 and distal end 263. This design is also configured to change aqueous humor flow direction in the fluid conduit 262, thereby increasing turbulent flow and flow resistance of the ocular device 260. The lumen of the fluid conduit 262 comprises a generally round shape. However, it is understood that other lumen shapes may be suitable as well. For example, the lumen shapes of the fluid conduit 262 may be round, oval, rectangular, square, multiple lumens, half-round, half-oval or irregular, etc.

In another embodiment of this invention, the tortuous fluid conduit 262 comprises an enlarged lumen along the length of the fluid conduit 262. The lumen size increases from the distal end 263 to the proximal end 264 to reduce the chance for clogging in the fluid conduit 262 because the enlarged lumen allows the aqueous humor outflow to remove any debris deposition in the fluid conduit 262.

In one embodiment of this invention, while the shape of the plate 269 illustrated in the FIG. 47 is shown as an oval shape, it is understood that other shape to protect the device 260 and restrain the shape of the ocular device 260 may be suitable as well. For example, the plate 269 may assume an oval shape, a circle shape, a square shape, a rectangular shape, or a random shape, etc.

Figure 48:
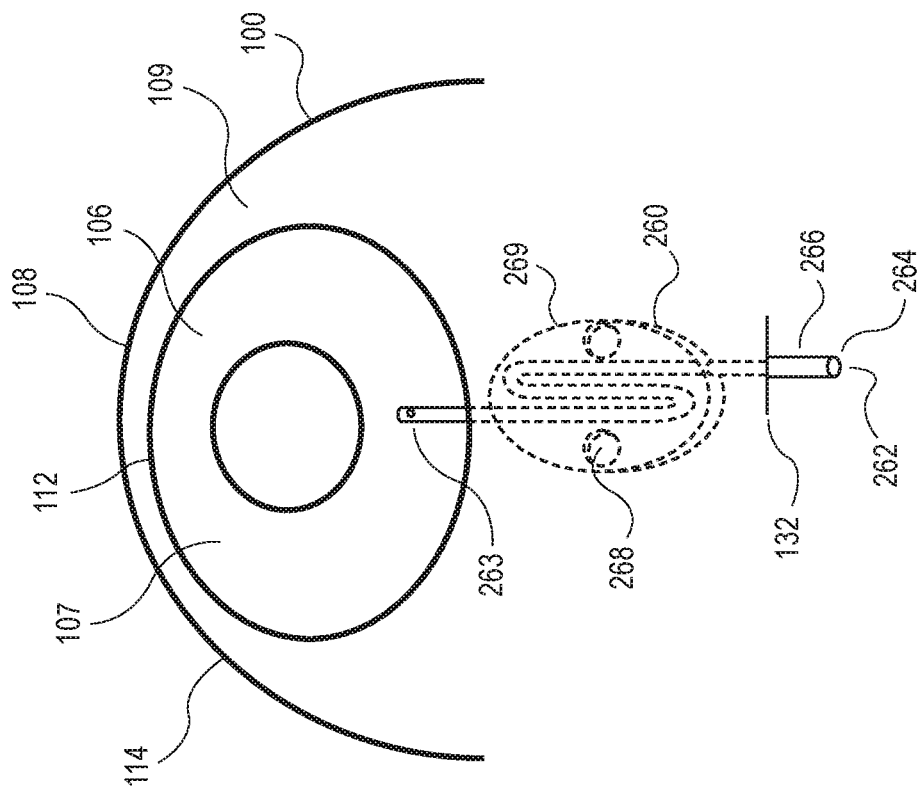
FIG. 48 is a perspective view of an eye showing the cornea, sclera, and iris with the implanted ocular device according to FIG. 47.

In one embodiment of this invention, as shown in FIG. 48, the ocular device 260 is implanted in the eye 100. The distal end 263 (shown in solid line) is seated in the anterior chamber 106 pointing away from the trabecular meshwork 112. The tortuous portion of the body 261 (shown in dotted line) is embedded in the coating or the plate 269 and then implanted in the sclera 109 of the eye 100. The proximal end 264 comprises the low-profile compliant tube 266 (shown in solid line) that is protruded out of the exterior surface of the eyeball 100 through the incision 132. The low-profile compliant tube 266 is flexible to comply with the movement of the eyelid or collapsible under pressure to minimize its profile on the surface of the eye 100 and irritation to the eyelids or eye 100. The one or more suture holes 268 are configured to receive suture, and thereby fixing the ocular device in in the eye 100 during the implantation The tortuous fluid conduit 262 is sized to permit drainage of aqueous humor from the anterior chamber 106 to the tear film 108 of the eye 100. This increase in fluid conduit's 262 tortuosity can also increase the conduit's total length without interfering with patient's field of vision or the trabecular meshwork 112 when it is implanted in the eye 100.

In another embodiment of this invention, the ocular device 260 and the plate 269 are integrated as one part. The integrated part can be fabricated by methods such as laser machining, chemical etching, plasma etching, 3D printing, photo etching, and the like.

Figure 49:
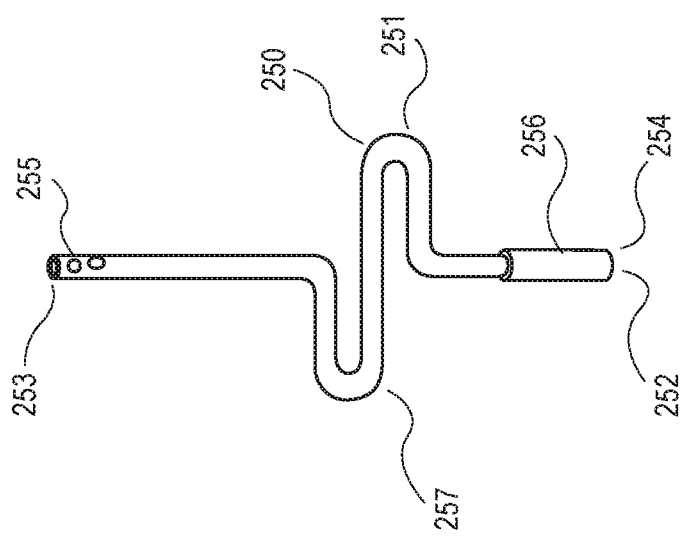
FIG. 49 is a perspective view of a tortuous ocular device described in another embodiment of this disclosure.

In further another embodiment of this invention, an ocular device with a tortuous fluid conduit positioned in the sclera 109 without interfering with patient's field of vision or blocking the trabecular meshwork 112 after the ocular device is implanted in the patients. FIG. 49 shows the perspective view of an ocular device 250, it includes a tortuous body 251 defining a tortuous fluid conduit 252 with a fixed lumen size along the length of the fluid conduit 252, a distal end 253 and a proximal end 254 to allow the aqueous humor to flow from the distal end 253 to the proximal end 254 when it is implanted in the eye 100. There is no valve, narrowing or filter in the fluid conduit 252. The distal end 253 is configured to seat in the anterior chamber 106 and is directing away from the trabecular meshwork 112 when it is implanted in the anterior chamber 106. The distal end 253 further comprises one or more openings 255 serving as part of the flow pathway to regulate the flow rate of aqueous humor. The one or more openings 255 are configured to promote fluid communication near the flow inlet and prevent clogging of the inlet. The proximal end 254 comprises a low-profile compliant tube 256 that is configured to protrude out of the exterior surface of the eyeball 100 through the incision 132. The low-profile compliant tube 256 is flexible to comply with the movement of the eyelid or collapsible under pressure to minimize its profile on the surface of the eye 100 and irritation to the eyelids or eye 100. The tortuous body 251 and the coupled fluid conduit 252 comprise one or more zig-zag 257 side by side. The tortuous fluid conduit 252 is sized to permit drainage of aqueous humor from the anterior chamber 106 to the tear film 108 of the eye 100 when the ocular device 250 is implanted in the cornea 107, limbus 110, sclera 109 or conjunctiva 114. The one or more zig-zag 257 in the device 250 are configured to increase the total length and tortuosity of the fluid conduit 252 without increasing the linear distance between the proximal end 254 and distal end 253. This design is also configured to change aqueous humor flow direction in the fluid conduit 252, thereby increasing turbulent flow and flow resistance of the ocular device 250. The lumen of the fluid conduit 252 comprises a generally round shape. However, it is understood that other lumen shapes may be suitable as well. For example, the lumen shapes of the fluid conduit 252 may be round, oval, rectangular, square, multiple lumens, half-round, half-oval or irregular, etc.

In another embodiment of this invention, the tortuous fluid conduit 252 comprises an enlarged lumen along the length of the fluid conduit 252. The lumen size increases from the distal end 253 to the proximal end 254 to reduce the chance for clogging in the fluid conduit 252 because the enlarged lumen allows the aqueous humor outflow to remove any debris deposition in the fluid conduit 252.

Figure 50:
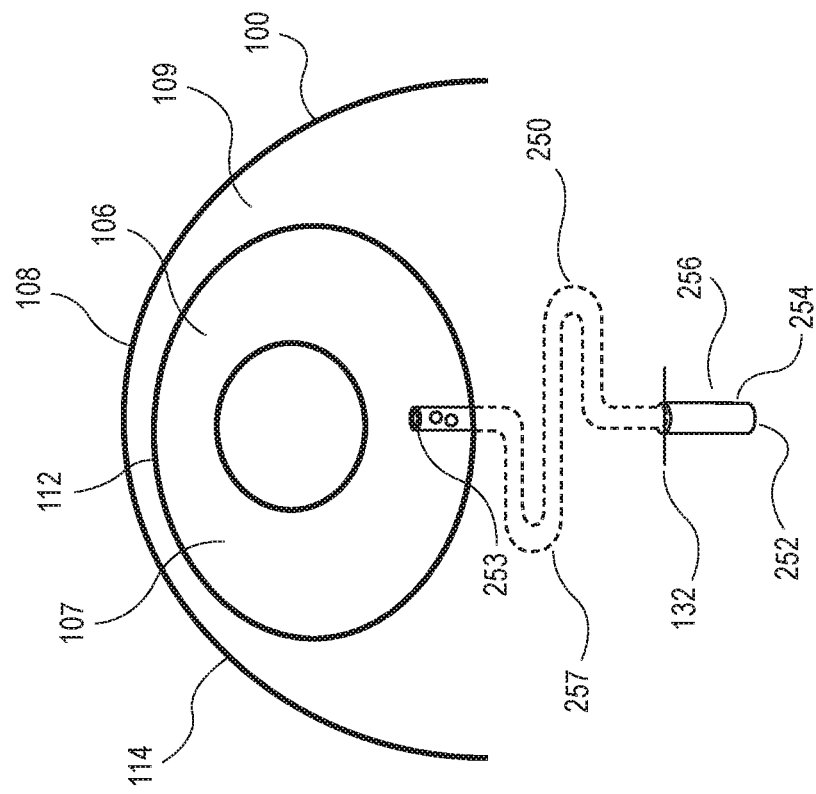
FIG. 50 is a perspective view of an eye showing the cornea, sclera, and iris with the implanted ocular device according to FIG. 49.

In one embodiment of this invention, as shown in FIG. 50, the ocular device 250 is implanted in the eye 100. The ocular device 250 includes the tortuous body 251 defining the tortuous fluid conduit 252 with the distal end 253 and the proximal end 254 to allow the aqueous humor to flow from the distal end 253 to the proximal end 254. The distal end 253 (shown in solid line) is seated in the anterior chamber 106 pointing away from the trabecular meshwork 112. The tortuous portion of the body 251 (shown in dotted line) is embedded in the sclera 109 of the eye 100. The proximal end 254 comprises a low-profile compliant tube 256 (shown in solid line) that is protruded out of the exterior surface of the eyeball 100 through the incision 132. The low-profile compliant tube 256 is flexible to comply with the movement of the eyelid or collapsible under pressure to minimize its profile on the surface of the eye 100 and irritation to the eyelids or eye 100. The tortuous ocular device 250 also enhances the fixation of the ocular device 250 in the eye 100 by creating a higher friction between the ocular device 250 and the eye 100. The tortuous fluid conduit 252 is sized to permit drainage of aqueous humor from the anterior chamber 106 to the tear film 108 of the eye 100 when the ocular device 250 is implanted in the cornea 107, limbus 110, sclera 109 or conjunctiva 114. This increase in fluid conduit's 252 tortuosity can also increase the fluid conduit's total length without interfering with patient's field of vision or the trabecular meshwork 112 when it is implanted in the eye 100.

This increase in the fluid conduit's 252 tortuosity in the sclera 109 also increases the fluid conduit's 252 total length without changing the linear distance between the distal end 253 and the proximal end 254 of the fluid conduit 252. As shown in Equation 2, the increase in fluid conduit's 252 total length enables the increase in the lumen size of the fluid conduit 252 without affecting the device facility and its effectiveness in reducing IOP and preventing hypotony in the eye 100. A larger lumen size in the fluid conduit 252 can reduce the risk of clogging caused by the debris in the aqueous humor. As discussed previously, a longer fluid conduit 252 also increases the conduit's ability in impeding the transmission of microorganisms into the anterior chamber 106 by increasing the difficulty for the microorganisms to move against the aqueous humor outflow. In addition, a longer fluid conduit 252 can also provide a larger antimicrobial surface area to further impede the transmission of microorganisms into the anterior chamber 106.

Figure 51:
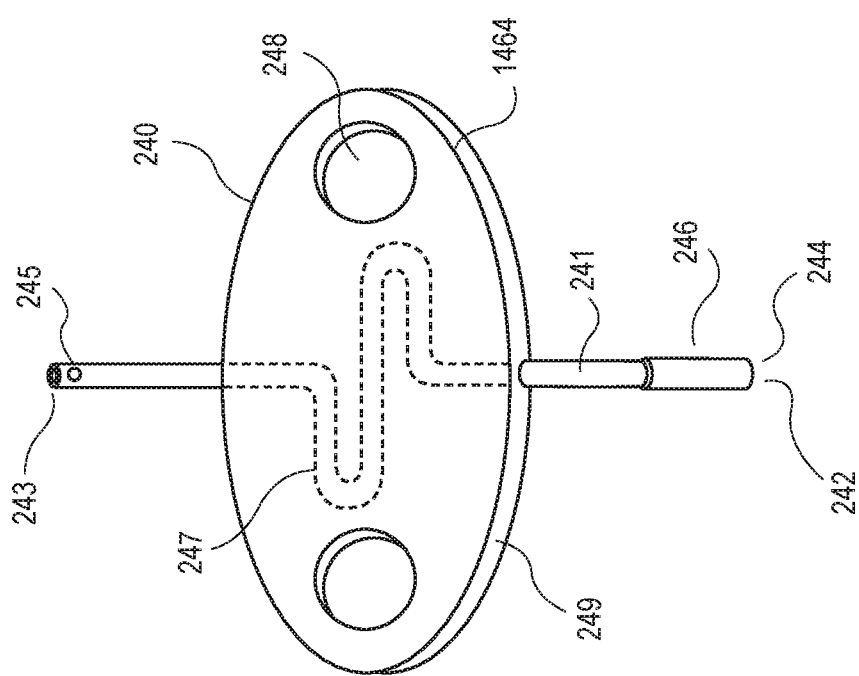
FIG. 51 is a perspective view of the ocular device according to FIG. 49 with a coating or an encapsulation on the device.

In one another embodiment of this invention, the tortuous ocular device is embedded in a coating or a plate. FIG. 51 shows the perspective view of an ocular device 240, it includes a tortuous body 241 defining a tortuous fluid conduit 242 with a fixed lumen size along the length of the fluid conduit 242, a distal end 243 and a proximal end 244 to allow the aqueous humor to flow from the distal end 243 to the proximal end 244 when it is implanted in the eye 100. There is no valve, narrowing or filter in the fluid conduit 242. The distal end 243 is configured to seat in the anterior chamber 106 and is directing away from the trabecular meshwork 112 when it is implanted in the anterior chamber 106. The distal end 243 further comprises one or more openings 245 serving as part of the flow pathway to regulate the flow rate of aqueous humor. The one or more openings 245 are configured to promote fluid communication near the flow inlet and prevent clogging of the inlet. The proximal end 244 comprises a low-profile compliant tube 246 that is configured to protrude out of the exterior surface of the eyeball 100 through the incision 132. The low-profile compliant tube 246 is flexible to comply with the movement of the eyelid or collapsible under pressure to minimize its profile on the surface of the eye 100 and irritation to the eyelids or eye 100. The tortuous body 241 and the coupled fluid conduit 242 comprise one or more zig-zag 247 (shown in dotted line). The tortuous fluid conduit 242 is sized to permit drainage of aqueous humor from the anterior chamber 106 to the tear film 108 of the eye 100 when the ocular device 240 is implanted in the cornea 107, limbus 110, sclera 109 or conjunctiva 114. The tortuous body 241 is embedded in a coating or a plate 249. The coating or the plate 249 is used to bind the tortuous body 241 together, thereby retaining the tortuous configuration of the ocular device 240 and preventing the ocular device 240 from being damaged by the external force. The one or more suture holes 248 are configured to receive suture, and thereby fixing the ocular device 240 in in the eye 100 during the implantation. The one or more zig-zag 247 in the ocular device 240 are configured to increase the total length and tortuosity of the fluid conduit 242 without increasing the linear distance between the proximal end 244 and distal end 243. This design is also configured to change aqueous humor flow direction in the fluid conduit 242, thereby increasing turbulent flow and flow resistance of the ocular device 240. The lumen of the fluid conduit 242 comprises a generally round shape. However, it is understood that other lumen shapes may be suitable as well. For example, the lumen shapes of the fluid conduit 242 may be round, oval, rectangular, square, multiple lumens, half-round, half-oval or irregular, etc.

In another embodiment of this invention, the tortuous fluid conduit 242 comprises an enlarged lumen along the length of the fluid conduit 242. The lumen size increases from the distal end 243 to the proximal end 244 to reduce the chance for clogging in the fluid conduit 242 because the enlarged lumen allows the aqueous humor outflow to remove any debris deposition in the fluid conduit 242.

In one embodiment of this invention, while the shape of the plate 249 illustrated in the FIG. 51 is shown as an oval shape, it is understood that other shape to protect the device 240 and restrain the shape of the ocular device 240 may be suitable as well. For example, the plate 249 may assume an oval shape, a circle shape, a square shape, a rectangular shape, or a random shape, etc.

Figure 52:
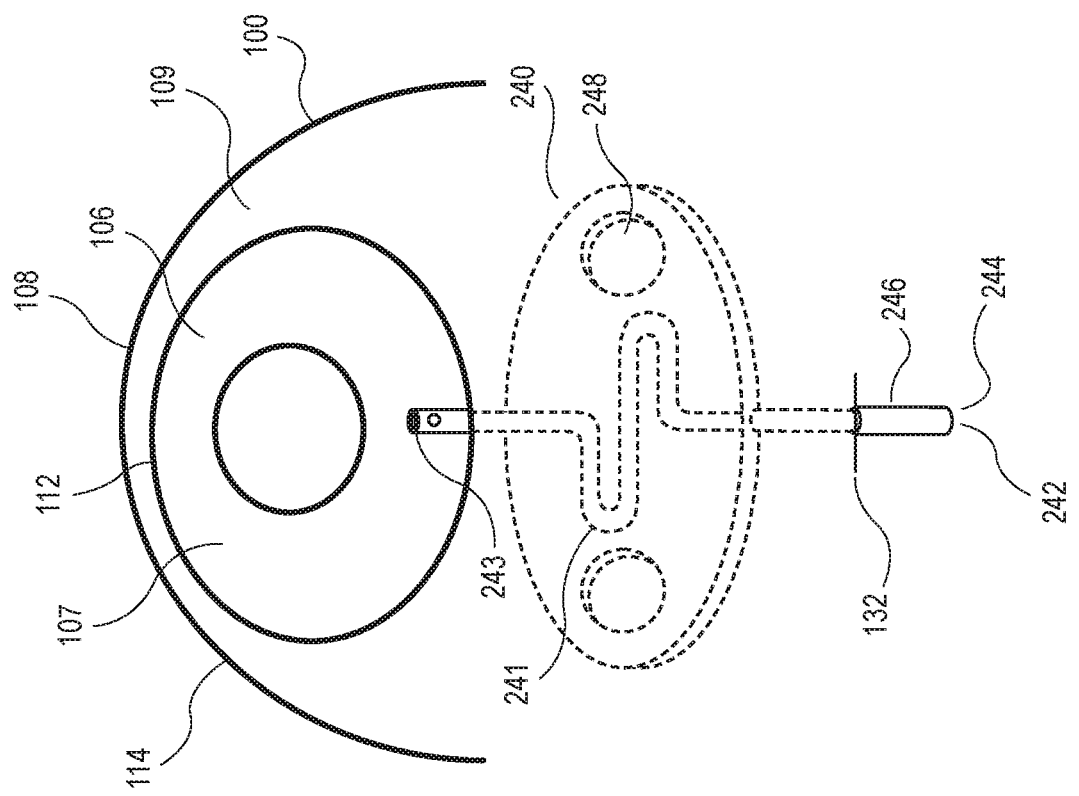
FIG. 52 is a perspective view of an eye showing the cornea, sclera, and iris with the implanted ocular device according to FIG. 51.

In one embodiment of this invention, as shown in FIG. 52, the ocular device 240 is implanted in the eye 100. The distal end 243 (shown in solid line) is seated in the anterior chamber 106 pointing away from the trabecular meshwork 112. The tortuous portion of the body 241 (shown in dotted line) is embedded in the coating or the plate 249 and then implanted in the sclera 109 of the eye 100. The proximal end 244 comprises the low-profile compliant tube 246 (shown in solid line) that is protruded out of the exterior surface of the eyeball 100 through the incision 132. The low-profile compliant tube 246 is flexible to comply with the movement of the eyelid or collapsible under pressure to minimize its profile on the surface of the eye 100 and irritation to the eyelids or eye 100. The one or more suture holes 248 are configured to receive suture, and thereby fixing the ocular device in in the eye 100 during the implantation. The tortuous fluid conduit 242 is sized to permit drainage of aqueous humor from the anterior chamber 106 to the tear film 108 of the eye 100. This increase in fluid conduit's 242 tortuosity can also increase the conduit's total length without interfering with patient's field of vision or the trabecular meshwork 112 when it is implanted in the eye 100.

In another embodiment of this invention, the ocular device 240 and the plate 249 are integrated as one part. The integrated part can be fabricated by methods such as laser machining, chemical etching, plasma etching, 3D printing, photo etching, and the like.

In some embodiments, the lumen size of the fluid conduit may be any size that allows for normal IOP in the eye without clogging or bacteria ingression into the anterior chamber. In some embodiments of this invention, the lumen size of the fluid conduit can be from about 15 μm to about 120 μm. In some embodiments, the lumen size of the fluid conduit can be from about 20 μm to about 110 μm. In some embodiments, the lumen size of the fluid conduit can be from about 30 μm to about 100 μm.

In some embodiments, the total length of the fluid conduit may be any length that allows for drainage of aqueous humor from an anterior chamber to the tear film to achieve normal IOP in the eye without clogging or bacteria ingression into the anterior chamber. In some other embodiments of this invention, the total length of the fluid conduit can be from about 0.3 cm to about 10 cm. In some embodiments, the total length of the fluid conduit can be from about 0.4 cm to about 7 cm. In some embodiments, the total length of the fluid conduit can be from about 0.5 cm to about 5 cm.

Figure 53:
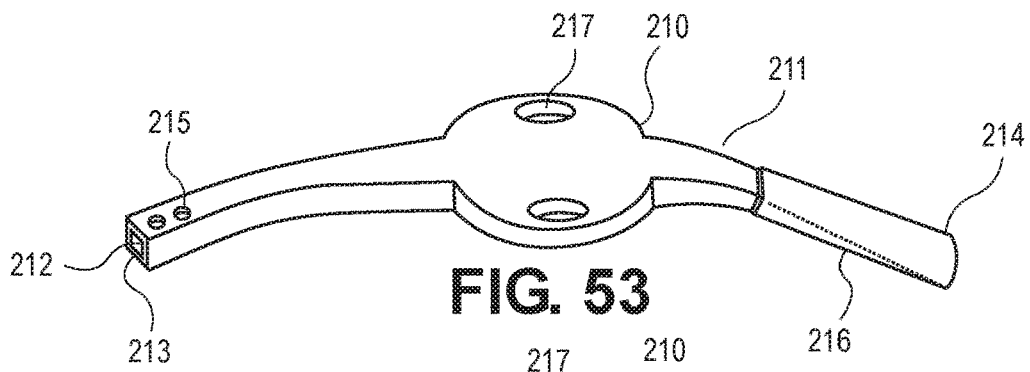
FIG. 53 is a perspective view of an ocular device described in one embodiment of this disclosure with integrated body.

In another embodiment of this invention, the ocular device and the plate are integrated as one part. This part can be fabricated by methods such as laser machining, chemical etching, plasma etching, 3D printing, photo etching, and the like. FIG. 53 shows the perspective view of an ocular device 210, it includes a body 211 defining a fluid conduit 212 with a fixed lumen size along the length of the fluid conduit 212, a distal end 213 and a proximal end 214 to allow the aqueous humor to flow from the distal end 213 to the proximal end 214 when it is implanted in the eye 100. The distal end 213 is configured to seat in the anterior chamber 106 and is directing away from the trabecular meshwork when it is implanted in the anterior chamber 106. The distal end 213 further comprises one or more openings 215 serving as part of the flow pathway to regulate the flow rate of aqueous humor. The one or more openings 215 are configured to promote fluid communication near the flow inlet and prevent clogging of the inlet. The proximal end 214 comprises a low-profile compliant tube 216 that is configured to protrude out of the exterior surface of the eyeball 100 through the incision 132. The low-profile compliant tube 216 is flexible to comply with the movement of the eyelid or collapsible under pressure to minimize its profile on the surface of the eye 100 and irritation to the eyelids or eye 100. The lumen of the fluid conduit 212 comprises a generally rectangular cross-sectional shape. However, it is understood that other cross-sectional shapes may be suitable as well. For example, the cross-sectional shapes of the fluid conduit 212 lumen may be round, oval, rectangular, square, multiple lumens, half-round, half-oval or irregular, etc. The one or more suture holes 217 are configured to receive suture during the implantation. The fluid conduit 212 is sized to permit drainage of aqueous humor from the anterior chamber 106 to the tear film 108 of the eye 100 when the ocular device 1001 is implanted in the cornea 107, limbus 110, sclera 109 or conjunctiva 114. Alternatively, the tortuous fluid conduit 212 comprises an enlarged lumen size along the length of the fluid conduit 212. The lumen size increases from the distal end 213 to the proximal end 214 to reduce the chance for clogging in the fluid conduit 212 because the enlarged lumen allows the aqueous humor outflow to remove any debris deposition in the fluid conduit 212.

Figure 54:
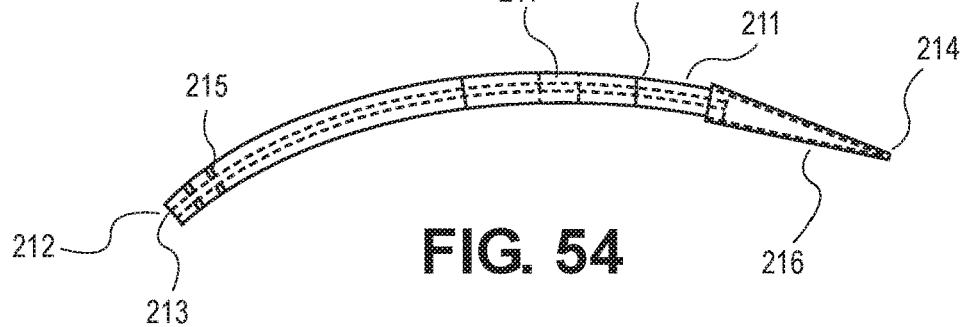
FIG. 54 is a side view of the ocular device according to FIG. 53 with integrated body.
Figure 55:
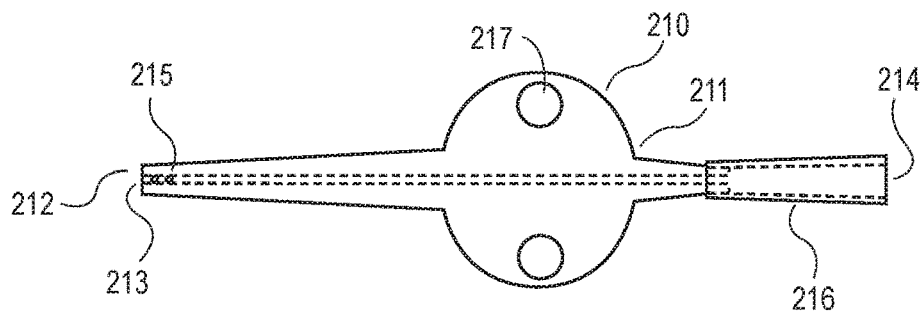
FIG. 55 is a top view of the ocular device according to FIG. 53 with integrated body.
Figure 56:
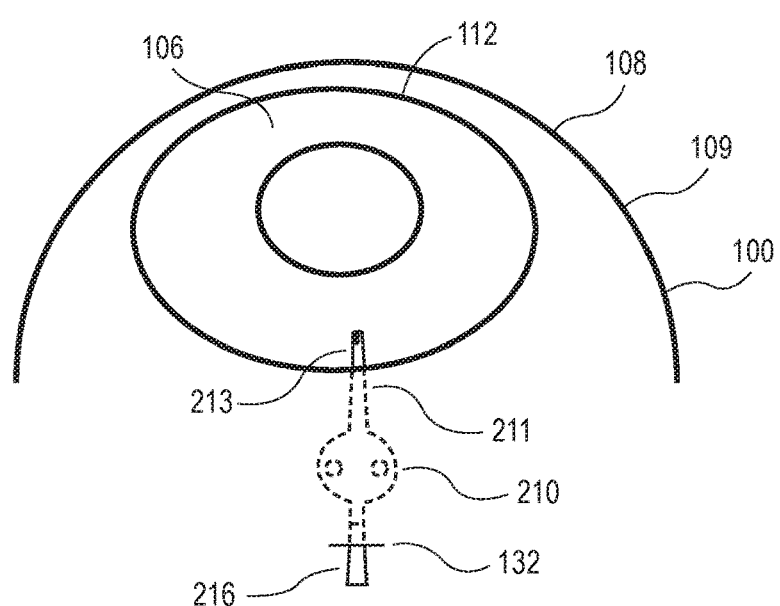
FIG. 56 is a perspective view of an eye showing the cornea, sclera, and iris with the implanted ocular device according to FIG. 53.

FIG. 54 shows the side view of the ocular device 210, it includes the body 211 defining the fluid conduit 212 (shown in dotted line) with the distal end 213 and the proximal end 214 to allow the aqueous humor to flow from the distal end 213 to the proximal end 214 when it is implanted in the eye 100. There is no valve, narrowing or filter in the fluid conduit 212. The ocular device 210 also comprises a curved body 211 that is configured to follow the curvature of the eye 100 when the device 210 is implanted in the eye 100. FIG. 55 shows the top view of the ocular device 210. The fluid conduit 212 (shown in dotted line) comprises a distal end 213 and a proximal end 214. As shown in FIG. 56, the ocular device 210 is implanted in the eye 100. The distal end 213 is seated in the anterior chamber 106 pointing away from the trabecular meshwork 112. Portion of the body 211 (shown in dotted line) is embedded in the sclera 109 of the eye 100. The compliant tube 216 is protruded out of the exterior surface of the eyeball 100 through the incision 132.

Figure 57:
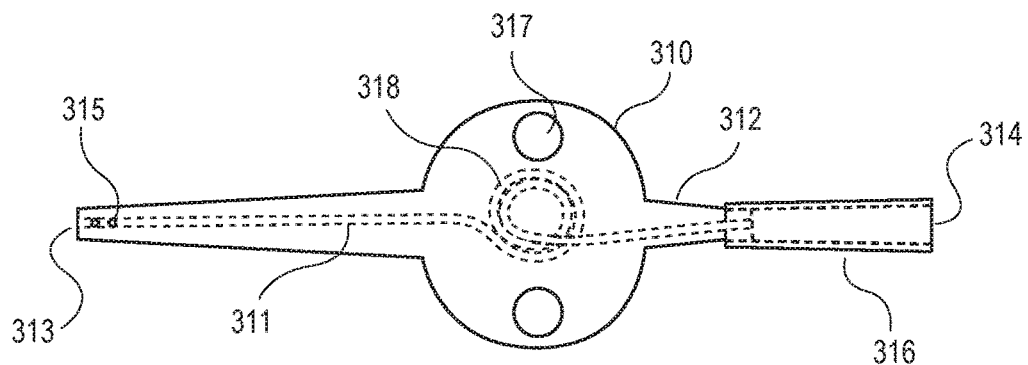
FIG. 57 is a top view of an integrated ocular device with tortuous fluid conduit described in one embodiment of this disclosure.

In yet another embodiment of this invention, FIG. 57 shows the top view of an integrated ocular device 310 with a tortuous fluid conduit 311. The integrated ocular device 310 has a similar perspective appearance with the other integrated ocular device 210 shown in FIGS. 53 and 54. The integrated ocular device 310 can be fabricated by methods such as laser machining, chemical etching, plasma etching, 3D printing, photo etching, and the like. As shown in FIG. 57, the integrated ocular device 310 includes a body 312 defining a tortuous fluid conduit 311 (shown in dotted line) with a fixed lumen along the length of the fluid conduit 311, a distal end 313 and a proximal end 314 to allow the aqueous humor to flow from the distal end 313 to the proximal end 314 when it is implanted in the eye 100. There is no valve, narrowing or filter in the fluid conduit 311. The distal end 313 is configured to seat in the anterior chamber 106 and is directing away from the trabecular meshwork 112 when it is implanted in the anterior chamber 106. The distal end 313 further comprises one or more openings 315 serving as part of the flow pathway to regulate the flow rate of aqueous humor. The one or more openings 315 are configured to promote fluid communication near the flow inlet and prevent clogging of the inlet. The proximal end 314 comprises a low-profile compliant tube 316 that is configured to protrude out of the exterior surface of the eyeball 100 through the incision 132. The low-profile compliant tube 316 is flexible to comply with the movement of the eyelid or collapsible under pressure to minimize its profile on the surface of the eye 100 and irritation to the eyelids or eye 100. The one or more suture holes 317 are configured to receive suture during the implantation. The tortuous fluid conduit 311 comprise one or more circles 318 with a generally rectangular lumen shape. However, it is understood that other lumen shapes may be suitable as well. The tortuous fluid conduit 311 is sized to permit drainage of aqueous humor from the anterior chamber 106 to the tear film 108 of the eye 100 when the ocular device 1010 is implanted in the cornea 107, limbus 110, sclera 109 or conjunctiva 114. The tortuous fluid conduit 311 is configured to increase the total conduit length and flow resistance of the fluid conduit 311 without increasing the linear distance between the proximal end 314 and distal end 313, and thereby reducing the risk of interfering with patient's field of vision. This tortuous fluid conduit 311 is also configured to change aqueous humor flow direction in the conduit 311, thereby increasing turbulent flow and flow resistance of the device 310. Furthermore, a longer fluid conduit's 311 length is advantageous in allowing a larger lumen size in the fluid conduit 311 to avoid clogging while maintaining the same flow resistance to reduce IOP and prevent hypotony. This increase in lumen size of the fluid conduit 311 reduces the chance for clogging caused by debris or tissue in the aqueous humor. In addition, the increase in the fluid conduit's 311 total length also increases antimicrobial surface area and fluid conduit's 311 ability to impede the transmission of microorganisms into the anterior chamber 106. Alternatively, the tortuous fluid conduit 311 comprises an enlarged lumen size along the length of the fluid conduit 311. The lumen size increases from the distal end 313 to the proximal end 314 to reduce the chance for clogging in the fluid conduit 311 because the slowly enlarged lumen allows the aqueous humor outflow to remove any debris deposition in the fluid conduit 311.

Figure 58:
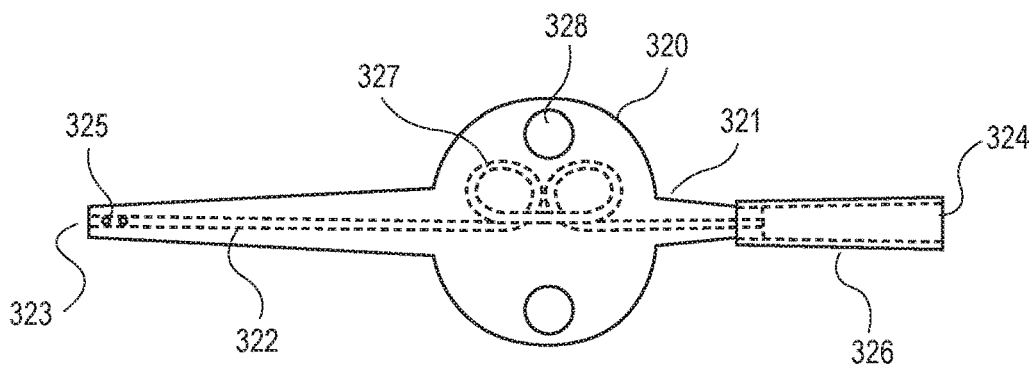
FIG. 58 is a top view of an integrated ocular device with tortuous fluid conduit described in another embodiment of this disclosure.

In one embodiment of this invention, an integrated ocular device 320 includes a body with a tortuous fluid conduit. The integrated ocular device 320 has a similar perspective appearance with the other integrated ocular device 210 shown in FIGS. 53 and 54. The integrated ocular device 320 can be fabricated by methods such as laser machining, chemical etching, plasma etching, 3D printing, photo etching, and the like. FIG. 58 shows the top view of the ocular device 320, it includes a body 321 defining a tortuous fluid conduit 322 (shown in dotted line) with a fixed lumen size along the length of the fluid conduit 322, a distal end 323 and a proximal end 324 to allow the aqueous humor to flow from the distal end 323 to the proximal end 324 when it is implanted in the eye 100. The distal end 323 is configured to seat in the anterior chamber 106 and is directing away from the trabecular meshwork 112 when it is implanted in the anterior chamber 106. The distal end 323 further comprises one or more openings 325 serving as part of the flow pathway to regulate the flow rate of aqueous humor. The one or more openings 325 are configured to promote fluid communication near the flow inlet and prevent clogging of the inlet. The proximal end 324 comprises a low-profile compliant tube 326 that is configured to protrude out of the exterior surface of the eyeball 100 through the incision 132. The low-profile compliant tube 326 is flexible to comply with the movement of the eyelid or collapsible under pressure to minimize its profile on the surface of the eye 100 and irritation to the eyelids or eye 100. The one or more suture holes 328 are configured to receive suture during the implantation. The tortuous fluid conduit 322 comprise one or more circles 327 with a generally rectangular lumen shape. However, it is understood that other lumen shapes may be suitable as well. There is no valve, narrowing or filter in the fluid conduit 322. The fluid conduit 322 is sized to permit drainage of aqueous humor from the anterior chamber 106 to the tear film 108 of the eye 100 when the ocular device 320 is implanted in the cornea 107, limbus 110, sclera 109 or conjunctiva 114. The tortuous fluid conduit 322 in the device 320 is configured to increase the total length and flow resistance of the conduit 322 without increasing the linear distance between the proximal end 324 and distal end 323. This tortuous fluid conduit 322 is also configured to change aqueous humor flow direction in the conduit 322, thereby increasing turbulent flow and flow resistance of the device 320. Alternatively, the tortuous fluid conduit 322 comprises an enlarged lumen size along the length of the fluid conduit 322. The lumen size increases from the distal end 323 to the proximal end 324 to reduce the chance for clogging in the fluid conduit 322 because the slowly enlarged lumen allows the aqueous humor outflow to remove any debris deposition in the fluid conduit 322.

Figure 59:
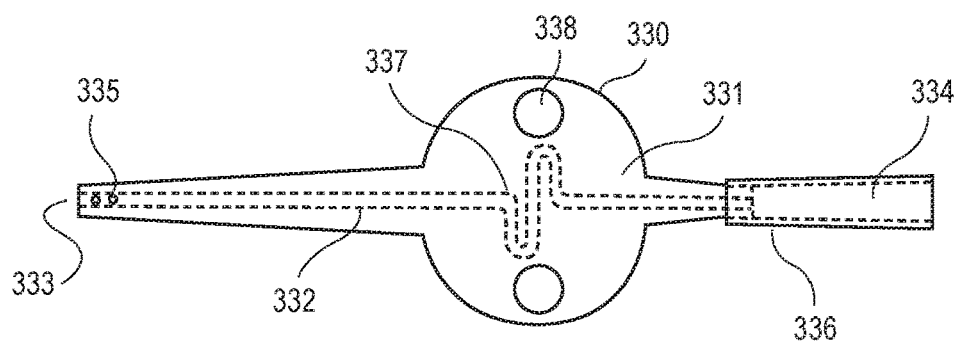
FIG. 59 is a top view of an integrated ocular device with tortuous fluid conduit described in another embodiment of this disclosure.

In one embodiment of this invention, an integrated ocular device 330 includes a body with a tortuous fluid conduit. The integrated ocular device 330 has a similar perspective appearance with the other integrated ocular device 210 shown in FIGS. 53 and 54. The integrated ocular device 330 can be fabricated by methods such as laser machining, chemical etching, plasma etching, 3D printing, photo etching, and the like. FIG. 59 shows the top view of the ocular device 330, it includes a body 331 defining a tortuous fluid conduit 332 (shown in dotted line) with a fixed lumen size along the length of the fluid conduit 332, a distal end 333 and a proximal end 334 to allow the aqueous humor to flow from the distal end 333 to the proximal end 334 when it is implanted in the eye 100. The distal end 333 is configured to seat in the anterior chamber 106 and is directing away from the trabecular meshwork 112 when it is implanted in the anterior chamber 106. The distal end 333 further comprises one or more openings 335 serving as part of the flow pathway to regulate the flow rate of aqueous humor. The one or more openings 335 are configured to promote fluid communication near the flow inlet and prevent clogging of the inlet. The proximal end 334 comprises a low-profile compliant tube 336 that is configured to protrude out of the exterior surface of the eyeball 100 through the incision 132. The low-profile compliant tube 336 is flexible to comply with the movement of the eyelid or collapsible under pressure to minimize its profile on the surface of the eye 100 and irritation to the eyelids or eye 100. The one or more suture holes 338 are configured to receive suture during the implantation. The tortuous fluid conduit 332 comprises one or more zig-zag 337 arranged side by side with a generally rectangular lumen shape. However, it is understood that other lumen shapes may be suitable as well. There is no valve, narrowing or filter in the fluid conduit 332. The fluid conduit 332 is sized to permit drainage of aqueous humor from the anterior chamber 106 to the tear film 108 of the eye 100 when the ocular device 330 is implanted in the cornea 107, limbus 110, sclera 109 or conjunctiva 114. The tortuous fluid conduit 332 in the device 330 is configured to increase the total conduit length and flow resistance of the fluid conduit 332 without increasing the linear distance between the proximal end 334 and distal end 333. This tortuous fluid conduit 332 is also configured to change aqueous humor flow direction in the fluid conduit 332, thereby increasing turbulent flow and flow resistance of the ocular device 330.

Alternatively, the tortuous fluid conduit 332 comprises an enlarged lumen size along the length of the fluid conduit 332. The lumen size increases from the distal end 333 to the proximal end 334 to reduce the chance for clogging in the fluid conduit 332 because the slowly enlarged lumen allows the aqueous humor outflow to remove any debris deposition in the fluid conduit 332.

Figure 60:
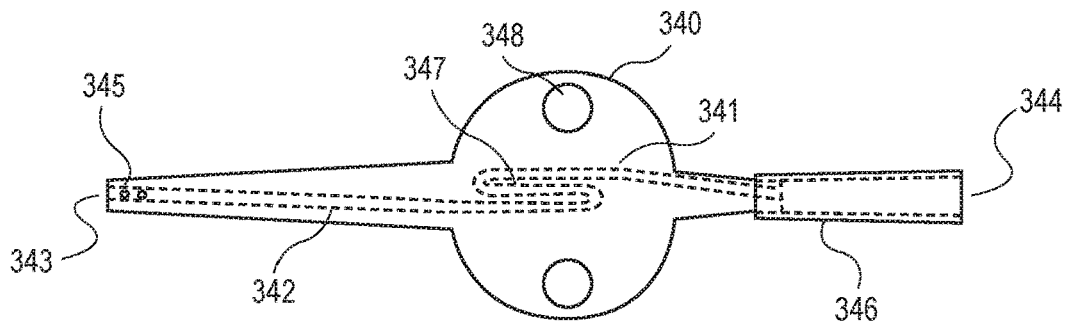
FIG. 60 is a top view of an integrated ocular device with tortuous fluid conduit described in one another embodiment of this disclosure.

In one embodiment of this invention, an integrated ocular device 340 includes a body with a tortuous fluid conduit. The integrated ocular device 340 has a similar perspective appearance with the other integrated ocular device 210 shown in FIGS. 53 and 54. The integrated ocular device 340 can be fabricated by methods such as laser machining, chemical etching, plasma etching, 3D printing, photo etching, and the like. FIG. 60 shows the top view of the ocular device 340, it includes a body 341 defining a tortuous fluid conduit 342 (shown in dotted line) with a fixed lumen size along the length of the fluid conduit 342, a distal end 343 and a proximal end 344 to allow the aqueous humor to flow from the distal end 343 to the proximal end 344 when it is implanted in the eye 100. The distal end 343 is configured to seat in the anterior chamber 106 and is directing away from the trabecular meshwork 112 when it is implanted in the anterior chamber 106. The distal end 343 further comprises one or more openings 345 serving as part of the flow pathway to regulate the flow rate of aqueous humor. The one or more openings 345 are configured to promote fluid communication near the flow inlet and prevent clogging of the inlet. The proximal end 344 comprises a low-profile compliant tube 346 that is configured to protrude out of the exterior surface of the eyeball 100 through the incision 132. The low-profile compliant tube 346 is flexible to comply with the movement of the eyelid or collapsible under pressure to minimize its profile on the surface of the eye 100 and irritation to the eyelids or eye 100. The one or more suture holes 348 are configured to receive suture during the implantation. The tortuous fluid conduit 342 comprises one or more zig-zag 347 arranged side by side with a generally rectangular lumen shape. However, it is understood that other lumen shapes may be suitable as well. There is no valve, narrowing or filter in the fluid conduit 342. The fluid conduit 342 is sized to permit drainage of aqueous humor from the anterior chamber 106 to the tear film 108 of the eye 100 when the ocular device 340 is implanted in the cornea 107, limbus 110, sclera 109 or conjunctiva 114. The tortuous fluid conduit 342 in the device 340 is configured to increase the total length and flow resistance of the conduit 342 without increasing the linear distance between the proximal end 344 and distal end 343. This tortuous fluid conduit 342 is also configured to change aqueous humor flow direction in the conduit 342, thereby increasing turbulent flow and flow resistance of the device 340. Alternatively, the tortuous fluid conduit 342 comprises an enlarged lumen size along the length of the fluid conduit 342. The lumen size increases from the distal end 343 to the proximal end 344 to reduce the chance for clogging in the fluid conduit 342 because the slowly enlarged lumen allows the aqueous humor outflow to remove any debris deposition in the fluid conduit 342.

Figure 61:
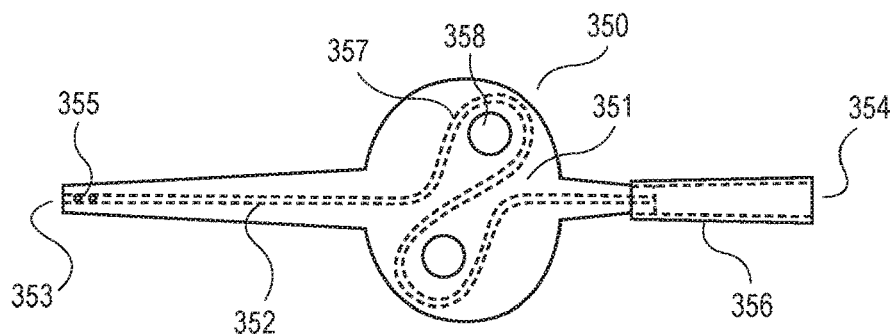
FIG. 61 is a top view of an integrated ocular device with tortuous fluid conduit described in some embodiments of this disclosure.
Figure 62:
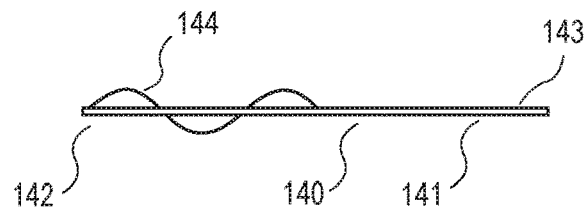
FIG. 62 is a perspective view of a cleaning tool described in one embodiment of this disclosure.
Figure 63:
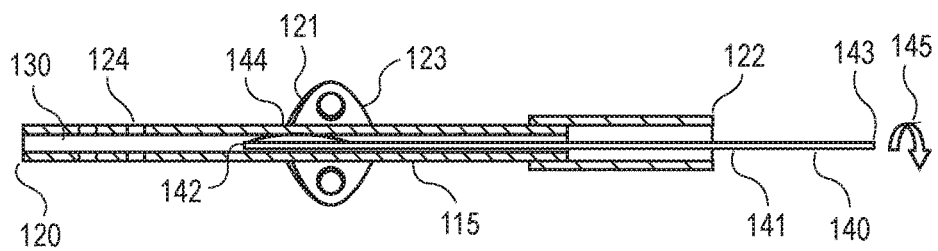
FIG. 63 is a cross-sectional view of an ocular device with the cleaning tool according to FIG. 62 in its fluid conduit.
Figure 64:
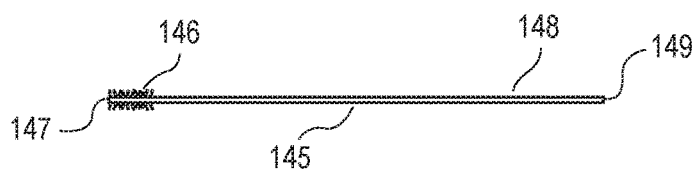
FIG. 64 is a perspective view of a cleaning tool with brush described in another embodiment of this disclosure.

In one embodiment of this invention, an integrated ocular device 350 includes a body with a tortuous fluid conduit. The integrated ocular device 350 has a similar perspective appearance with the other integrated ocular device 210 shown in FIGS. 53 and 54. The integrated ocular device 350 can be fabricated by methods such as laser machining, chemical etching, plasma etching, 3D printing, photo etching, and the like. FIG. 61 shows the top view of the ocular device 350, it includes a body 351 defining a tortuous fluid conduit 352 (shown in dotted line) with a fixed lumen size along the length of the fluid conduit 352, a distal end 353 and a proximal end 354 to allow the aqueous humor to flow from the distal end 353 to the proximal end 354 when it is implanted in the eye 100. The distal end 353 is configured to seat in the anterior chamber 106 and is directing away from the trabecular meshwork 112 when it is implanted in the anterior chamber 106. The distal end 353 further comprises one or more openings 355 serving as part of the flow pathway to regulate the flow rate of aqueous humor. The one or more openings 355 are configured to promote fluid communication near the flow inlet and prevent clogging of the inlet. The proximal end 354 comprises a low-profile compliant tube 356 that is configured to protrude out of the exterior surface of the eyeball 100 through the incision 132. The low-profile compliant tube 356 is flexible to comply with the movement of the eyelid or collapsible under pressure to minimize its profile on the surface of the eye 100 and irritation to the eyelids or eye 100. The one or more suture holes 358 are configured to receive suture during the implantation. The tortuous fluid conduit 352 comprises one or more bends 357 arranged side by side with a generally rectangular lumen shape. However, it is understood that other lumen shapes may be suitable as well. There is no valve, narrowing or filter in the fluid conduit 352. The fluid conduit 352 is sized to permit drainage of aqueous humor from the anterior chamber 106 to the tear film 108 of the eye 100 when the ocular device 350 is implanted in the cornea 107, limbus 110, sclera 109 or conjunctiva 114. The tortuous fluid conduit 352 in the device 350 is configured to increase the total length and flow resistance of the conduit 352 without increasing the linear distance between the proximal end 354 and distal end 353. This tortuous fluid conduit 352 is also configured to change aqueous humor flow direction in the conduit 352, thereby increasing turbulent flow and flow resistance of the device 350. Alternatively, the tortuous fluid conduit 352 comprises an enlarged lumen size along the length of the fluid conduit 352. The lumen size increases from the distal end 353 to the proximal end 354 to reduce the chance for clogging in the fluid conduit 352 because the slowly enlarged lumen allows the aqueous humor outflow to remove any debris deposition in the fluid conduit 352. The ocular device of this invention comprises an antimicrobial or an antifouling material in the fluid conduit to prevent migration of bacteria into the eye. However, in another embodiment of this invention, the ocular device is configured to be cleaned easily when it is needed, thereby allowing continuous drainage of aqueous humor to the tear film of the eye. In particular, the configuration of this invention allows the implanted ocular device to be cleaned non-invasively by a cleaning tool through the proximal end of the device. Because the proximal end of the fluid conduit is protruded out of the exterior surface of the eye, the proximal end can be accessed easily by the cleaning tool without invasive surgical procedure. Furthermore, because there is no valve or filter in the fluid conduit, the cleaning tool has easy access to the entire fluid conduit that needs to be cleaned. FIG. 62 shows a perspective view of a cleaning tool 140, the cleaning tool 140 comprises a bar 141 with a distal end 142 and a proximal end 143. The cleaning tool 140 also includes a wire 144 that is attached to the distal end 142 of the bar 141. An exemplary ocular device 115 is shown in FIG. 2. When cleaning is required for the ocular device 115, the distal end 142 of the cleaning tool 140 is inserted into the fluid conduit through the proximal end 122 of the ocular device 115 as shown in FIG. 63. After the distal end 142 of the cleaning tool 140 has reached the clog (not shown), the bar 141 is rotated (as shown by the arrow 145 in FIG. 63) with the coupled wire 144 by the clinician. As a consequence, the rotating wire 144 creates agitation, and thereby removing debris and tissue build-up from the surface of the fluid conduit 130. At the same time, the aqueous humor in the eye 100 is expelled from the anterior chamber 106 by the IOP and forced to flow outwardly into the tear film 108 through the fluid conduit 130. This aqueous humor flow works with the cleaning tool 140 to remove any detached debris and tissue from the fluid conduit 130. By being able to clean the debris and tissue build-up in the fluid conduit 130, the functionality of the device 115 to drain the aqueous humor and regulate the IOP in the eye 100 can be maintained. Alternatively, the cleaning tool comprises a wire. Alternatively, FIG. 64 shows a perspective view of a cleaning tool 145, the cleaning tool 145 comprises a bar 148 with a distal end 147 and a proximal end 149. The cleaning tool 145 also includes a brush 146 or a foam that is attached to the distal end 147 of the bar 148 as shown in FIG. 64. When cleaning is required, the distal end 147 of the cleaning tool 145 is inserted into the fluid conduit 130 through the proximal end 122 of the ocular device 115. The brush 146 is configured to rub against the inner surface of the fluid conduit 130 to detach any debris/tissue from the surface. Then the aqueous humor outflow in the fluid conduit 130 works with the cleaning tool 145 to remove any detached debris and tissue in the conduit 130.

One of the issues for current aqueous humor drainage devices is that the drainage rate of the aqueous humor and the resulting IOP in the eye depend on both the characteristics of the implants and the wound healing at the draining site. As a consequence, the IOP of the eye after the implantation of the current drainage devices is difficult to predict and control. A variety of mechanical mechanisms, such as valve, temporary ligature, temporary plug, temporary clamp and filter, have been used in the current drainage devices to control the aqueous humor outflow after implantation to avoid hypotony. However, fine adjustment of aqueous humor flow rate in the device is difficult and often invasive for those proposed mechanisms. Furthermore, those adjustment mechanisms can only change the aqueous humor outflow from a lower flow rate right after the implantation to a higher flow rate after the wound healing is completed. Invasive surgery used for the adjustment may also lead to uncertain IOP caused by the secondary tissue healing. As a result, effective control of aqueous humor outflow and IOP remains a problem for those types of drainage devices.

In this invention, a normal IOP in the eye can be maintained by selecting the ocular device with appropriate fluid conduit geometry (e.g. lumen size, length, tortuosity, etc.) and surface roughness for the treatment. However, if adjustment of IOP is desired after implantation, the ocular device of this invention is configured to allow easy and non-invasive adjustment of IOP to achieve the desired IOP. Furthermore, the adjustment mechanism of this invention is capable of changing the aqueous humor outflow from a lower flow rate to a higher flow rate, or vis versa.

In another embodiment of this invention, the IOP of the eye and the flow resistance of the ocular device can be regulated by an adjustable flow restrictor placed in the fluid conduit of the ocular device. The adjustable flow restrictor is configured to restrict the aqueous humor flow rate in the fluid conduit and cause turbulent flow, thereby increasing the flow resistance of the ocular device. The amount of increase in flow resistance is related to the size and the length of the adjustable flow restrictor in the fluid conduit of the ocular device. Because the proximal ends of the ocular device and the adjustable flow restrictor are protruded out of the exterior surface of the eye, and there is no valve, narrowing or filter in the fluid conduit to stop the movement of the flow restrictor, the adjustable flow restrictor in the fluid conduit can be manipulated easily by the clinicians without invasive surgery. As a result, the flow resistance of the device and the IOP in the eye can be regulated non-invasively by the adjustable flow restrictor in the fluid conduit.

Figure 65:
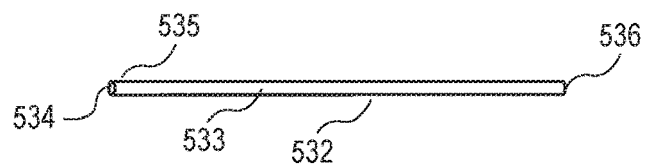
FIG. 65 is a perspective view of an adjustable flow restrictor described in one embodiment of this disclosure.
Figure 66:
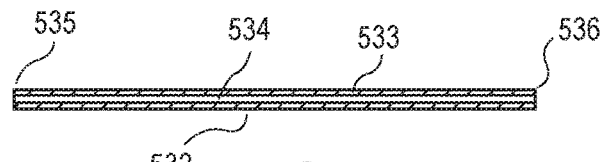
FIG. 66 is a cross-sectional view of the adjustable flow restrictor according to FIG. 65.

FIG. 65 shows the perspective view of an adjustable flow restrictor 532, it includes a body 533 defining a lumen 534 with a distal end 535 and a proximal end 536 to allow the aqueous humor to flow from the distal end 535 to the proximal end 536. FIG. 66 shows the cross-sectional view of the adjustable flow restrictor 532, the adjustable flow restrictor 532 comprises the body 533 defining the lumen 534 with the distal end 535 and the proximal end 536. The distal end 535 of the adjustable flow restrictor 532 is configured to seat in the fluid conduit of the ocular device. The proximal end 536 of the adjustable flow restrictor 532 is configured to seat in the tear film. In one embodiment of this invention, the adjustable flow restrictor 532 comprises an antimicrobial or an antifouling material to prevent bacteria attachment on the surface of the flow restrictor 532.

Figure 67A:
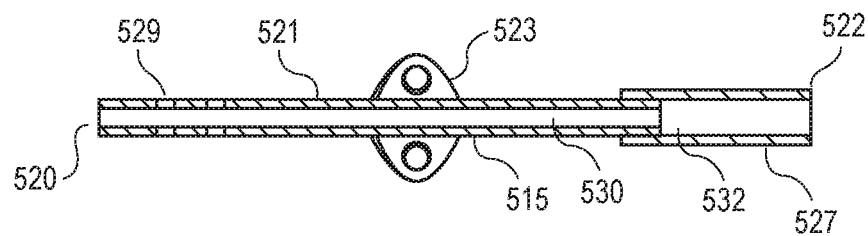
FIG. 67*a* is a cross-sectional view of an ocular device described in one embodiment of this disclosure.

FIG. 67a shows the cross-sectional view of an exemplary ocular device 515 with a fluid conduit 530. The ocular device 515 has a similar perspective appearance with the ocular device 115 shown in FIG. 2. The ocular device 515 includes a body 521 defining a fluid conduit 530 with a fixed lumen size along the length of the fluid conduit 530, a distal end 520 and a proximal end 522 to allow the aqueous humor to flow from the distal end 520 to the proximal end 522. The distal end 520 is configured to seat in the anterior chamber 106 when the ocular device 515 is implanted in the eye 100. The distal end 520 further comprises one or more openings 529 serving as part of the flow pathway to regulate the flow rate of aqueous humor. The one or more openings 529 are configured to promote fluid communication near the flow inlet and prevent clogging of the inlet. The proximal end 522 comprises a compliant tube 527 that is configured to protrude out of the exterior surface of the eyeball 100 through the incision 132 on the eye 100. The low-profile compliant tube 527 is flexible to comply with the movement of the eyelid or collapsible under pressure to minimize its profile on the surface of the eye 100 and irritation to the eyelids or eye 100. The body 521 also comprises one or more suture holes 523 on the exterior surface of the body 521. The fluid conduit 530 is sized to permit drainage of aqueous humor from the anterior chamber 106 to the tear film 108 of the eye 100 when the ocular device 515 is implanted in the cornea 107, limbus 110, sclera 109 or conjunctiva 114.

As disclosed in the previous sections, the normal IOP of the eye can be maintained by implanting the ocular device 515 with appropriate fluid conduit 530 geometry and surface roughness in the eye 100. During postoperative visits, the clinician can monitor and measure the intraocular pressure in the patients. If adjustment of IOP is desired, the ocular device 515 of this invention is configured to allow easy and non-invasive adjustment of the flow resistance in the ocular device 515 to achieve the desired IOP.

Figure 67B:
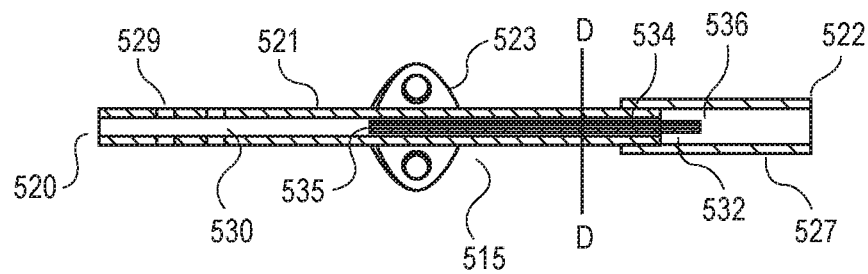
FIG. 67*b* is a cross-sectional view of the ocular device according to FIG. 67*a* with the adjustable flow restrictor in its fluid conduit.
Figure 68:
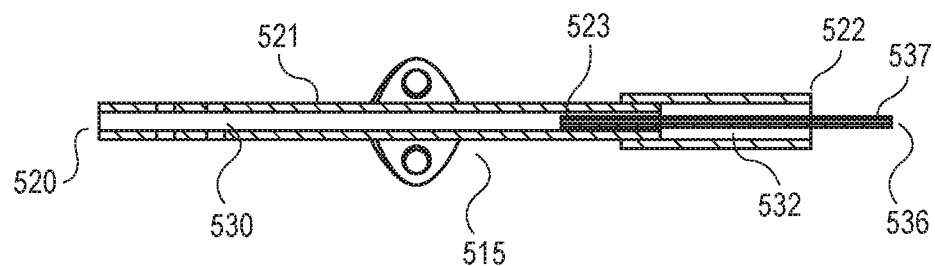
FIG. 68 is a cross-sectional view of the ocular device according to FIG. 67*a* with portion of the adjustable flow restrictor pulled out from the fluid conduit.
Figure 69:
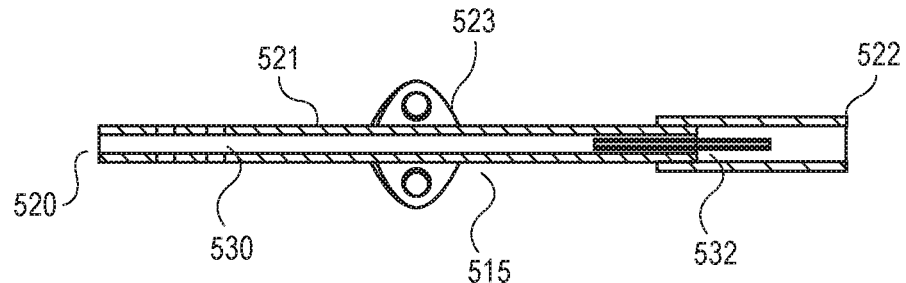
FIG. 69 is a cross-sectional view of the ocular device according to FIG. 67*a* with portion of the adjustable flow restrictor trimmed.

If a higher IOP is desired after the device 515 is implanted in the eye 100, the distal end 535 of the adjustable flow restrictor 532 can be inserted in the fluid conduit 530 non-invasively from the proximal end 522 of the ocular device 515 positioned on the exterior surface of the eye 100 as shown in FIG. 67b. The proximal end 536 of the adjustable flow restrictor 532 is also positioned at the proximal end 522 of the ocular device 515 on the exterior surface of the eye 100. Because there is no valve, narrowing or filter in the fluid conduit 530 to stop the movement, the adjustable flow restrictor 532 can have access to the entire length of the fluid conduit 530. As shown in FIG. 67b, the adjustable flow restrictor 532 in the fluid conduit 530 restricts aqueous humor flow and increases flow resistance of the ocular device 515, thereby increasing IOP of the eye 100. As shown in Equations 2 and 6, the amount of increase in IOP is related to the lumen 534 size and the length of the adjustable flow restrictor 532 placed in the fluid conduit 530 of the device 515. The smaller the lumen 534 in the flow restrictor 532, the higher the flow resistance and the IOP. The longer the flow restrictor 532 in the fluid conduit 530, the higher the flow resistance and the IOP. Because the proximal end 536 of the adjustable flow restrictor 532 is positioned at the tear film 108 of the eye 100, the fine adjustment of IOP and the flow resistance of the fluid conduit 530 can be achieved non-invasively by pushing or pulling the proximal end 536 of the flow restrictor 532 to adjust the flow restrictor's 532 length in the fluid conduit 530 with a surgical tool or a tweezer. Alternatively, the adjustable flow restrictor 532 has been placed in the fluid conduit 530 of the ocular device 515 when the ocular device 515 is implanted in the eye 100. When a lower IOP is needed after the ocular device 515 has already been implanted in the eye 100, a section 537 of the adjustable flow restrictor 532 can be pulled out from the fluid conduit 530 of the ocular device 515 from the proximal end 536 of the flow restrictor 532 with a surgical tool or a tweezer as shown in FIG. 68, thereby reducing the length of the flow restrictor 532 in the fluid conduit 530 and the flow resistance of the ocular device 515. Then the exposed section 537 of the flow restrictor 532 is removed by a scissor or a surgical blade as shown in FIG. 69. As shown in Equations 2 and 6, the amount of reduction in IOP is related to the lumen size and the length of the adjustable flow restrictor 532 in the fluid conduit 530 of the device 530. The shorter the flow restrictor 532 in the fluid conduit 530, the lower the flow resistance and the IOP in the eye 100. As a consequence, the IOP of the eye 100 can be reduced non-invasively by pulling a portion or all of the flow restrictor 532 out of the fluid conduit 530 from the proximal end 536 with a surgical tool or a tweezer. In one embodiment of this invention, the adjustable flow restrictor 532 comprises an antimicrobial or an antifouling material to prevent the bacteria from attaching to the flow restrictor 532. Alternatively, the adjustable flow restrictor 532 has been placed in the fluid conduit 530 of the ocular device 515 when the device is implanted in the eye 100.

Figure 70:
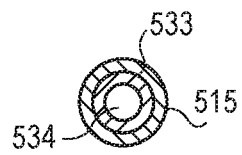
FIG. 70 is a cross-sectional view of the ocular device (along Line DD) according to FIG. 67*a* with the adjustable flow restrictor in its fluid conduit.

In another embodiment of this invention, the outer diameter of the adjustable flow restrictor 532 is slightly smaller than the inner diameter of the fluid conduit 530 so that the adjustable restrictor 532 is retained in the fluid conduit 530 by a friction force. FIG. 70 shows the cross-section view of the ocular device 515 along Line DD in FIG. 67b. Alternatively, the outer diameter of the adjustable flow restrictor 532 further comprises texture to increase the friction force and retention between the adjustable flow restrictor 532 and the fluid conduit 530. The texture may include fibers, threads, wires, brush, protrusion, nodule, foam, scaffold, mesh, bump or groove to create sufficient friction between the texture and the fluid conduit 530. The texture comprises material selected from the group consisting of polymer, metal, glass, ceramic materials.

Figure 71:
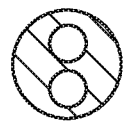
FIG. 71 is a cross-sectional view of an adjustable flow restrictor described in one embodiment of this disclosure with multiple lumens.
Figure 72:
FIG. 72 is a cross-sectional view of an adjustable flow restrictor described in another embodiment of this disclosure with a half-moon shape.

While the cross-sectional shapes of the adjustable flow restrictor 532 and its lumen 534 illustrated in the FIGS. 65 and 70 are shown as round shapes, it is understood that other cross-sectional shapes to restrict fluid conduit 530 and increase flow resistance may be suitable as well. For example, the cross-sectional shapes of the adjustable flow restrictor 532 and its lumen 534 may be round, oval, rectangular, square, multiple lumens (as shown in FIG. 71), half-moon (as shown in FIG. 72), or irregular, etc.

Figure 73:
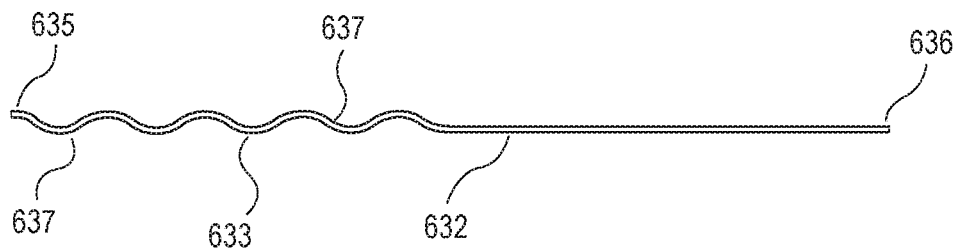
FIG. 73 is a perspective view of an adjustable flow restrictor described in another embodiment of this disclosure.

In another embodiment of this invention, an adjustable flow restrictor comprises a wire. FIG. 73 is the perspective view of the adjustable flow restrictor 632, it includes a body 633 defining a distal end 635 and a proximal end 636. The distal end 635 further comprises one or more bends 637. The distal end 635 of the adjustable flow restrictor 632 is configured to seat in the fluid conduit of the ocular device when the ocular device is implanted in the eye 100. The proximal end 636 of the adjustable flow restrictor 632 is configured to seat in the tear film 108 when the ocular device is implanted in the eye 100.

Figure 74:
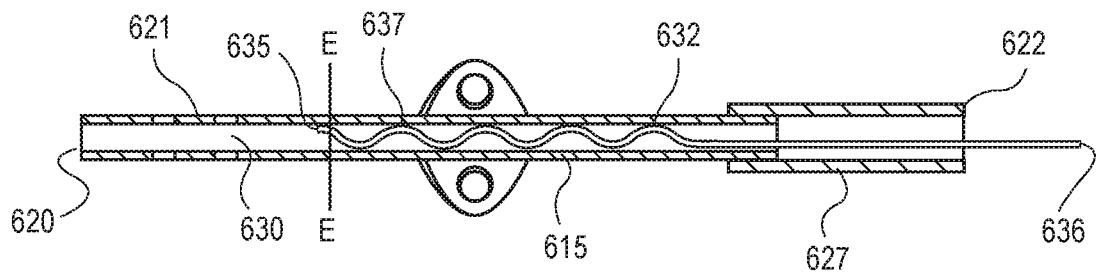
FIG. 74 is a cross-sectional view of an ocular device with the adjustable flow restrictor according to FIG. 73 in its fluid conduit.

FIG. 74 shows the cross-sectional view of an exemplary ocular device 615 with a fluid conduit 630. The ocular device 615 has a similar perspective appearance with the ocular device 115 shown in FIG. 2. As shown in FIG. 74, the ocular device 615 includes a body 621 defining a fluid conduit 630 with a fixed lumen size along the length of the fluid conduit 630, a distal end 620 and a proximal end 622 to allow the aqueous humor to flow from the distal end 620 to the proximal end 622. The distal end 620 is configured to seat in the anterior chamber 106 when the ocular device 615 is implanted in the eye 100. The proximal end 622 comprises a compliant tube 627 that is configured to protrude out of the exterior surface of the eyeball 100 through the incision on the eye 100.

Figure 75:
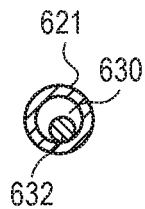
FIG. 75 is a cross-sectional view of the ocular device (along Line EE) according to FIG. 74 with the adjustable flow restrictor in its fluid conduit.

When a higher IOP is desired after the device 615 has been implanted in the eye 100, the distal end 635 of the adjustable flow restrictor 632 can be inserted in the fluid conduit 630 non-invasively from the proximal end 622 of the ocular device 615 on the exterior surface of the eye 100 as shown in FIG. 74. The one or more bends 637 of the adjustable flow restrictor 632 flexed against the inner surface of the fluid conduit 630, so that the adjustable restrictor 632 is retained in the fluid conduit 630 with a friction force. The proximal end 636 of the adjustable flow restrictor 632 is positioned at the proximal end 622 of the ocular device 615 on the exterior surface of the eye 100. Because there is no valve, narrowing or filter in the fluid conduit 630 to stop the movement, the adjustable flow restrictor 632 can have access to the entire length of the fluid conduit 630. FIG. 75 shows the cross-sectional view of the ocular device 615 along Line EE at the distal end 635 of the adjustable flow restrictor 632. As shown in Equations 2 and 6, the amount of increase in IOP is related to the size and the length of the adjustable flow restrictor 632 in the fluid conduit 630 of the device 615. The larger the size in the flow restrictor 632, the higher the flow resistance in the device 615 and the IOP in the eye 100. The longer the flow restrictor 632 in the fluid conduit 630, the higher the flow resistance in the device 615 and the IOP in the eye 100. Because the proximal end 636 of the adjustable flow restrictor 632 is positioned at the tear film 108 of the eye 100, fine adjustment of the IOP and the flow resistance can be achieved non-invasively by pushing or pulling the proximal end 636 of the flow restrictor 632 to adjust its length in the fluid conduit 630 with a surgical tool or a tweezer. As a result, the IOP in the eye 100 can be regulated by adjusting the length and size of the flow restrictor 632 in the fluid conduit 630. Alternatively, the adjustable flow restrictor 632 has been placed in the fluid conduit 630 of the ocular device 615 when the device is implanted in the eye 100.

While the cross-sectional shapes of the adjustable flow restrictor 632 illustrated in the FIG. 75 is shown as a round shape, it is understood that other cross-sectional shapes to restrict aqueous humor flow in the fluid conduit 630 and increase flow resistance may be suitable as well. For example, the cross-sectional shape of the adjustable flow restrictor 632 may be round, oval, rectangular, square, or irregular, etc. In one embodiment of this invention, the adjustable flow restrictor 632 comprises an antimicrobial or an antifouling material to prevent bacteria attachment to the flow restrictor 632.

When a lower IOP is needed after the ocular device 615 has already been implanted in the eye 100, a section of the adjustable flow restrictor 632 can be pulled out from the proximal end 622 of the ocular device 615 with a surgical tool or a tweezer as shown in FIG. 76, thereby reducing the length of the flow restrictor 632 in the fluid conduit 630 and the flow resistance of the ocular device 615. Then the exposed section 638 of the flow restrictor 632 is removed by a scissor or a surgical blade as shown in FIG. 77. As shown in Equations 2 and 6, the amount of reduction in IOP is related to the size and the length of the adjustable flow restrictor 632 in the fluid conduit 630 of the device 615. The shorter the flow restrictor 632 in the fluid conduit 630, the lower the flow resistance and the IOP in the eye 100. As a consequence, the IOP of the eye 100 can be reduced non-invasively by pulling some of the flow restrictor 632 out of the fluid conduit 630 from the proximal end 622 of the fluid conduit 630 with a surgical tool or a tweezer. In one embodiment of this invention, the adjustable flow restrictor 632 comprises an antimicrobial or an antifouling material to prevent the bacteria from attaching to the flow restrictor 632. Alternatively, the adjustable flow restrictor 632 has been placed in the fluid conduit 630 of the ocular device 615 when the device 615 is implanted in the eye 100.

In another embodiment of this invention, an adjustable flow restrictor comprises a tapered wire. FIG. 78 is the perspective view of the tapered adjustable flow restrictor 640, it includes a body 641 defining a distal end 642 and a proximal end 643. Due to the tapering, the cross-section of the flow restrictor 640 decreases gradually from the proximal end 643 to the distal end 642 643. The distal end 642 further comprises one or more bends 644. The distal end 642 of the adjustable flow restrictor 640 is configured to seat in the fluid conduit of the ocular device when the ocular device is implanted in the eye 100. The proximal end 643 of the adjustable flow restrictor 640 is configured to seat in the tear film 108 when the ocular device is implanted in the eye 100.

FIG. 79 shows the cross-sectional view of an exemplary ocular device 650 with a fluid conduit 651. The ocular device 650 has a similar perspective appearance with the ocular device 115 shown in FIG. 2. As shown in FIG. 79, the ocular device 650 includes a body 652 defining a fluid conduit 651 with a fixed lumen size along the length of the fluid conduit 651, a distal end 653 and a proximal end 654 to allow the aqueous humor to flow from the distal end 653 to the proximal end 654. The distal end 653 is configured to seat in the anterior chamber 106 when the ocular device 650 is implanted in the eye 100. The proximal end 654 comprises a compliant tube 655 that is configured to protrude out of the exterior surface of the eyeball 100 through the incision on the eye 100.

As disclosed in the previous sections, the normal IOP of the eye can be maintained by implanting the ocular device 650 with appropriate fluid conduit geometry and surface roughness. However, if a higher IOP is desired after the device 650 has been implanted in the eye 100, the distal end 642 of the adjustable flow restrictor 640 can be inserted in the fluid conduit 651 non-invasively from the proximal end 654 of the ocular device 650 on the exterior surface of the eye 100. FIG. 79 shows the cross-sectional view of the ocular device 650 with the inserted adjustable flow restrictor 640 in its fluid conduit 651. The one or more bends 644 of the adjustable flow restrictor 640 are flexed against the inner surface of the fluid conduit 651 so that the adjustable restrictor 640 is retained in the fluid conduit 651 with a friction force. FIG. 80 shows the cross-sectional view of the ocular device 650 along Line FF. The adjustable flow restrictor 640 restricts fluid conduit's 651 aqueous humor flow area and increases flow resistance of the ocular device 650, thereby increasing IOP of the eye 100.

As shown in Equations 2 and 6, the amount of increase in IOP is related to the size and the length of the adjustable flow restrictor 640 in the fluid conduit 651 of the ocular device 650. The smaller the flow restrictor 640 in the fluid conduit 651, the lower the flow resistance and the IOP in the eye 100. The longer the flow restrictor 640 in the fluid conduit 651, the higher the flow resistance and the IOP in the eye 100. Because the proximal end 643 of the adjustable flow restrictor 640 is positioned at the tear film 108 of the eye 100, the fine adjustment of the IOP of the eye 100 and the flow resistance of the ocular device 650 can be achieved non-invasively by pushing or pulling the proximal end 643 of the flow restrictor 640 to adjust the flow restrictor's 640 length in the fluid conduit 651 with a surgical tool or a tweezer. As a result, the IOP in the eye 100 can be regulated by adjusting the length and size of the flow restrictor 640 in the fluid conduit 651. Alternatively, the adjustable flow restrictor 640 has been placed in the fluid conduit 651 of the ocular device 650 when the device 650 is implanted in the eye 100.

When a lower IOP is needed after the ocular device 650 has been already implanted in the eye 100, a section of the adjustable flow restrictor 640 can be pulled out of the fluid conduit 651 from the proximal end 654 of the ocular device 650 with a surgical tool or a tweezer as shown in FIG. 81. Because the length of the restrictor 640 in the fluid conduit 651 is reduced, the flow resistance of the ocular device 650 and the IOP in the eye 100 are also reduced. FIG. 82 shows the cross-sectional view of the ocular device 650 along Line GG (at the same location of the fluid conduit with Line FF in FIG. 79). Because the flow restrictor 640 is tapered, the aqueous humor flow area at the same location of the fluid conduit 651 is also increased (compared with FIG. 80) after the adjustment, and thereby allowing an even higher flow resistance reduction in the ocular device 650. Compared with the flow restrictor 632 with the fixed cross section along the length according to FIG. 73, the tapered flow restrictor 632 allows a higher rate of flow resistance reduction and is more effective in adjusting the flow resistance of the ocular device 650 and the IOP in the eye 100. As a result, the reduced flow resistance in the ocular device 650 leads to a lower IOP in the eye 100 after the adjustment. Then the exposed section 645 of the flow restrictor 640 outside the ocular device 650 is removed by a scissor or a surgical blade. In one embodiment of this invention, the adjustable flow restrictor 640 comprises an antimicrobial or an antifouling material to prevent bacteria attachment to the flow restrictor 640. Alternatively, the adjustable flow restrictor 640 has been placed in the fluid conduit 651 of the ocular device 650 when the ocular device 650 is implanted in the eye 100.

In yet another embodiment of this invention, an adjustable flow restrictor comprises a plurality of wires with various lengths. Those wires are bundle together to form an adjustable flow restrictor with stepwise tapering. FIG. 83 is the perspective view of the adjustable flow restrictor 660, it includes a body 661 defining a distal end 662 and a proximal end 663. The distal end 662 further comprises one or more bends 664. The distal end 662 of the adjustable flow restrictor 660 is configured to seat in the fluid conduit of the ocular device when the ocular device is implanted in the eye 100. The proximal end 663 of the adjustable flow restrictor 660 is configured to seat in the tear film 108 when the ocular device is implanted in the eye 100. Due to the tapering, the cross-section of the flow restrictor 660 decreases step-wisely from the proximal end 663 to the distal end 662. As discussed previously, the tapered flow restrictor 660 is more effective in adjusting the flow resistance of the ocular device and the IOP in the eye 100.

In one embodiment of this invention, an ocular device comprises an enlarged fluid conduit. The ocular device 670 has a similar perspective appearance with the ocular device 115 shown in FIG. 2. FIG. 84 shows the cross-sectional view of the ocular device 670, it includes a body 671 defining a fluid conduit 672 with a distal end 673 and a proximal end 674 to allow the aqueous humor to flow from the distal end 673 to the proximal end 674. The lumen size of the fluid conduit 672 increases gradually from the distal end 673 to the proximal end 674. The distal end 673 is configured to seat in the anterior chamber 106 when the ocular device 670 is implanted in the eye 100. The distal end 673 further comprises one or more openings 677 serving as part of the flow pathway to regulate the flow rate of aqueous humor. The one or more openings 677 are configured to promote fluid communication near the flow inlet and prevent clogging of the inlet. The proximal end 674 comprises a low-profile compliant tube 675 that is configured to protrude out of the exterior surface of the eyeball 100 through the incision on the eye 100. The low-profile compliant tube 675 is flexible to comply with the movement of the eyelid or collapsible under pressure to minimize its profile on the surface of the eye 100 and irritation to the eyelids or eye 100. FIG. 85 shows a cross-sectional view of the ocular device 670 along Line HH at the distal end 673. FIG. 86 shows a cross-sectional view of the ocular device 670 along Line JJ closes to the proximal end 674. Due to the gradual enlargement in the fluid conduit 672, the lumen size of the fluid conduit 672 increases from the distal end 673 to the proximal end 674.

As disclosed in the previous sections, the normal IOP of the eye 100 can be maintained by implanting the ocular device 670 with appropriate fluid conduit geometry and surface roughness. However, when a higher IOP is desired after the ocular device 670 has been implanted in the eye 100, the adjustable flow restrictor 632 according to FIG. 73 can be utilized in this invention. The distal end 635 of the adjustable flow restrictor 632 can be inserted in the fluid conduit 672 non-invasively from the proximal end 674 of the ocular device 670 on the tear film 108 as shown in FIG. 87. The one or more bends 637 of the adjustable flow restrictor 632 are flexed against the inner surface of the fluid conduit 672, so that the adjustable restrictor 632 is retained in the fluid conduit 672 with a friction force. The proximal end 636 of the adjustable flow restrictor 632 is positioned at the proximal end 674 of the ocular device 670 on the tear film 108. Because there is no valve, narrowing or filter in the fluid conduit 672 to stop the movement, the adjustable flow restrictor 632 has access to the entire length of the fluid conduit 672. FIG. 88 shows the cross-sectional view of the ocular device 670 along Line KK at the distal end 635 of the flow restrictor 632. As shown in Equations 2 and 6, the amount of increase in IOP of the eye 100 is related to the size and the length of the adjustable flow restrictor 632 in the fluid conduit 672 of the device 670. The larger the size of the flow restrictor 632, the higher the flow resistance and the IOP. The longer the flow restrictor 632 in the fluid conduit 672, the higher the flow resistance and the IOP. Because the proximal end 636 of the adjustable flow restrictor 632 is positioned at the tear film 108 of the eye 100, the fine adjustment of IOP and the flow resistance can be achieved non-invasively by pushing or pulling the proximal end 636 of the flow restrictor 632 to adjust its length in the fluid conduit 672 with a surgical tool or a tweezer. As a result, the IOP in the eye 100 can be regulated by adjusting the length and size of the flow restrictor 632 in the fluid conduit 672. Alternatively, the adjustable flow restrictor 632 has been placed in the fluid conduit 672 of the ocular device 670 when the ocular device 670 is implanted in the eye 100. Alternatively, the adjustable flow restrictor of different geometries can also be placed in the fluid conduit 672 of the ocular device 670 when the ocular device 670 has been implanted in the eye 100. Alternatively, the adjustable flow restrictor of different geometries has already been placed in the fluid conduit 672 of the ocular device 670 when the ocular device 670 is implanted in the eye 100.

When a lower IOP is needed after the ocular device 670 has already been implanted in the eye 100, a section 638 of the adjustable flow restrictor 632 can be pulled out of the ocular device 670 from the proximal end 674 of the ocular device 670 with a surgical tool or a tweezer as shown in FIG. 89. FIG. 90 shows the cross-sectional view of the ocular device 670 along Line LL at the distal end 635 of the flow restrictor 632. As shown in FIG. 89, the length of the restrictor 632 in the fluid conduit 672 is reduced, and thereby reducing the flow resistance of the ocular device 670 and the IOP in the eye 100. In addition, the lumen size of the fluid conduit 672 at the distal end 635 of the flow restrictor 632 increases as the restrictor 632 is removed from the fluid conduit 672 because the fluid conduit 672 is enlarged from the distal end 673 to the proximal end 674. As shown in FIG. 90, the lumen size of the fluid conduit 672 at the distal end 635 of the flow restrictor 632 is increased (compared with FIG. 88), and thereby allowing a higher flow resistance reduction in the ocular device 670 when the same length of the restrictor 632 is removed from the fluid conduit 672. Compared with the ocular device 515 with a fixed fluid conduit 530 (as shown in FIG. 67a), the ocular device 670 with an enlarged fluid conduit 672 is more effective in adjusting the flow resistance of the ocular device 670 and IOP in the eye 100. As a result, the reduced flow resistance after removing a portion of the flow restrictor 632 in the ocular device 670 allows a lower IOP in the eye 100. After the adjustment, the exposed section 638 of the flow restrictor 632 outside the eye 100 can be removed by a scissor or a surgical blade. In one embodiment of this invention, the adjustable flow restrictor 632 comprises an antimicrobial or an antifouling material to prevent bacteria attachment to the flow restrictor 632. Alternatively, the adjustable flow restrictor 632 has already been placed in the fluid conduit 672 of the ocular device 670 when the device 670 is implanted in the eye 100.

While the cross-sectional shapes of the enlarged fluid conduit 672 illustrated in the FIGS. 85, 86, 88 and 90 are shown as a round shape, it is understood that other cross-sectional shapes may be suitable as well. For example, the cross-sectional shape of the fluid conduit 672 may be round, oval, rectangular, square, or irregular, etc.

In yet another embodiment of this invention, the adjustable flow restrictors can be provided in combination with any of the embodiments disclosed in this invention. For example, the adjustable flow restrictors illustrated in FIGS. 65, 73, 79, and 83 can operates as adjustable flow restrictors in the ocular devices according to FIGS. 2, 10, 13, 16, 19, 22, 24, 25, 26, 28, 30, 32, 34, 36, 38, 40, 42, 45, 47, 53, and 57. Thus, some embodiments of this invention provide flow restrictors that also operates in the ocular devices according to FIGS. 2, 10, 13, 16, 19, 22, 24, 25, 26, 28, 30, 32, 34, 36, 38, 40, 42, 45, 47, 53, and 57.

While the ocular devices illustrated in the FIGS. 67a, 74, 76, 77, 79 and 83 are shown as a generally straight tubular structure, it is understood that other shapes of tubular structure may be suitable as well. For example, the ocular device may comprise a curve shape, a quarter-circle shape, a half-circle shape, a three-quarters circle shape, a full-circle, a five-quarters circle shape, a two-full-circles shape, a zig-zag shape, a spiral shape, a helix shape, or a tortuous shape, etc.

In some embodiments, the diameter of the adjustable flow restrictor may be any size that allows the flow restrictor to be inserted in the fluid conduit to regular IOP in the eye. In some embodiments of this invention, the diameter of the adjustable flow restrictor can be from about 1 μm to about 150 μm. In some embodiments, the diameter of the adjustable flow restrictor can be from about 2 μm to about 130 μm.

In some embodiments, the diameter of the adjustable flow restrictor can be from about 3 μm to about 120 μm.

In some embodiments, the total length of the adjustable flow restrictor may be any length that allows the adjustable flow restrictor to regulate IOP in the eye. In some other embodiments of this invention, the total length of the adjustable flow restrictor can be from about 0.3 cm to about 10 cm. In some embodiments, the total length of the adjustable flow restrictor can be from about 0.5 cm to about 7 cm. In some embodiments, the total length of the adjustable flow restrictor can be from about 0.5 cm to about 5 cm.

In yet another embodiment of this invention, the flow restrictor can comprise a drug or a drug-eluting part to deliver drug into the eye 100. The drug or the drug-eluting part can be provided in combination with any of the embodiments disclosed in this invention. For example, the flow restrictors illustrated in FIGS. 65, 73, 79, and 83 can comprise a drug-eluting part. Thus, some embodiments of this invention provide a flow restrictor that also operates as a drug delivery device inside the eye 100.

In one embodiment of this invention, various kinds of drugs to treat different diseases can be used. The drugs may include glaucoma drugs, steroids drugs, anti-inflammatory drugs, antibiotics drugs, anti-allergy drugs, anti-conjunctivitis drugs, etc. The drugs can be carried by the flow restrictor to be delivered in the eye 100. The entire flow restrictor itself can carry a drug or a drug-eluting part that can be partially or completely dissolved in the aqueous humor, and thereby releasing the drug in the eye 100. Alternatively, a portion of the flow restrictor can carry a drug or a drug-eluting part that can be partially or completely dissolved in the aqueous humor, and thereby releasing the drug in the eye 100. The drug-eluting part can extend along the entire length or only a portion of the length of the flow restrictor. Alternatively, the surface of the flow restrictor can be coated with a drug-eluting coating that can be partially or completely dissolved in the aqueous humor, and thereby releasing the drug in the eye 100. The drug-eluting coating can extend along the entire length or only a portion of the length of the flow restrictor. Alternatively, the drug-eluting part is an individual component, and the flow restrictor or other device can be used to insert the drug-eluting part into the eye 100 through the fluid conduit of the device.

In some embodiments, the flow restrictor comprises a drug with one or more drug carriers, and thereby including multiple drug-eluting profiles, which can be used to optimize the drug efficacy. The one or more drug carriers may be positioned in different segments of the flow restrictor. Alternatively, the one or more drug carriers may be positioned in the coating on different locations of the flow restrictor.

In some embodiments, the flow restrictor can comprise multiple drugs or multiple drug-eluting profiles, which can be used to optimize the drug efficacy. The one or more drugs may have different solubility in the aqueous humor, and thereby having different eluting profiles in the eye. Alternatively, one or more drugs may have the similar solubility in the aqueous humor, and thereby having similar eluting profile in the eye 100. The one or more drug and their carriers may be positioned in different segments of the flow restrictor. Alternatively, the one or more drug and their carriers may be positioned in the coating on different locations of the flow restrictor.

Because there is no valve, narrowing or filter in the fluid conduit, the adjustable flow restrictor can be inserted in the interior chamber 106 from the exterior of the eye 100. This embodiment of this invention allows non-invasive access to the interior chamber 106 of the eye 100 from the exterior of the eye 100. The drug or a drug-eluting part of the flow restrictor can be positioned partially or completely outside the fluid conduit and exposed in the interior chamber 106 of the eye 100 to deliver drug in the eye 100. Alternatively, if the drug-eluting part is an individual component, the drug-eluting part can be pushed out of the fluid conduit and into the interior chamber 106 of the eye 100 through the fluid conduit by the flow restrictor or other device. Alternatively, multiple drug-eluting parts (with the same or different drugs and with the same or different drug releasing profiles) can be pushed out of the fluid conduit and into the interior chamber 106 by the flow restrictor or other device.

Figure 93:
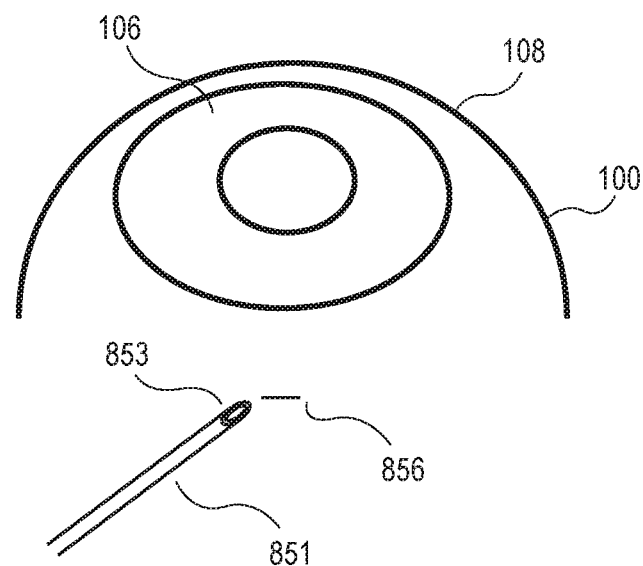
FIG. 93 is a perspective view of an eye showing the incision on the sclera and the ocular device delivery system according to FIG. 91.
Figure 94:
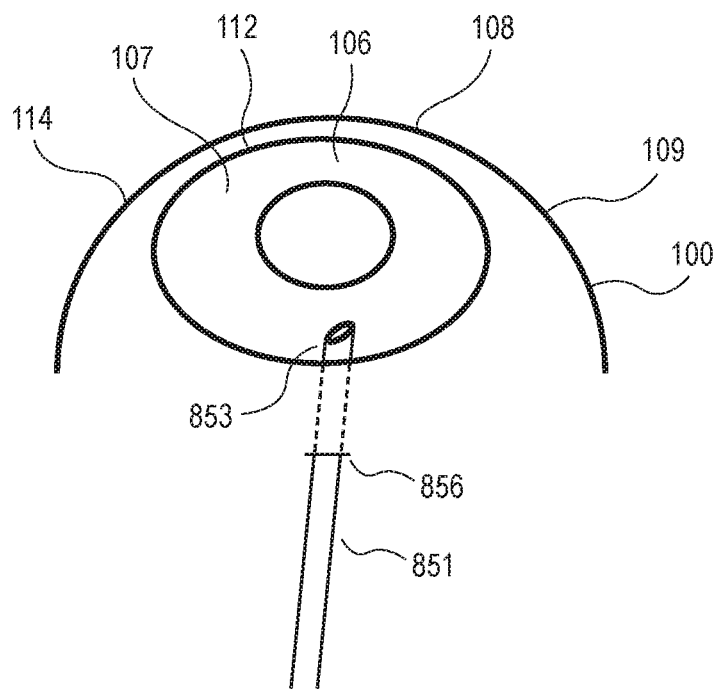
FIG. 94 is a perspective view of an eye showing the hypotube of the ocular device delivery system has been inserted in the anterior chamber according to one embodiment of this disclosure.
Figure 95:
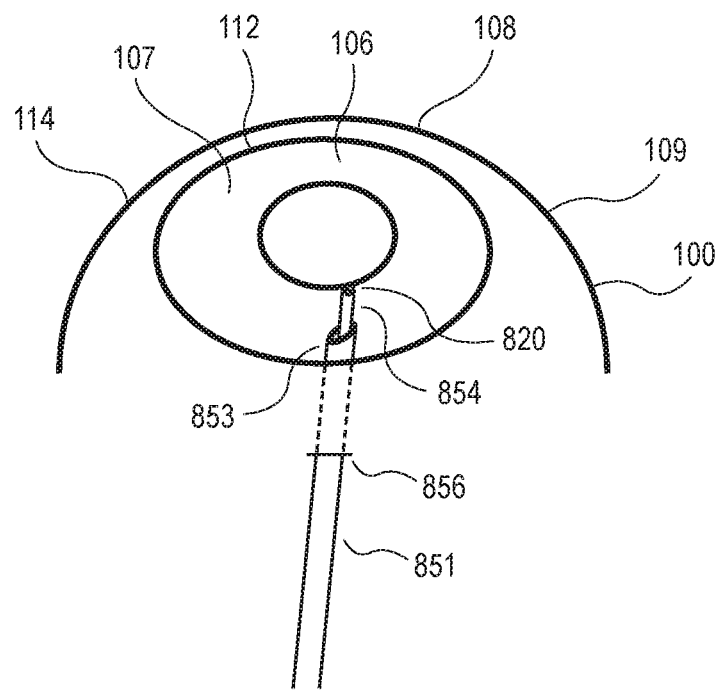
FIG. 95 is a perspective view of an eye showing the hypotube of the device delivery system and portion of the ocular device according to FIG. 2 has been pushed out from the delivery system.
Figure 96:
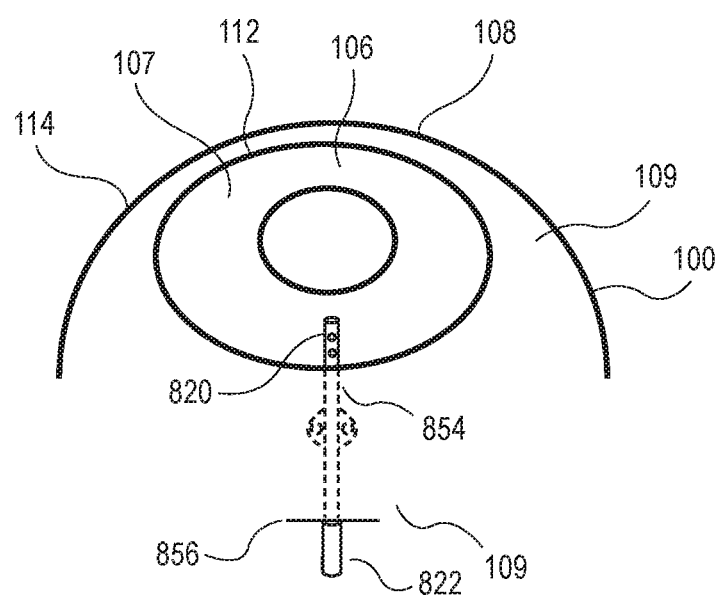
FIG. 96 is a perspective view of an eye showing the ocular device has been delivered by the device delivery system according to one embodiment of this disclosure.

In one embodiment of this invention, the method to deploy the ocular device in the eye 100 to treat glaucoma is provided. Surgical implantation of the ocular device in this invention is less invasive and quicker than other surgical options because the cornea, conjunctiva or the sclera can be accessed easily by the clinicians. As shown in FIG. 91, the device delivery system 850 of the ocular device 854 comprises a hypotube 851 with a distal end 853, and a pushing rod 852 positioned in the hypotube 851 with a pushing handle 855. The distal end 853 of the hypotube 851 includes the deformed ocular device 854 (not shown) that is reduced to a smaller shape. In the embodiment, the ocular device 854 therefore, can be stored in the hypotube 851 prior to expansion as shown in the cross-section view of the delivery system 850 in FIG. 92, thereby requiring a smaller incision 856 for easier implantation. The deformed ocular device 854 is constructed to be expandable once positioned in the eye 100. The implantation procedure requires the creation of an approximately 0.8 to 3.6 mm incision 856 at the implantation site as shown in FIG. 93 without affecting the patient's field of vision. Then distal end 853 (shown in solid line) of the hypotube 851 of the delivery system 850 is inserted into the anterior chamber 106 through the incision 856 as shown in FIG. 94. After the distal end 853 (shown in solid line) of the hypotube 851 is successfully placed in the anterior chamber 106, the distal end 820 of the ocular device 854 is pushed out of the distal end 853 of the hypotube 851 by the pushing rod 852 and expands elastically to its original shape upon released from the distal end 853 as shown in FIG. 95. After the whole ocular device 854 is pushed out of the hypotube tube 851, the hypotube tube 851 is pulled away from the anterior chamber 106. Then the ocular device 854 resiliently regains its original shape as shown in FIG. 96. The distal end 820 is configured to seat in the anterior chamber 106 pointing away from the trabecular meshwork 112. The low-profile compliant tube 822 of the ocular device 854 is configured to protrude out of the exterior surface of the eyeball 100 and to minimize irritation to the eyelids. Driven by the IOP in the eye 100, the aqueous humor starts to drain from the anterior chamber 106 to the tear film 108 of the eye 100 through the implanted ocular device 854.

In an alternative method, the implant procedure may require a suture to secure the ocular device 854 at the implantation site. In yet another embodiment of this invention, the procedure may require an adhesive to secure the ocular device 854 at the implantation site. Alternatively, the ocular device 854 can be inserted through the sclera 109 and into the anterior chamber 106, thereby allowing draining of aqueous humor from the anterior chamber 106 into the tear film 108 of the eyeball 100. Alternatively, the ocular device can be inserted through the limbus 110 of the eye 100 and into the anterior chamber 106, thereby allowing draining of aqueous humor from the anterior chamber 106 into the tear film 108 of the eyeball 100. Alternatively, the ocular device can be inserted through the cornea 107 of the eye 100 and into the anterior chamber 106, thereby allowing draining of aqueous humor from the anterior chamber 106 into the tear film 108 of the eyeball 100. Alternatively, the ocular device can be inserted through the conjunctiva 114 of the eye 100 and into the anterior chamber 106, thereby allowing draining of aqueous humor from the anterior chamber 106 into the tear film 108 of the eyeball 100.

The antimicrobial material comprises material such as metals, metal ion, metal oxide, metal compound, silver, silver oxide, silver nitrate, silver compound, silver nanoparticles, gold, copper, zinc, and platinum. Alternatively, the surface of the fluid conduit comprises an antimicrobial material. Alternatively, the ocular device is made by an antimicrobial material. Alternatively, the surface of the fluid conduit comprises an antifouling material. The antifouling material comprises material such as poly ethylene glycol, poly ethylene glycol copolymers, poly propylene glycol, hydrogel, poly (vinyl alcohol), poly (2-hydroxyethyl methacrylate) (PHEMA), crosslinked PEG diacrylate, Zwitterionic compound, and poly carboxybetaine methacrylate. Alternatively, the ocular device is made by an antifouling material.

The ocular devices in this invention may be made of rigid material, or they may be made of an elastic material such that it is able to be placed in the delivery system for easier penetration through the cornea 107, conjunctiva 114 or sclera 109. After the ocular device is implanted in the eye 100, the ocular device resiliently regains its original shape without blocking the iris 103. Alternatively, the ocular device can be reinforced by materials such as stainless steel, shape memory material, Nitinol, plastic, metal, or fiber. One or more those reinforcement materials according to the invention are sufficient to reliably achieve elasticity for the ocular device. Those reinforcement materials can be braided, woven, or sewed into the ocular device. Alternatively, the reinforcement materials can be wrapped on the surface of the flow conduit. Alternatively, the reinforcement materials can also serve as retainer for the ocular device. The reinforcement materials may also comprise antimicrobial materials such as metals, metal ion, metal oxide, metal compound, silver, silver oxide, silver nitrate, gold, copper, zinc, and platinum.

The ocular device comprises material selected from the group consisting of polymer, silicone, polydimethylsiloxane, silastic, poly 2-hydroxyethylmethacrylate (PHEMA), poly hydroxyethyl methacrylate-methacrylic acid copolymer (polyHEMA-MAA), polymethylmethacrylate (PMMA), silicone/hydrogel combinations, silicone acrylic combinations, fluorosilicone acrylates, acrylic, polyimide, polyethylene, polyethersulfone, polysulfone, hydrogel, polyolefin, polyvinylchloride, polypropylene, polyester, polytetrafluoroethylene (PTFE), expanded polytetrafluoroethylene (ePTFE), polyvinylidene fluoride, polyvinylidene difluoride, regenerated cellulose, cellulose ester, cellulose, polycarbonate, polyamide, antimicrobial material, antimicrobial material/polymer composites, antimicrobial material/silicone composites, ceramic, glass, stainless steel, metal, metal ion, metal oxide, metal compound, silver, silver oxide, silver nitrate, copper, zinc, platinum, titanium, shape memory material, Nitinol, antifouling material, poly ethylene glycol, poly ethylene glycol copolymers, poly propylene glycol, hydrogel, poly (vinyl alcohol), poly (2-hydroxyethyl methacrylate) (PHEMA), crosslinked PEG diacrylate, Zwitterionic compound, and poly carboxybetaine methacrylate. Alternatively, the ocular device and the adjustable flow restrictor can be made by different materials. In another embodiment of this invention, the ocular device and the adjustable flow restrictor may be made by the same material.

The plate or the coating of the ocular device comprises material selected from the group consisting of polymer, silicone, polydimethylsiloxane, silastic, poly 2-hydroxyethylmethacrylate (PHEMA), poly hydroxyethyl methacrylate-methacrylic acid copolymer (polyHEMA-MAA), polymethylmethacrylate (PMMA), silicone/hydrogel combinations, silicone acrylic combinations, fluorosilicone acrylates, acrylic, polyimide, polyethylene, polyethersulfone, polysulfone, hydrogel, polyolefin, polyvinylchloride, polypropylene, polyester, polytetrafluoroethylene (PTFE), expanded polytetrafluoroethylene (ePTFE), polyvinylidene fluoride, polyvinylidene difluoride, regenerated cellulose, cellulose ester, cellulose, polycarbonate, polyamide, antimicrobial material, antimicrobial material/polymer composites, antimicrobial material/silicone composites, ceramic, glass, stainless steel, metal, metal ion, metal oxide, metal compound, silver, silver oxide, silver nitrate, silver compound, silver nanoparticles, copper, zinc, platinum, titanium, shape memory material, Nitinol, antifouling material, poly ethylene glycol, poly ethylene glycol copolymers, poly propylene glycol, hydrogel, poly (vinyl alcohol), poly (2-hydroxyethyl methacrylate) (PHEMA), crosslinked PEG diacrylate, Zwitterionic compound, and poly carboxybetaine methacrylate. Alternatively, the plate or the coating can be made by different materials from that used for the ocular device. In another embodiment of this invention, the plate or the coating can be made by the same materials that used for the ocular device.

EXPERIMENTS AND RESULTS

Experiment 1

Figure 17:
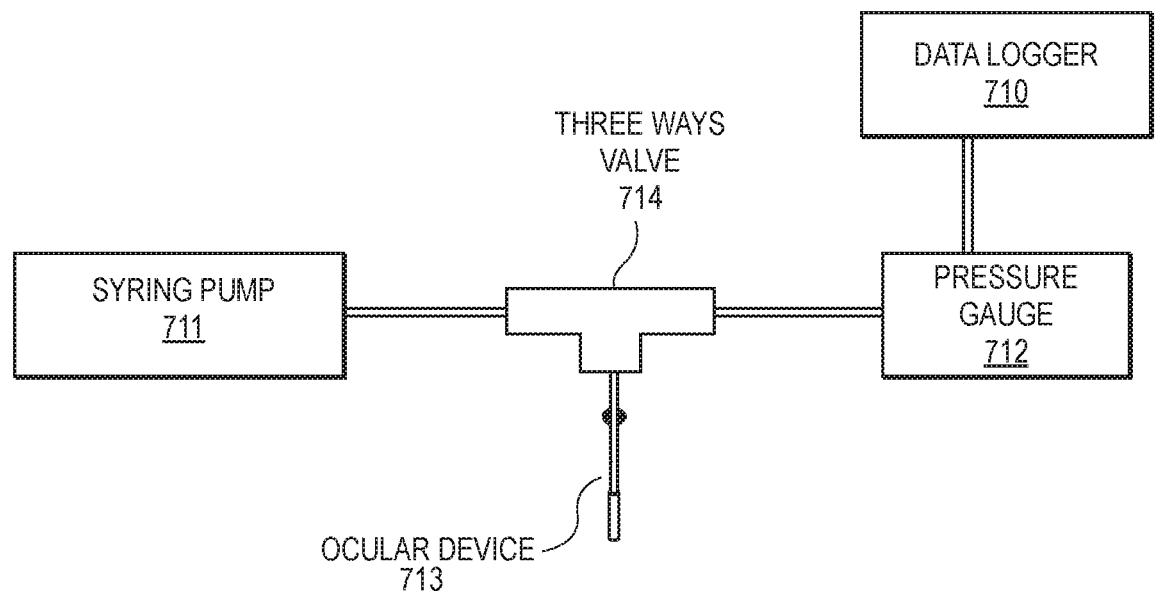
FIG. 17 is the apparatus for measuring the pressure drop through the ocular device. It comprises a syringe pump, a pressure gauge, a three ways valve and a data logger.

A perfusion setup 710 as shown in FIG. 17 was used to measure the outflow facility (Ct) of the ocular device. The apparatus for measuring the pressure drop through the ocular device comprises a syringe pump 711, a pressure gauge 712 and a data logger 713. The syringe pump 711 with adjustable flow rates (Harvard Apparatus Pico Plus pump) was used to set the flow rates in the perfusion system 710. The syringe pump 711 with 10 ml filled syringe is connected to the pressure gauge 712 (General, DM8252) and the ocular device 115 (as shown in FIG. 2) by a three-way stopcock 714. The pressure gauge 712 is connected to the data logger 713 to record the digital output in Lab software (RS232, AZ Instrument Corp.). In this experiment, the pressure through the ocular device 115 at each individual flow rate was recorded. The perfusion setup 710 was tested for accuracy and potential leaks at all flow rates before the start of each experiment. Calibration of the pressure gauge 712 was also performed before each experiment by referencing zero pressure corresponding to zero flow. Several samples (as shown in FIG. 2) with various conduit sizes and lengths were produced for the tests. Each sample was perfused for more than 30 minutes at each flow rate (1.5, 2.5 and 3.0 µL/min) until the pressure reached the steady state. Based on Equation 4, aqueous humor flow rate through the ocular device has a linear relationship to the pressure drop through the ocular device. Thus, the outflow facility of the sample was calculated by the linear regression of the flow rate vs. pressure data in this experiment.

Sample #A includes a fluid conduit of 35 microns in diameter and 20 mm in length. Each pressure drop in the ocular device shown in the Table 1 is an average of at least four measurements. The outflow facility of the Sample #A can be calculated with the flow rate/pressure obtained from the experiment and is shown in the Table 1. Using the expanded Goldmann's equation (Equation 6), individual IOP values before and after device implantation at the three perfusion flow rates (1.5, 2.5, and 3.0 µL/min) were simulated and calculated as shown in Table 1. After device implantation, the ocular device (Sample #A) allows an average 43% reduction in IOP. There was no significant difference in the IOP reduction at all three flow rates. Due to the fluid resistance caused by the conduit geometry (i.e. length, lumen size, tortuosity) of the ocular device, a minimum IOP of 10.8 mmHg is maintained at low aqueous humor formation rate (1.5 µL/min) to avoid hypotony. The ocular device is also capable of reducing the IOP to a normal pressure of 19.3 mmHg at the high aqueous humor formation rate (3.0 µL/min).

TABLE 1

| Sample# | Conduit Inner Diameter (micro meter) | Conduit Outer Diameter (mm) | Conduit Length (mm) | Flow Rate (μ liter per minute) | Measured Pressure Drop in the device (mmHg) | Device Facility (Ct) (μ liter/min per mmHg) | IOP before Implantation (mmHg) | IOP After Implantation (mmHg) |
|---|---|---|---|---|---|---|---|---|
| A | 35 | 0.366 | 20 | 1.5 | 20.9 | 0.08 | 19.0 | 10.8 |
| A | 35 | 0.366 | 20 | 2.5 | 31.0 | 0.08 | 29.0 | 16.5 |
| A | 35 | 0.366 | 20 | 3.0 | 40.9 | 0.08 | 34.0 | 19.3 |

Experiment 2

Sample #B includes a fluid conduit of 35 microns in diameter and 41 mm in length. Each pressure drop in the ocular device shown in the Table is an average of at least four measurements. The outflow device facility of the ocular device (Sample #B) can be calculated with the flow rate/pressure data obtained from the experiment and is shown in Table 2. Its device facility is lower than that of the Sample #A because Sample #B has a longer fluid conduit resulting a higher flow resistance. Using the expanded Goldmann's equation (Equation 6), individual IOP values before and after device implantation at the three perfusion flow rates (1.5, 2.5, and 3.0 μL/min) were simulated and calculated (as shown in Table 2). After device implantation, the ocular device (Sample #B) allows an average 30% reduction in IOP. The lower IOP reduction rate (compared with that of Sample #A) is due to the lower device facility of Sample #B. There was no significant difference in the IOP reduction rate at all three flow rates. With this lower device facility, a minimum IOP of 13.3 mmHg is maintained at the low aqueous humor formation rate (1.5 μL/min) to avoid hypotony. Sample #B is also capable of reducing the IOP from 34 mmHg to 23.8 mmHg at the high aqueous humor formation rate (3.0 μL/min). As expected, the resulting IOP (23.8 mmHg) is higher than that of Sample #A due to its lower device facility.

TABLE 2

| Sample# | Conduit Inner Diameter (micro meter) | Conduit Outer Diameter (mm) | Conduit Length (mm) | Flow Rate (μ liter per minute) | Measured Pressure Drop in the device (mmHg) | Device Facility (Ct) (μ liter/min per mmHg) | IOP before Implantation (mmHg) | IOP After Implantation (mmHg) |
|---|---|---|---|---|---|---|---|---|
| B | 35 | 0.366 | 41 | 1.5 | 40.0 | 0.043 | 19.0 | 13.3 |
| B | 35 | 0.366 | 41 | 2.5 | 60.9 | 0.043 | 29.0 | 20.3 |
| B | 35 | 0.366 | 41 | 3.0 |  | 0.043 | 34.0 | 23.8 |

Experiment 3

Sample #C includes a fluid conduit of 44 microns in diameter and 9 mm in length. Each measured pressure drop in the Table was an average of at least four measurements. The outflow device facility of the ocular device (Sample #C) can be calculated with the flow rate/pressure data obtained from the experiment and is shown in Table 3. The device facility of Sample #C is higher than the device facilities of Samples #A and #B, because Sample #C has a larger fluid conduit diameter and a shorter fluid conduit length, and thereby resulting a lower flow resistance. Using the expanded Goldmann's equation (Equation 6), individual IOP values before and after device implantation at the three perfusion flow rates (1.5, 2.5, and 3.0 μL/min) were simulated and calculated (as shown in Table 3). After device implantation, the ocular device (Sample #C) allows an average 67% reduction in IOP. There was no significant difference in the IOP reduction rate in all three flow rates. Higher device facility in Sample #C leads to a higher IOP reduction rate than Samples #A and #B. Due to the fluid resistance caused by the conduit geometry (i.e. length, lumen size) of the Sample #C, a minimum IOP of 6.2 mmHg is maintained at low aqueous humor formation rate (1.5 μL/min) to avoid hypotony. The ocular device is also capable of reducing the IOP to a normal pressure of 11.1 mmHg at the high aqueous humor formation rate (3.0 μL/min). In addition, the larger fluid conduit lumen size in Sample #C is expected to reduce its chance for clogging.

TABLE 3

| Sample# | Conduit Inner Diameter (micro meter) | Conduit Outer Diameter (mm) | Conduit Length (mm) | Flow Rate (μ liter per minute) | Measured Pressure Drop in the device (mmHg) | Device Facility (Ct) (μ liter/min per mmHg) | IOP before Implantation (mmHg) | IOP After Implantation (mmHg) |
|---|---|---|---|---|---|---|---|---|
| C | 44 | 0.365 | 9 | 1.5 | 12.3 | 0.21 | 19.0 | 6.2 |
| C | 44 | 0.365 | 9 | 2.5 | 15.2 | 0.21 | 29.0 | 9.5 |
| C | 44 | 0.365 | 9 | 3.0 | 19.8 | 0.21 | 34.0 | 11.1 |

Experiment 4

Sample #D includes a fluid conduit of 44 microns in diameter and 12.5 mm in length. Each measured pressure drop in the Table was an average of at least four measurements. The outflow device facility of the ocular device (Sample #D) can be calculated with the flow rate/pressure data obtained from the experiment and is shown in Table 4. The device facility of Sample #D is lower than the device facility of Sample #C, because Sample #D has a longer fluid conduit resulting a higher flow resistance. Using the expanded Goldmann's equation (Equation 6), individual IOP values before and after device implantation at the three perfusion flow rates (1.5, 2.5, and 3.0 μL/min) were simulated as shown in Table 4. After the implantation of the ocular device, the ocular device (Sample #D) allows an average of 57% reduction in IOP due to a lower device facility in Sample #D. There was no significant difference in the IOP reduction rate in all three flow rates. Due to the fluid resistance caused by the fluid conduit geometry (i.e. length, lumen size) of the Sample #D, a minimum IOP of 8.1 mmHg is maintained at low aqueous humor formation rate (1.5 μL/min) to avoid hypotony. Sample #D is also capable of reducing the IOP to a normal pressure of 14.6 mmHg at the high aqueous humor formation rate (3.0 μL/min). Similar to Sample #C, the larger fluid conduit lumen size in Sample #D can reduce its chance for clogging. In addition, the longer conduit length of Sample #D can reduce its chance for bacteria migration through the conduit and the infection risk in the eye.

TABLE 4

| Sample# | Conduit Inner Diameter (micro meter) | Conduit Outer Diameter (mm) | Conduit Length (mm) | Flow Rate (μ liter per minute) | Measured Pressure Drop in the device (mmHg) | Device Facility (Ct) (μ liter/min per mmHg) | IOP before Implantation (mmHg) | IOP After Implantation (mmHg) |
|---|---|---|---|---|---|---|---|---|
| D | 44 | 0.365 | 12.5 | 1.5 | 17.0 | 0.13 | 19.0 | 8.1 |
| D | 44 | 0.365 | 12.5 | 2.5 | 24.1 | 0.13 | 29.0 | 12.4 |
| D | 44 | 0.365 | 12.5 | 3.0 | 28.2 | 0.13 | 34.0 | 14.6 |

Experiment 5

Sample #E includes a fluid conduit of 44 microns in diameter and 25 mm in length. Each measured pressure drop in the Table was an average of at least four measurements. The outflow device facility of the ocular device (Sample #E) can be calculated with the flow rate/pressure data obtained from the experiment and is shown in Table 5. The device facility of Sample #E is lower than the device facility of Sample #D, because the Sample #E has a longer fluid conduit length resulting a higher flow resistance. Using the expanded Goldmann's equation (Equation 6), individual IOP values before and after device implantation at the three perfusion flow rates (1.5, 2.5, and 3.0 μL/min) were simulated as shown in Table 5. After device implantation, the ocular device (Sample #E) allows an average 41% reduction in IOP. There was no significant difference in the IOP reduction rate at all three flow rates. Lower device facility in Sample #E leads to a lower IOP reduction rate than Samples #C and #D. Due to the fluid resistance caused by the fluid conduit geometry (i.e. length, lumen size) of Sample #E, a minimum IOP of 11.2 mmHg is maintained at low aqueous humor formation rate (1.5 μL/min) to avoid hypotony. The ocular device is also capable of reducing the IOP to a normal pressure of 20.1 mmHg at the high aqueous humor formation rate (3.0 μL/min). Similar to Samples #C and #D, the larger fluid conduit lumen size in Sample #E can reduce its chance for clogging. Compared with Samples #C and #D, the longer fluid conduit length of Sample #E can reduce its chance for bacteria migration through the fluid conduit and the infection risk in the eye.

TABLE 5

| Sample# | Conduit Inner Diameter (micro meter) | Conduit Outer Diameter (mm) | Conduit Length (mm) | Flow Rate (μ liter per minute) | Measured Pressure Drop in the device (mmHg) | Device Facility (Ct) (μ liter/min per mmHg) | IOP before Implantation (mmHg) | IOP After Implantation (mmHg) |
|---|---|---|---|---|---|---|---|---|
| E | 44 | 0.365 | 25 | 1.5 | 31.4 | 0.07 | 19.0 | 11.2 |
| E | 44 | 0.365 | 25 | 2.5 | 44.6 | 0.07 | 29.0 | 17.1 |
| E | 44 | 0.365 | 25 | 3.0 | 53.0 | 0.07 | 34.0 | 20.1 |

Experiment 6

Sample #F includes a fluid conduit of 59 microns in diameter and 30 mm in length. Each measured pressure drop in the Table was an average of at least four measurements. The outflow device facility of the ocular device (Sample #F) can be calculated with the data obtained from the experiment and is shown in Table 6. The device facility of Sample #F is higher than the device facility of Sample #E, because Sample #F has a larger fluid conduit lumen size resulting a lower flow resistance. Using the expanded Goldmann's equation (Equation 6), individual IOP values before and after device implantation at the three perfusion flow rates (1.5, 2.5, and 3.0 μL/min) were simulated as shown in Table 6. After device implantation, the ocular device (Sample #F) allows an average 63% reduction in IOP. There was no significant difference in the IOP reduction rate at all three flow rates. Higher device facility in Sample #F leads to a higher IOP reduction rate than Sample #E. Due to the fluid resistance caused by the fluid conduit geometry (i.e. length, lumen size) of Sample #F, a minimum IOP of 7.0 mmHg is maintained at low aqueous humor formation rate (1.5 μL/min) to avoid hypotony. Sample #F is also capable of reducing the IOP to a normal pressure of 12.6 mmHg at the high aqueous humor formation rate (3.0 μL/min). Compared to Sample #E, the larger fluid conduit lumen size in Sample #F can reduce the chance for clogging. The longer conduit length of Sample #F can also reduce its chance for bacteria migration through the fluid conduit and the infection risk in the eye.

TABLE 6

| Sample# | Conduit Inner Diameter (micro meter) | Conduit Outer Diameter (mm) | Conduit Length (mm) | Flow Rate (μ liter per minute) | Measured Pressure Drop in the device (mmHg) | Device Facility (Ct) (μ liter/min per mmHg) | IOP before Implantation (mmHg) | IOP After Implantation (mmHg) |
|---|---|---|---|---|---|---|---|---|
| F | 59 | 0.344 | 30 | 1.5 | 13.1 | 0.17 | 19.0 | 7.0 |
| F | 59 | 0.344 | 30 | 2.5 | 16.7 | 0.17 | 29.0 | 10.7 |
| F | 59 | 0.344 | 30 | 3.0 | 22.1 | 0.17 | 34.0 | 12.6 |

Experiment 7

Sample #G includes a fluid conduit of 59 microns in diameter and 35 mm in length. The outflow device facility of the ocular device (Sample #G) can be calculated with the data obtained from the experiment and is shown in Table 7. Each measured pressure drop in the Table was an average of at least four measurements. The device facility of Sample #G is lower than the device facility of Sample #F, because Sample #G has a longer fluid conduit length resulting a higher flow resistance. Using the expanded Goldmann's equation (Equation 6), individual IOP values before and after device implantation at the three perfusion flow rates (1.5, 2.5, and 3.0 μL/min) were simulated as shown in Table 7. After device implantation, the ocular device (Sample #G) allows an average 60% reduction in IOP. There was no significant difference in the IOP reduction rate at all three flow rates. Lower device facility in Sample #G leads to a lower IOP reduction rate than Sample #F. Due to the fluid resistance caused by the fluid conduit geometry (i.e. length, lumen size) of Sample #G, a minimum IOP of 7.6 mmHg is maintained at low aqueous humor formation rate (1.5 μL/min) to avoid hypotony. Sample #G is also capable of reducing the IOP to a normal pressure of 13.5 mmHg at the high aqueous humor formation rate (3.0 μL/min). Compared to Sample #F, the longer fluid conduit length of Sample #G can reduce its chance for bacteria migration through the fluid conduit and the infection risk in the eye.

TABLE 7

| Sample# | Conduit Inner Diameter (micro meter) | Conduit Outer Diameter (mm) | Conduit Length (mm) | Flow Rate (μ liter per minute) | Measured Pressure Drop in the device (mmHg) | Device Facility (Ct) (μ liter/min per mmHg) | IOP before Implantation (mmHg) | IOP After Implantation (mmHg) |
|---|---|---|---|---|---|---|---|---|
| G | 59 | 0.344 | 35 | 1.5 | 13.6 | 0.15 | 19.0 | 7.6 |
| G | 59 | 0.344 | 35 | 2.5 | 17.7 | 0.15 | 29.0 | 11.6 |
| G | 59 | 0.344 | 35 | 3.0 | 23.8 | 0.15 | 34.0 | 13.5 |

Experiment 8

Sample #H includes a fluid conduit of 72 microns in diameter and 45 mm in length. The outflow device facility of the ocular device (Sample #H) can be calculated with the flow rate/pressure data obtained from the experiment and is shown in Table 8. Each measured pressure drop in the Table was an average of at least four measurements. The device facility of Sample #H is higher than the device facility of Sample #G, because Sample #H has a larger fluid conduit lumen size resulting a lower flow resistance. Using the expanded Goldmann's equation (Equation 6), individual IOP values before and after device implantation at the three perfusion flow rates (1.5, 2.5, and 3.0 μL/min) were simulated as shown in Table 8. After ocular device implantation, the ocular device (Sample #H) allows an average 66% reduction in IOP due to the higher device facility in Sample #H (compared with Sample #G). There was no significant difference in the IOP reduction rate at all three flow rates. Due to the fluid resistance caused by the fluid conduit geometry (i.e. length, lumen size) of Sample #H, a minimum IOP of 6.5 mmHg is maintained at low aqueous humor formation rate (1.5 μL/min) to avoid hypotony. Sample #H is also capable of reducing the IOP to a normal pressure of 11.6 mmHg at the high aqueous humor formation rate (3.0 μL/min). Compared with Sample #G, the larger fluid conduit lumen size in Sample #H can reduce its chance for clogging. The longer fluid conduit length of Sample #H can also reduce its chance (compared with Sample #G) for bacteria migration through the fluid conduit and the infection risk in the eye.

high device facility (Ct) is more effective in draining the aqueous humor, and thereby providing a lower IOP in the eye after the ocular device is implanted. On the other hand, an ocular device with a low device facility can yield a higher IOP in the eye after the ocular device is implanted in the eye. As demonstrated in Samples #A to #H, an ocular device with a larger fluid conduit lumen size (or cross-sectional area) yields a higher device facility, and thereby leading to a lower IOP in the eye. Simultaneously, this larger lumen sizes in the fluid conduit also reduces the chance for clogging caused by the debris in the aqueous humor. Similarly, an ocular device with a shorter fluid conduit length yields a higher device facility, and thereby leading to a lower IOP in the eye. However, an ocular device with a shorter fluid conduit length has a higher risk for bacteria migration through the conduit.

Those examples shown in Sample #A-#H demonstrate that the IOP of the eye can be regulated by the geometry of the ocular device, particularly the geometry (i.e. lumen size and length) of the fluid conduit, without using a valve, a filter or a narrowing in the fluid conduit. A minimal IOP can be maintained by using ocular device with an appropriate conduit lumen size and length to avoid hypotony in the eye.

Experiment 9

A perfusion setup 710 as shown in FIG. 17 was also used to measure the effect of tortuosity on the fluid conduit's length and the outflow facility (Ct) of the ocular device. Several ocular devices (as shown in FIG. 2, Samples #A1 to #D1) with relatively straight fluid conduits were fabricated

TABLE 8

| Sample# | Conduit Inner Diameter (micro meter) | Conduit Outer Diameter (mm) | Conduit Length (mm) | Flow Rate (μ liter per minute) | Measured Pressure Drop in the device (mmHg) | Device Facility (Ct) (μ liter/min per mmHg) | IOP before Implantation (mmHg) | IOP After Implantation (mmHg) |
|---|---|---|---|---|---|---|---|---|
| H | 72 | 0.344 | 45 | 1.5 | 8.0 | 0.19 | 19.0 | 6.5 |
| H | 72 | 0.344 | 45 | 2.5 | 12.3 | 0.19 | 29.0 | 10.0 |
| H | 72 | 0.344 | 45 | 3.0 | 15.2 | 0.19 | 34.0 | 11.6 |

With the perfusion setup 710 shown in FIG. 17, the device facilities of the ocular devices of various conduit lengths and lumen sizes can be calculated as shown in Tables 1-8. The device facility (Ct) is strongly affected by the geometry (i.e. lumen size and length) of the fluid conduit. With a fixed fluid conduit lumen size, the device facility of the ocular device is inversely proportional to the fluid conduit length. On the other hand, the device facility of the ocular device is proportional to the fluid conduit lumen size.

With the expanded Goldmann's equation and the acquired device facility, the IOP of the eye implanted by the ocular devices of various conduit lengths and lumen sizes can be simulated as shown in Tables 1-8. An ocular device with a and tested. On the other hand, several ocular devices (as shown in FIG. 40, Samples #A2 to #D2) with tortuous fluid conduits were also manufactured and tested. All the samples (include devices both straight and tortuous fluid conduits) comprise the same lumen size and total length in the fluid conduit. In this experiment, each ocular device was perfused at 1.5, 2.5 and 3.0 μL/min respectively for more than 30 minutes until the pressure reached the steady state. Based on Equation 4, aqueous humor flow rate through the ocular device has a linear relationship to the pressure drop through the ocular device. Thus, the outflow facility of the ocular device (Ct) was calculated by the linear regression of the flow rate vs. pressure drop data in this experiment.

TABLE 9

| Sample# | Conduit Inner Diameter (micro meter) | Total Conduit Length (mm) | Length between distal and proximal ends (mm) | Flow Rate (μ liter per minute) | Measured Pressure Drop in the device (mmHg) | Device Facility (μ liter/min per mmHg) |
|---|---|---|---|---|---|---|
| A1 | 61 | 30 | 30 | 1.5 | 13.7 | |
| A1 | 61 | 30 | 30 | 2.5 | 21.2 | |
| A1 | 61 | 30 | 30 | 3.0 | 25.8 | |
| A1 | | | | | | 0.123 |
| B1 | 61 | 30 | 30 | 1.5 | 10.3 | |
| B1 | 61 | 30 | 30 | 2.5 | 17.3 | |
| B1 | 61 | 30 | 30 | 3.0 | 22.3 | |
| B1 | | | | | | 0.126 |
| C1 | 61 | 30 | 30 | 1.5 | 15.1 | |
| C1 | 61 | 30 | 30 | 2.5 | 23.0 | |
| C1 | 61 | 30 | 30 | 3.0 | 28.6 | |
| C1 | | | | | | 0.111 |
| D1 | 61 | 30 | 30 | 1.5 | 14.8 | |
| D1 | 61 | 30 | 30 | 2.5 | 21.4 | |
| D1 | 61 | 30 | 30 | 3.0 | 26.6 | |
| D1 | | | | | | 0.129 |
| A2 | 61 | 30 | 14 | 1.5 | 15.5 | |
| A2 | 61 | 30 | 14 | 2.5 | 24.2 | |
| A2 | 61 | 30 | 14 | 3.0 | 29.6 | |
| A2 | | | | | | 0.107 |
| B2 | 61 | 30 | 14 | 1.5 | 13.9 | |
| B2 | 61 | 30 | 14 | 2.5 | 21.5 | |
| B2 | 61 | 30 | 14 | 3.0 | 25.2 | |
| B2 | | | | | | 0.112 |
| C2 | 61 | 30 | 14 | 1.5 | 17.8 | |
| C2 | 61 | 30 | 14 | 2.5 | 25.7 | |
| C2 | 61 | 30 | 14 | 3.0 | 31.7 | |
| C2 | | | | | | 0.108 |
| D2 | 61 | 30 | 14 | 1.5 | 14.2 | |
| D2 | 61 | 30 | 14 | 2.5 | 22.3 | |
| D2 | 61 | 30 | 14 | 3.0 | 27.7 | |
| D2 | | | | | | 0.110 |

TABLE 10

| Measured Pressure Drop in the device (mmHg) | A1 | B1 | C1 | D1 | Average |
|---|---|---|---|---|---|
| 1.5 (□ liter per minute) | 13.7 | 10.3 | 15.1 | 14.8 | 13.5 |
| 2.5 (□ liter per minute) | 21.2 | 17.3 | 23.0 | 21.4 | 20.7 |
| 3.0 (□ liter per minute) | 25.8 | 22.3 | 28.6 | 26.6 | 25.8 |

TABLE 11

| Measured Pressure Drop in the device (mmHg) | A2 | B2 | C2 | D2 | Average |
|---|---|---|---|---|---|
| 1.5 (□ liter per minute) | 15.5 | 13.9 | 17.8 | 14.2 | 15.3 |
| 2.5 (□ liter per minute) | 24.2 | 21.5 | 25.7 | 22.3 | 23.4 |
| 3.0 (□ liter per minute) | 29.6 | 25.2 | 31.7 | 27.7 | 28.5 |

The pressure drops for samples with straight and tortuous conduits at the three perfusion flow rates (1.5, 2.5, and 3.0 μL/min) were measured as shown in Tables 9 to 11. Each measured pressure drop in the Table 9 is an average of at least six measurements. Table 10 lists the average pressure drops for samples with straight conduits at the three perfusion flow rates (1.5, 2.5, and 3.0 μL/min). Table 11 lists the average pressure drops for samples with tortuous conduits at the three perfusion flow rates (1.5, 2.5, and 3.0 μL/min). As shown in Table 10 and 11, the pressure drops of the samples with tortuous conduits (Samples #A2 to #D2) were slightly higher than those samples with the straight conduits (Samples #A1 to #D1) at all three perfusion flow rates. This increase in pressure drops in the samples with tortuous conduits is probably due to the increased aqueous humor turbulent flow and flow resistance in the tortuous fluid conduits (Samples #A2 to #D2).

As demonstrated in this experiment, the samples with tortuous fluid conduits yield a higher flow resistance when the total conduit length remains the same. The higher flow resistance in the tortuous fluid conduit is advantageous in allowing a larger conduit lumen size to avoid clogging caused by the debris in the aqueous humor while maintaining the same flow resistance to prevent hypotony. Furthermore, the tortuosity of the fluid conduit can significantly reduce the linear distance between the proximal end and distal end of the fluid conduit (from 30 mm to 14 mm, as shown in the Table 9), and thereby reducing the risk of interfering with patient's field of vision.

Experiment 10

Figure 97:
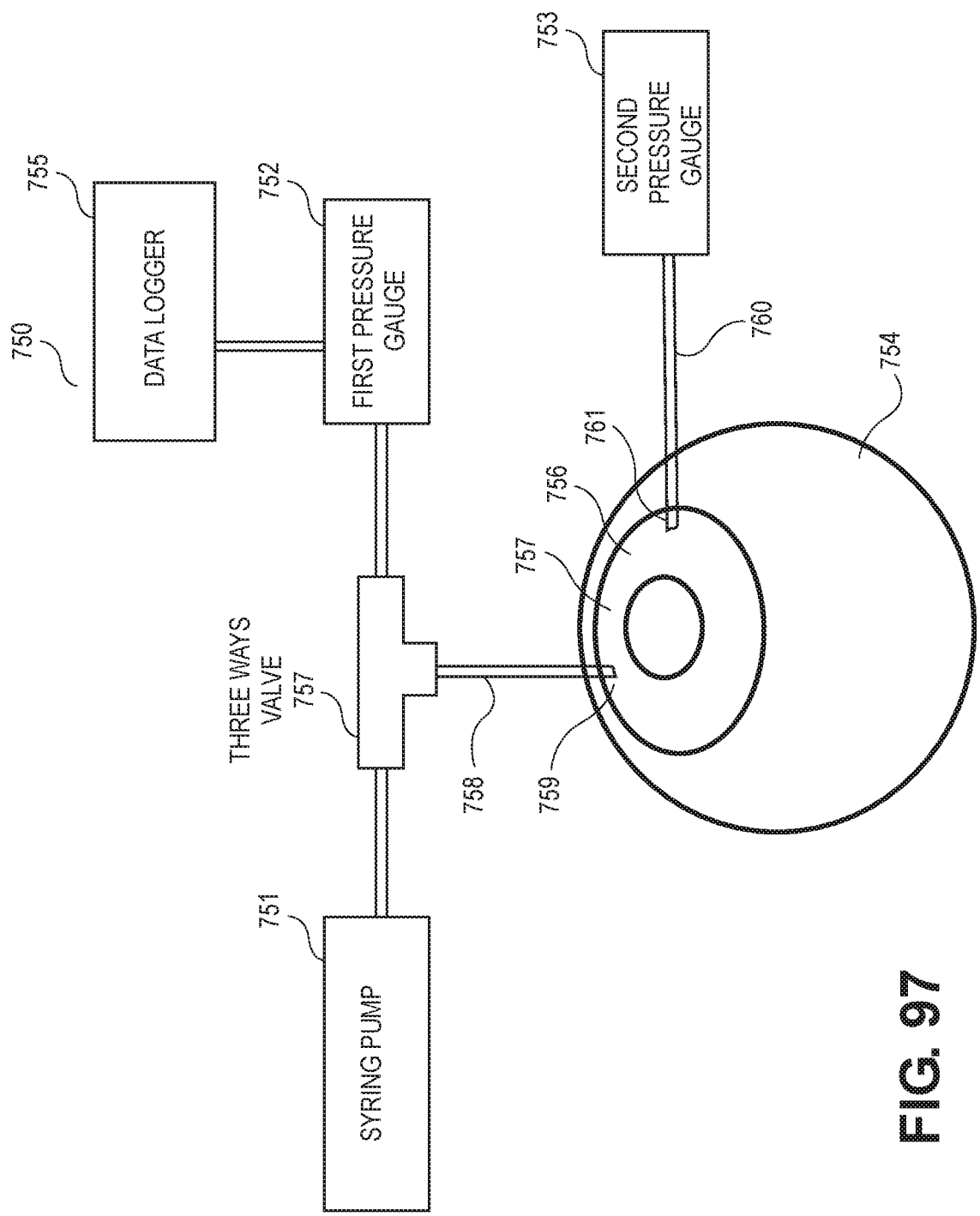
FIG. 97 is a block diagram of a device to measure the IOP of a sheep eye before the ocular device is implanted in the sheep eye.

A perfusion apparatus 750 as shown in FIG. 97 is used to measure the IOP of the sheep eye 754 before and after the ocular device 762 is implanted in the sheep eye 754. The perfusion apparatus 750 for measuring the IOP comprises a syringe pump 751, a first pressure gauge 752, a second pressure gauge 753, a sheep eye 754 and a data logger 755. The syringe pump 751 with adjustable flow rates (Harvard Apparatus Pico Plus pump) will be used to set the flow rates in the perfusion system 750. The syringe pump 751 with 10 ml saline filled syringe is connected to the first pressure gauge 752 (General, DM8252) and the anterior chamber 756 of the sheep eye 754 by a three-way stopcock 757 and a first fluid line 758. The first pressure gauge 752 is also connected to the data logger 755 to record the real-time IOP in Lab software (RS232, AZ Instrument Corp.). The second pressure gauge 753 is also connected to the anterior chamber 756 of the sheep eye 754 to monitor the IOP by a second fluid line 760. The perfusion apparatus 750 will be tested for accuracy and potential leaks at several flow rates before the start of each experiment. Calibration of the pressure gauges 752, 753 will be also performed before each experiment by referencing zero pressure corresponding to zero flow.

In this experiment, the first fluid line 758 (terminated with a 26-gauge needle) will be inserted through the cornea 757 and ending with the needle tip 759 in the anterior chamber 756 of the sheep eye 754. The second fluid line 760 (terminated with a 26-gauge needle) will also be inserted through the cornea 757 and ending with the needle tip 761 in the anterior chamber 756 of the sheep eye 754. Then a water tight closure of both incisions on the cornea 757 will be achieved with an adhesive. The syringe pump 751 (filled with saline) will be set to a flow rate to increase the IOP until it reached a steady-state IOP of ~30 mmHg to ensure the sheep eye 754 is completely inflated. The IOP in the sheep eye 754 will be monitored via the in-line real-time pressure gauges 752, 753 to ensure a steady-state IOP is maintained for at least 60 minutes prior to insertion of the ocular device 762.

Figure 98:
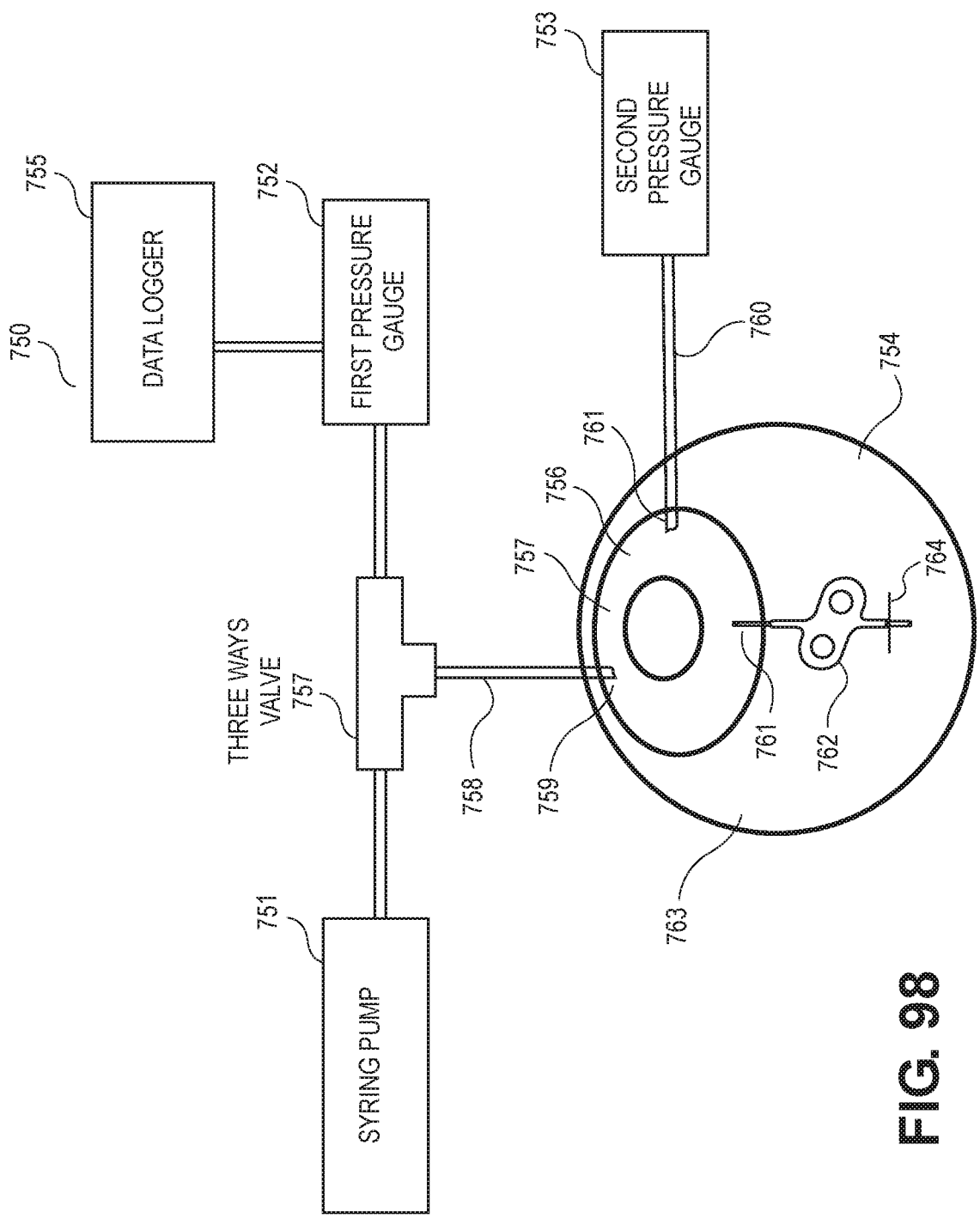
FIG. 98 is a block diagram of the device to measure the IOP of the sheep eye after the ocular device is implanted in the sheep eye.

Several ocular devices 762 (as shown in FIG. 40) with tortuous fluid conduits will be fabricated and tested. Their outflow facilities will be measured and calculated by the method described in Experiment 1. The IOP lowering effect of each ocular device 762 from the baseline in the sheep eye 754 will be determined. As shown in FIG. 98, the ocular device 762 will be inserted in the sheep eye 754 through an incision 764 in the sclera 763 and ending with the distal end 761 of the ocular device 762 in the anterior chamber 756 of the sheep eye 754. Then a water tight closure of the incision 764 will be achieved with an adhesive. The same flow rate to achieve ~30 mmHg IOP will be used after the implantation of the ocular device 762, and post implantation IOP will be measured until a steady state is achieved for at least one hour. It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with another embodiment disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. An ocular device comprising:
a first end configured to seat in an anterior chamber of an eye, the first end including an inlet configured to facilitate an ingress of aqueous humor into the ocular device;
a second end configured to seat in a tear film of the eye, the second end including an outlet configured to facilitate release a flow of the aqueous humor into the tear film; and
a body defining a tortuosity and a fluid conduit, the body including lumen having a lumen length and a lumen cross sectional area, wherein the lumen length and the lumen cross sectional area are configured to control an intraocular pressure (TOP) of the eye by controlling the flow of the aqueous humor through the lumen and wherein the tortuosity of the body is configured to circumferentially circle around an inner perimeter of the anterior chamber in the eye.

2. The ocular device of claim 1, wherein the TOP is controlled without a filter, a valve, or a narrowing in the fluid conduit.

3. The ocular device of claim 1, wherein the lumen includes a lumen cross sectional shape that is circular and the lumen length and the lumen cross sectional area are calculated according to the following equations, $$\Delta P = 8\mu LQ/\pi r^4 \qquad \text{(Equation 1)}$$

wherein,
$\Delta P$ is a pressure difference between the first end and the second end;
L is the length of the fluid conduit;
p is a dynamic viscosity of the aqueous humor, $\mu = 7.2 \times 10^{-4}$ Pa·sec at 37° C.;
Q is a volumetric flow rate of the aqueous humor in the fluid conduit; and
r is a radius of the fluid conduit;

$$R = 1/Ct = 8\mu L/\pi r^4 \qquad \text{(Equation 2)}$$

wherein,
R is a flow resistance between the first end and the second end; and
Ct is a device facility of the ocular device.

4. The ocular device of claim 1, wherein the inlet has a smaller cross sectional area than the lumen cross sectional area to reduce clogging of the ocular device.

5. The ocular device of claim 1, wherein the lumen includes an antimicrobial agent to reduce bacterial ingrowth.

6. The ocular device of claim 5, wherein the antimicrobial agent is selected from the group consisting of antimicrobial agent/polymer composites, antimicrobial agent/silicone composites, ceramic, glass, stainless steel, metal, metal ion, metal oxide, metal compound, silver, silver oxide, silver nitrate, silver compound, silver nanoparticles, copper, zinc, zinc oxide, platinum, and titanium.

7. The ocular device of claim 5, wherein the antimicrobial agent is silver.

8. The ocular device of claim 1, wherein the tortuosity of the body is configured to reside in the anterior chamber of the eye.

9. The ocular device of claim 1, wherein the lumen cross sectional area is configured to increase along the lumen length from the first end to the second end.

10. The ocular device of claim 1, wherein the device further comprises a compliant portion at the second end to reduce irritation to the eye.

11. The ocular device of claim 10, wherein the compliant portion is flexible to comply with eyelid movement.

12. The ocular device of claim 10, wherein the compliant portion is collapsible under pressure from an eyelid of the eye.

13. The ocular device of claim 10, wherein the compliant portion is configured to protrude out of a cornea of the eye when the ocular device is implanted in the cornea.

14. The ocular device of claim 10, wherein the compliant portion is configured to protrude out of a sclera of the eye when the ocular device is implanted in the sclera.

15. The ocular device of claim 10, wherein the compliant portion is configured to protrude out of a conjunctiva of the eye when the ocular device is implanted in the conjunctiva.

16. The ocular device of claim 10, wherein the compliant portion is lubricious to reduce irritation to the eye.

17. The ocular device of claim 1, wherein the ocular device further comprises one or more suture holes to anchor the ocular device in the eye.

18. The ocular device of claim 1, wherein the ocular device further comprises one or more retainers to anchor the ocular device in the eye.

19. The ocular device of claim 18, wherein the retainers are selected from the group comprising fiber, wire, thread, bump, nodule, ridge, protrusion, mesh, brush, foam, and scaffold.

20. The ocular device of claim 1, wherein the ocular device further comprises an adjustable flow restrictor with a distal end and a proximal end, wherein the distal end is configured to seat in the fluid conduit; wherein the proximal end is configured to position in the tear film of the eye.

21. The ocular device of claim 20, wherein the TOP of the eye and the flow resistance of the ocular device are adjustable non-invasively by controlling one or both of a length of the adjustable flow restrictor and a cross sectional area of the adjustable flow restrictor while the ocular device is implanted in the eye.

22. The ocular device of claim 20, wherein the adjustable flow restrictor is tapered along the length from the proximal end to the distal end.

23. The ocular device of claim 20, wherein the adjustable flow restrictor comprises a wire.

24. The ocular device of claim 20, wherein the adjustable flow restrictor comprises a plurality of wires with various lengths.

25. The ocular device of claim 20, wherein the adjustable flow restrictor comprises a tube.

26. The ocular device of claim 20, wherein the adjustable flow restrictor comprises a drug.

27. The ocular device of claim 1, wherein the first end further comprises a plurality of inlets.

28. The ocular device of claim 1, wherein the inlet faces away from the trabecular meshwork.

29. The ocular device of claim 1, wherein the lumen includes an antifouling material selected from the group consisting of poly ethylene glycol, poly ethylene glycol copolymers, poly propylene glycol, hydrogel, poly (vinyl alcohol), poly (2-hydroxyethyl methacrylate) (PHEMA), crosslinked PEG diacrylate, Zwitterionic compound, and poly carboxybetaine methacrylate.

30. The ocular device of claim 1, wherein the ocular device comprises a material selected from the group consisting of polymer, silicone, polydimethylsiloxane, silastic, poly 2-hydroxyethylmethacrylate (PHEMA), poly hydroxyethyl methacrylate-methacrylic acid copolymer (poly-HEMA-MAA), polymethylmethacrylate (PMMA), silicone/hydrogel combinations, silicone acrylic combinations, fluorosilicone acrylates, acrylic, polyimide, polyethylene, polyethersulfone, polysulfone, hydrogel, polyolefin, polyvinylchloride, polypropylene, polyester, polytetrafluoroethylene (PTFE), expanded polytetrafluoroethylene (ePTFE), polyvinylidene fluoride, polyvinylidene difluoride, regenerated cellulose, cellulose ester, cellulose, polycarbonate, polyamide, antimicrobial material, antimicrobial material/polymer composites, antimicrobial material/silicone composites, ceramic, glass, stainless steel, metal, metal ion, metal oxide, metal compound, silver, silver oxide, silver nitrate, silver compound, silver nanoparticles, copper, zinc, zinc oxide, platinum, titanium, shape memory material, Nitinol, antifouling material, poly ethylene glycol, poly ethylene glycol copolymers, poly propylene glycol, hydrogel, poly (vinyl alcohol), poly (2-hydroxyethyl methacrylate) (PHEMA), crosslinked PEG diacrylate, Zwitterionic compound, and poly carboxybetaine methacrylate.

31. The ocular device of claim 1, wherein the ocular device further comprises a plate or a coating to retain the shape of the ocular device and protect the ocular device.

32. The ocular device of claim 31, wherein the ocular device is integrated with the plate or the coating.

33. A method for treating a patient having glaucoma, the method comprising:
(a) measuring a pre-operative intraocular pressure (TOP) in an eye of the patient;
(b) implanting the ocular device of claim 1 into the eye, wherein at least one of the lumen length and the lumen cross sectional area is selected in response to the measured pre-operative TOP; and
(c) measuring a post-operative TOP to confirm treatment of the patient.

34. The method of claim 33, further comprising adjusting an adjustable flow restrictor in response to the post-operative TOP being outside a normal TOP range.

* * * * *

UNITED STATES PATENT AND TRADEMARK OFFICE
CERTIFICATE OF CORRECTION

PATENT NO. : 11,446,179 B2
APPLICATION NO. : 16/374096
DATED : September 20, 2022
INVENTOR(S) : Jack Chu Page 1 of 1

It is certified that error appears in the above-identified patent and that said Letters Patent is hereby corrected as shown below:

In the Claims

Column 86, Claim 1, Line 15: "(TOP)" should be replaced with --(IOP)--

Column 86, Claim 2, Line 20: "(TOP)" should be replaced with --(IOP)--

Column 86, Claim 3, Line 33: "p is a dynamic viscosity" should be replaced with --$\mu$ is a dynamic viscosity--

Column 87, Claim 21, Line 30: "(TOP)" should be replaced with --(IOP)--

Column 88, Claim 33, Line 39: "(TOP)" should be replaced with --(IOP)--

Column 88, Claim 33, Line 44: "(TOP)" should be replaced with --(IOP)--

Column 88, Claim 33, Line 45: "(TOP)" should be replaced with --(IOP)--

Column 88, Claim 34, Line 49: "(TOP)" should be replaced with --(IOP)--

Signed and Sealed this
Twenty-seventh Day of June, 2023

Katherine Kelly Vidal
*Director of the United States Patent and Trademark Office*